(12) United States Patent
Khairkhahan et al.

(10) Patent No.: US 12,350,153 B2
(45) Date of Patent: Jul. 8, 2025

(54) SYSTEMS AND METHODS FOR TRANSCATHETER TREATMENT OF VALVE REGURGITATION

(71) Applicant: Polares Medical Inc., Palo Alto, CA (US)

(72) Inventors: Alexander K. Khairkhahan, Palo Alto, CA (US); Michael D. Lesh, Mill Valley, CA (US); Alan R. Klenk, San Jose, CA (US)

(73) Assignee: Polares Medical Inc., Palo Alto, CA (US)

( * ) Notice: Subject to any disclaimer, the term of this patent is extended or adjusted under 35 U.S.C. 154(b) by 638 days.

(21) Appl. No.: 17/227,749

(22) Filed: Apr. 12, 2021

(65) Prior Publication Data
US 2021/0298901 A1 Sep. 30, 2021

Related U.S. Application Data

(63) Continuation of application No. 16/220,322, filed on Dec. 14, 2018, now Pat. No. 11,000,372, which is a
(Continued)

(51) Int. Cl.
*A61F 2/24* (2006.01)
*A61B 17/04* (2006.01)
(Continued)

(52) U.S. Cl.
CPC ........ *A61F 2/2442* (2013.01); *A61B 17/0401* (2013.01); *A61F 2/2454* (2013.01);
(Continued)

(58) Field of Classification Search
None
See application file for complete search history.

(56) References Cited

U.S. PATENT DOCUMENTS 3,491,376 A   1/1970   Shiley
3,503,079 A   3/1970   Smith
(Continued)

FOREIGN PATENT DOCUMENTS

CN   102256568   12/2002
CN     1984621    6/2007
(Continued)

OTHER PUBLICATIONS

Office Action for JP 2021-212699 dated Dec. 6, 2022.
(Continued)

*Primary Examiner* — Leslie A Lopez
(74) *Attorney, Agent, or Firm* — Knobbe, Martens, Olson & Bear, LLP

(57) ABSTRACT

The invention relates to a device for use in the transcatheter treatment of mitral valve regurgitation, specifically a coaptation assistance devices for implantation across the valve; a system including the coaptation enhancement element and anchors for implantation; a system including the coaptation enhancement element, and one or more of the following: transseptal sheath, anchor delivery catheter, implant delivery catheter, and clip delivery catheter; and methods for transcatheter implantation of a coaptation element across a heart valve.

15 Claims, 28 Drawing Sheets

Related U.S. Application Data continuation of application No. 14/313,975, filed on Jun. 24, 2014, now Pat. No. 10,166,098.

(60) Provisional application No. 61/895,647, filed on Oct. 25, 2013.

(51) Int. Cl.
*A61B 17/00* (2006.01)
*A61B 17/064* (2006.01)

(52) U.S. Cl.
CPC .......... *A61F 2/2463* (2013.01); *A61F 2/2466* (2013.01); *A61B 2017/00243* (2013.01); *A61B 2017/0414* (2013.01); *A61B 2017/0441* (2013.01); *A61B 2017/0649* (2013.01); *A61F 2/2412* (2013.01); *A61F 2210/0014* (2013.01); *A61F 2220/0008* (2013.01)

(56) References Cited

U.S. PATENT DOCUMENTS

| | | |
|---|---|---|
| 3,656,185 A | 4/1972 | Carpentier |
| 3,671,979 A | 6/1972 | Moulopoulos |
| 3,874,388 A | 4/1975 | King et al. |
| 3,898,701 A | 8/1975 | La Russa |
| 3,938,197 A | 2/1976 | Milo |
| 4,007,743 A | 2/1977 | Blake |
| 4,011,601 A | 3/1977 | Clune et al. |
| 4,042,979 A | 8/1977 | Angell |
| 4,078,268 A | 3/1978 | Possis |
| 4,204,283 A | 5/1980 | Bellhouse et al. |
| 4,218,783 A | 8/1980 | Reul et al. |
| 4,261,342 A | 4/1981 | Aranguren Duo |
| 4,263,680 A | 4/1981 | Ruel et al. |
| 4,275,469 A | 6/1981 | Gabbay |
| RE31,040 E | 9/1982 | Possis |
| 4,352,211 A | 10/1982 | Parravicini |
| 4,488,318 A | 12/1984 | Kaster |
| 4,490,859 A | 1/1985 | Black et al. |
| 4,491,986 A | 1/1985 | Gabbay |
| 4,561,129 A | 12/1985 | Arpesella |
| 4,687,483 A | 8/1987 | Fisher et al. |
| 4,705,516 A | 11/1987 | Barone et al. |
| 4,759,758 A | 7/1988 | Gabbay |
| 4,790,843 A | 12/1988 | Carpentier et al. |
| 4,960,424 A | 10/1990 | Grooters |
| 4,994,077 A | 2/1991 | Dobben |
| 5,002,567 A | 3/1991 | Bona et al. |
| 5,078,737 A | 1/1992 | Bona et al. |
| 5,131,905 A | 7/1992 | Grooters |
| 5,197,980 A | 3/1993 | Gorshkov et al. |
| 5,217,484 A | 6/1993 | Marks |
| 5,258,023 A | 11/1993 | Reger |
| 5,332,402 A | 7/1994 | Teitelbaum |
| 5,344,442 A | 9/1994 | Deac |
| 5,370,662 A | 12/1994 | Stone et al. |
| 5,397,347 A | 3/1995 | Cuilleron et al. |
| 5,397,348 A | 3/1995 | Campbell et al. |
| 5,413,599 A | 5/1995 | Imachi et al. |
| 5,487,760 A | 1/1996 | Villafana |
| 5,500,015 A | 3/1996 | Deac |
| 5,522,886 A | 6/1996 | Milo |
| 5,554,186 A | 9/1996 | Guo et al. |
| 5,582,616 A | 12/1996 | Bolduc et al. |
| 5,593,435 A | 1/1997 | Carpentier et al. |
| 5,626,613 A | 5/1997 | Schmieding |
| 5,658,313 A | 8/1997 | Thal |
| 5,662,683 A | 9/1997 | Kay |
| 5,662,704 A | 9/1997 | Gross |
| 5,716,370 A | 2/1998 | Williamson, IV et al. |
| 5,733,331 A | 3/1998 | Peredo |
| 5,824,065 A | 10/1998 | Gross |
| 5,824,066 A | 10/1998 | Gross |
| 5,824,067 A | 10/1998 | Gross |
| 5,855,601 A | 1/1999 | Bessler et al. |
| 5,888,240 A | 3/1999 | Carpentier et al. |
| 5,957,949 A | 9/1999 | Leonhardt et al. |
| 6,007,577 A | 12/1999 | Vanney et al. |
| 6,024,096 A | 2/2000 | Buckberg |
| 6,042,607 A | 3/2000 | Williamson, IV et al. |
| 6,045,497 A | 4/2000 | Schweich et al. |
| 6,045,573 A | 4/2000 | Wenstrom et al. |
| 6,063,114 A | 5/2000 | Nash et al. |
| 6,066,160 A | 5/2000 | Colvin et al. |
| 6,086,612 A | 7/2000 | Jansen |
| 6,113,631 A | 9/2000 | Jansen |
| 6,162,233 A | 12/2000 | Williamson, IV et al. |
| 6,217,610 B1 | 4/2001 | Carpentier et al. |
| 6,221,104 B1 | 4/2001 | Buckberg et al. |
| 6,250,308 B1 | 6/2001 | Cox |
| 6,264,602 B1 | 7/2001 | Mortier et al. |
| 6,287,339 B1 | 9/2001 | Vazquez et al. |
| 6,296,662 B1 | 10/2001 | Caffey |
| 6,299,637 B1 | 10/2001 | Shaolian et al. |
| 6,312,447 B1 | 11/2001 | Grimes |
| 6,312,464 B1 | 11/2001 | Navia |
| 6,332,893 B1 | 12/2001 | Mortier et al. |
| 6,358,277 B1 | 3/2002 | Duran |
| 6,383,147 B1 | 5/2002 | Stobie |
| 6,391,053 B1 | 5/2002 | Brendzel et al. |
| 6,391,054 B2 | 5/2002 | Carpentier et al. |
| 6,402,679 B1 | 6/2002 | Mortier et al. |
| 6,402,780 B2 | 6/2002 | Williamson, IV et al. |
| 6,409,758 B2 | 6/2002 | Stobie et al. |
| 6,419,695 B1 | 7/2002 | Gabbay |
| 6,439,237 B1 | 8/2002 | Buckberg et al. |
| 6,450,171 B1 | 9/2002 | Buckberg et al. |
| 6,451,024 B1 | 9/2002 | Thompson et al. |
| 6,454,799 B1 | 9/2002 | Schreck |
| 6,458,153 B1 | 10/2002 | Bailey et al. |
| 6,482,228 B1 | 11/2002 | Norred |
| 6,540,782 B1 | 4/2003 | Snyders |
| 6,544,167 B2 | 4/2003 | Buckberg et al. |
| 6,551,302 B1 | 4/2003 | Rosinko et al. |
| 6,565,603 B2 | 5/2003 | Cox |
| 6,569,198 B1 | 5/2003 | Wilson |
| 6,602,288 B1 | 8/2003 | Cosgrove et al. |
| 6,602,289 B1 | 8/2003 | Colvin et al. |
| 6,626,930 B1 | 9/2003 | Allen et al. |
| 6,629,534 B1 | 10/2003 | St. Goar et al. |
| 6,652,578 B2 | 11/2003 | Bailey et al. |
| 6,676,698 B2 | 1/2004 | McGuckin, Jr. et al. |
| 6,682,559 B2 | 1/2004 | Myers et al. |
| 6,702,852 B2 | 3/2004 | Stobie et al. |
| 6,719,790 B2 | 4/2004 | Brendzel et al. |
| 6,752,813 B2 | 6/2004 | Goldfarb et al. |
| 6,764,510 B2 | 7/2004 | Vidlund et al. |
| 6,780,200 B2 | 8/2004 | Jansen |
| 6,790,237 B2 | 9/2004 | Stinson |
| 6,797,002 B2 | 9/2004 | Spence et al. |
| 6,800,090 B2 | 10/2004 | Alferness et al. |
| 6,805,710 B2 | 10/2004 | Bolling et al. |
| 6,821,297 B2 | 11/2004 | Snyders |
| 6,837,247 B2 | 1/2005 | Buckberg et al. |
| 6,840,246 B2 | 1/2005 | Downing |
| 6,846,324 B2 | 1/2005 | Stobie |
| 6,869,444 B2 | 3/2005 | Gabbay |
| 6,908,478 B2 | 6/2005 | Alferness et al. |
| 6,911,043 B2 | 6/2005 | Myers et al. |
| 6,926,730 B1 | 8/2005 | Nguyen et al. |
| 6,966,925 B2 | 11/2005 | Stobie |
| 6,991,649 B2 | 1/2006 | Sievers |
| 6,997,950 B2 | 2/2006 | Chawla |
| 7,018,408 B2 | 3/2006 | Bailey et al. |
| 7,037,333 B2 | 5/2006 | Myers et al. |
| 7,048,754 B2 | 5/2006 | Martin et al. |
| 7,056,280 B2 | 6/2006 | Buckberg et al. |
| 7,070,618 B2 | 7/2006 | Streeter |
| 7,077,861 B2 | 7/2006 | Spence |
| 7,077,862 B2 | 7/2006 | Vidlund et al. |
| 7,083,628 B2 | 8/2006 | Bachman |
| 7,087,064 B1 | 8/2006 | Hyde |
| 7,112,207 B2 | 9/2006 | Allen et al. |

(56) References Cited

U.S. PATENT DOCUMENTS

| | | |
|---|---|---|
| 7,122,043 B2 | 10/2006 | Greenhalgh et al. |
| 7,160,322 B2 | 1/2007 | Gabbay |
| 7,166,126 B2 | 1/2007 | Spence et al. |
| 7,175,656 B2 | 2/2007 | Khairkhahan |
| 7,195,641 B2 | 3/2007 | Palmaz et al. |
| 7,217,284 B2 | 5/2007 | Houser et al. |
| 7,226,467 B2 | 6/2007 | Lucatero et al. |
| 7,275,546 B2 | 10/2007 | Buckberg et al. |
| 7,291,168 B2 | 11/2007 | Macoviak et al. |
| 7,294,148 B2 | 11/2007 | McCarthy |
| 7,296,577 B2 | 11/2007 | Taylor et al. |
| 7,316,706 B2 | 1/2008 | Bloom et al. |
| 7,320,704 B2 | 1/2008 | Lashinski et al. |
| 7,335,213 B1 | 2/2008 | Hyde et al. |
| 7,338,520 B2 | 3/2008 | Bailey et al. |
| 7,341,584 B1 | 3/2008 | Starkey |
| 7,357,814 B2 | 4/2008 | Gabbay |
| 7,374,572 B2 | 5/2008 | Gabbay |
| RE40,377 E | 6/2008 | Williamson, IV et al. |
| 7,381,220 B2 | 6/2008 | Macoviak et al. |
| 7,396,364 B2 | 7/2008 | Moaddeb et al. |
| 7,404,824 B1 | 7/2008 | Webler et al. |
| 7,435,257 B2 | 10/2008 | Lashinski et al. |
| 7,445,630 B2 | 11/2008 | Lashinski et al. |
| 7,455,689 B2 | 11/2008 | Johnson |
| 7,485,143 B2 | 2/2009 | Webler et al. |
| 7,510,573 B2 | 3/2009 | Gabbay |
| 7,510,576 B2 | 3/2009 | Langberg et al. |
| 7,527,646 B2 | 5/2009 | Rahdert et al. |
| 7,527,647 B2 | 5/2009 | Spence |
| 7,530,998 B1 | 5/2009 | Starkey |
| 7,534,259 B2 | 5/2009 | Lashinski et al. |
| 7,556,645 B2 | 7/2009 | Lashinski et al. |
| 7,559,936 B2 | 7/2009 | Levine |
| 7,563,267 B2 | 7/2009 | Goldfarb et al. |
| 7,563,273 B2 | 7/2009 | Goldfarb et al. |
| 7,591,847 B2 | 9/2009 | Navia et al. |
| 7,608,091 B2 | 10/2009 | Goldfarb et al. |
| 7,611,534 B2 | 11/2009 | Kapadia et al. |
| 7,621,948 B2 | 11/2009 | Herrmann et al. |
| 7,648,532 B2 | 1/2010 | Greenhalgh et al. |
| 7,655,015 B2 | 2/2010 | Goldfarb et al. |
| 7,658,762 B2 | 2/2010 | Lashinski et al. |
| 7,658,763 B2 | 2/2010 | Stobie |
| 7,666,224 B2 | 2/2010 | Vidlund et al. |
| 7,674,286 B2 | 3/2010 | Alfieri et al. |
| 7,678,145 B2 | 3/2010 | Vidlund et al. |
| 7,682,391 B2 | 3/2010 | Johnson |
| 7,691,144 B2 | 4/2010 | Chang et al. |
| 7,699,892 B2 | 4/2010 | Rafiee et al. |
| 7,704,269 B2 | 4/2010 | St. Goar et al. |
| 7,704,277 B2 | 4/2010 | Zakay et al. |
| 7,736,388 B2 | 6/2010 | Goldfarb et al. |
| 7,740,638 B2 | 6/2010 | Hyde |
| 7,744,609 B2 | 6/2010 | Allen et al. |
| 7,753,923 B2 | 7/2010 | St. Goar et al. |
| 7,758,491 B2 | 7/2010 | Buckner et al. |
| 7,758,595 B2 | 7/2010 | Allen et al. |
| 7,776,084 B2 | 8/2010 | Johnson |
| 7,785,366 B2 | 8/2010 | Maurer et al. |
| 7,799,038 B2 | 9/2010 | Sogard et al. |
| 7,803,187 B2 | 9/2010 | Hauser |
| 7,819,915 B2 | 10/2010 | Stobie et al. |
| 7,846,203 B2 | 12/2010 | Cribier |
| 7,887,552 B2 | 2/2011 | Bachman |
| 7,901,454 B2 | 3/2011 | Kapadia et al. |
| 7,909,866 B2 | 3/2011 | Stobie |
| 7,914,576 B2 | 3/2011 | Navia et al. |
| 7,927,370 B2 | 4/2011 | Webler et al. |
| 7,935,144 B2 | 5/2011 | Robin et al. |
| 7,935,145 B2 | 5/2011 | Alfieri et al. |
| 7,938,827 B2 | 5/2011 | Hauck et al. |
| 7,942,928 B2 | 5/2011 | Webler et al. |
| 7,951,195 B2 | 5/2011 | Antonsson et al. |
| 7,951,196 B2 | 5/2011 | McCarthy |
| 7,955,385 B2 | 6/2011 | Crittenden |
| 7,959,673 B2 | 6/2011 | Carpentier et al. |
| 7,981,139 B2 | 7/2011 | Martin et al. |
| 7,988,725 B2 | 8/2011 | Gross et al. |
| 7,993,396 B2 | 8/2011 | McCarthy |
| 7,998,151 B2 | 8/2011 | St. Goar et al. |
| 8,012,201 B2 | 9/2011 | Lashinski et al. |
| 8,012,202 B2 | 9/2011 | Alameddine |
| 8,016,882 B2 | 9/2011 | Macoviak et al. |
| 8,029,518 B2 | 10/2011 | Goldfarb et al. |
| 8,052,751 B2 | 11/2011 | Aklog et al. |
| 8,057,493 B2 | 11/2011 | Goldfarb et al. |
| 8,062,355 B2 | 11/2011 | Figulla et al. |
| 8,070,804 B2 | 12/2011 | Hyde et al. |
| 8,070,805 B2 | 12/2011 | Vidlund et al. |
| 8,092,525 B2 | 1/2012 | Eliasen et al. |
| 8,118,866 B2 | 2/2012 | Herrmann et al. |
| 8,128,691 B2 | 3/2012 | Keranen |
| 8,133,272 B2 | 3/2012 | Hyde |
| 8,142,494 B2 | 3/2012 | Rahdert et al. |
| 8,142,495 B2 | 3/2012 | Hasenkam et al. |
| 8,147,542 B2 | 4/2012 | Maisano et al. |
| 8,152,844 B2 | 4/2012 | Rao et al. |
| 8,163,013 B2 | 4/2012 | Machold et al. |
| 8,187,207 B2 | 5/2012 | Machold et al. |
| 8,187,299 B2 | 5/2012 | Goldfarb et al. |
| 8,187,323 B2 | 5/2012 | Mortier et al. |
| 8,204,605 B2 | 6/2012 | Hastings et al. |
| 8,206,439 B2 | 6/2012 | Gomez Duran |
| 8,216,230 B2 | 7/2012 | Hauck et al. |
| 8,216,256 B2 | 7/2012 | Raschdorf, Jr. et al. |
| 8,216,302 B2 | 7/2012 | Wilson et al. |
| 8,216,303 B2 | 7/2012 | Navia |
| 8,221,493 B2 | 7/2012 | Boyle et al. |
| 8,226,711 B2 | 7/2012 | Mortier et al. |
| 8,241,304 B2 | 8/2012 | Bachman |
| 8,241,351 B2 | 8/2012 | Cabiri |
| 8,252,050 B2 | 8/2012 | Maisano |
| 8,252,051 B2 | 8/2012 | Chau et al. |
| 8,262,725 B2 | 9/2012 | Subramanian |
| 8,277,502 B2 | 10/2012 | Miller et al. |
| 8,287,591 B2 | 10/2012 | Keidar et al. |
| 8,292,884 B2 | 10/2012 | Levine et al. |
| 8,308,796 B2 | 11/2012 | Lashinski et al. |
| 8,323,336 B2 | 12/2012 | Hill et al. |
| 8,337,390 B2 | 12/2012 | Ferrazzi |
| 8,353,956 B2 | 1/2013 | Miller et al. |
| 8,361,086 B2 | 1/2013 | Allen et al. |
| 8,377,118 B2 | 2/2013 | Lashinski et al. |
| 8,382,796 B2 | 2/2013 | Blaeser et al. |
| 8,382,828 B2 | 2/2013 | Roberts |
| 8,382,829 B1 | 2/2013 | Call et al. |
| RE44,075 E | 3/2013 | Williamson et al. |
| 8,398,708 B2 | 3/2013 | Meiri et al. |
| 8,408,214 B2 | 4/2013 | Spenser |
| 8,413,573 B2 | 4/2013 | Rebecchi |
| 8,414,644 B2 | 4/2013 | Quadri et al. |
| 8,449,606 B2 | 5/2013 | Eliasen et al. |
| 8,454,683 B2 | 6/2013 | Rafiee et al. |
| 8,470,028 B2 | 6/2013 | Thornton et al. |
| 8,500,800 B2 | 8/2013 | Maisano et al. |
| 8,506,624 B2 | 8/2013 | Vidlund et al. |
| 8,523,881 B2 | 9/2013 | Cabiri et al. |
| 8,545,553 B2 | 10/2013 | Zipory et al. |
| 8,608,797 B2 | 12/2013 | Gross et al. |
| 8,657,872 B2 | 2/2014 | Seguin |
| 8,690,939 B2 | 4/2014 | Miller et al. |
| 8,715,342 B2 | 5/2014 | Zipory et al. |
| 8,734,467 B2 | 5/2014 | Miller et al. |
| 8,784,483 B2 | 7/2014 | Navia |
| 8,790,394 B2 | 7/2014 | Miller et al. |
| 8,795,352 B2 | 8/2014 | O'beirne et al. |
| 8,808,368 B2 | 8/2014 | Maisano et al. |
| 8,845,717 B2 | 9/2014 | Khairkhahan et al. |
| 8,858,623 B2 | 10/2014 | Miller et al. |
| 8,888,843 B2 | 11/2014 | Khairkhahan et al. |
| 8,888,844 B2 | 11/2014 | Eliasen et al. |
| 8,911,494 B2 | 12/2014 | Hammer et al. |
| 8,926,695 B2 | 1/2015 | Gross et al. |

(56) References Cited

U.S. PATENT DOCUMENTS

| | | |
|---|---|---|
| 8,926,696 B2 | 1/2015 | Cabiri et al. |
| 8,926,697 B2 | 1/2015 | Gross et al. |
| 8,940,042 B2 | 1/2015 | Miller et al. |
| 8,940,044 B2 | 1/2015 | Hammer et al. |
| 8,968,395 B2 | 3/2015 | Hauser et al. |
| 9,005,279 B2 | 4/2015 | Gabbay |
| 9,011,520 B2 | 4/2015 | Miller et al. |
| 9,011,530 B2 | 4/2015 | Reich et al. |
| 9,056,006 B2 | 6/2015 | Edelman et al. |
| 9,119,719 B2 | 9/2015 | Zipory et al. |
| 9,180,007 B2 | 11/2015 | Reich et al. |
| 9,192,472 B2 | 11/2015 | Gross et al. |
| 9,204,964 B2 | 12/2015 | Dahlgren et al. |
| 9,232,999 B2 | 1/2016 | Maurer et al. |
| 9,265,608 B2 | 2/2016 | Miller et al. |
| 9,277,994 B2 | 3/2016 | Miller et al. |
| 9,351,830 B2 | 5/2016 | Gross et al. |
| 9,414,921 B2 | 8/2016 | Miller et al. |
| 9,452,048 B2 | 9/2016 | O'beirne et al. |
| 9,474,606 B2 | 10/2016 | Zipory et al. |
| 9,526,613 B2 | 12/2016 | Gross et al. |
| 9,549,817 B2 | 1/2017 | Rafiee |
| 9,554,906 B2 | 1/2017 | Aklog et al. |
| 9,561,104 B2 | 2/2017 | Miller et al. |
| 9,592,118 B2 | 3/2017 | Khairkhahan et al. |
| 9,592,121 B1 | 3/2017 | Khairkhahan |
| 9,592,122 B2 | 3/2017 | Zipory et al. |
| 9,610,161 B2 | 4/2017 | Macoviak et al. |
| 9,610,162 B2 | 4/2017 | Zipory et al. |
| 9,610,163 B2 | 4/2017 | Khairkhahan et al. |
| 9,622,861 B2 | 4/2017 | Miller et al. |
| 9,636,224 B2 | 5/2017 | Zipory et al. |
| 9,662,209 B2 | 5/2017 | Gross et al. |
| 9,713,530 B2 | 7/2017 | Cabiri et al. |
| 9,724,192 B2 | 8/2017 | Sheps et al. |
| 9,730,793 B2 | 8/2017 | Reich et al. |
| 9,775,709 B2 | 10/2017 | Miller et al. |
| 9,814,572 B2 | 11/2017 | Edelman et al. |
| 9,872,769 B2 | 1/2018 | Gross et al. |
| 9,883,943 B2 | 2/2018 | Gross et al. |
| 9,918,840 B2 | 3/2018 | Reich et al. |
| 9,937,042 B2 | 4/2018 | Cabiri et al. |
| 9,949,828 B2 | 4/2018 | Sheps et al. |
| 9,968,452 B2 | 5/2018 | Sheps et al. |
| 9,968,454 B2 | 5/2018 | Reich et al. |
| 9,974,653 B2 | 5/2018 | Gross et al. |
| 10,028,832 B2 | 7/2018 | Quill et al. |
| 10,098,737 B2 | 10/2018 | Miller |
| 10,123,874 B2 | 11/2018 | Khairkhahan et al. |
| 10,130,472 B2 | 11/2018 | O'beirne et al. |
| 10,166,098 B2 | 1/2019 | Khairkhahan et al. |
| 10,195,030 B2 | 2/2019 | Gross et al. |
| 10,226,342 B2 | 3/2019 | Kutzik et al. |
| 10,251,635 B2 | 4/2019 | Khairkhahan et al. |
| 10,265,170 B2 | 4/2019 | Zipory et al. |
| 10,299,793 B2 | 5/2019 | Zipory et al. |
| 10,350,068 B2 | 7/2019 | Miller et al. |
| 10,357,366 B2 | 7/2019 | Gross et al. |
| 10,363,136 B2 | 7/2019 | Miller et al. |
| 10,363,137 B2 | 7/2019 | Gross et al. |
| 10,368,982 B2 | 8/2019 | Weber et al. |
| 10,376,266 B2 | 8/2019 | Herman et al. |
| 10,376,365 B2 | 8/2019 | Khairkhahan et al. |
| 10,383,726 B2 | 8/2019 | Kramer |
| 10,426,619 B2 | 10/2019 | Mohl |
| 10,433,955 B2 | 10/2019 | Edelman et al. |
| 10,449,046 B2 | 10/2019 | Rafiee |
| 10,449,049 B2 | 10/2019 | Li et al. |
| 10,449,333 B2 | 10/2019 | Hammer et al. |
| 10,470,882 B2 | 11/2019 | Gross et al. |
| 10,470,883 B2 | 11/2019 | Khairkhahan et al. |
| 10,478,303 B2 | 11/2019 | Khairkhahan et al. |
| 10,492,909 B2 | 12/2019 | Miller et al. |
| 10,500,048 B2 | 12/2019 | Khairkhahan et al. |
| 10,512,542 B2 | 12/2019 | Khairkhahan et al. |
| 10,517,719 B2 | 12/2019 | Miller et al. |
| 10,543,088 B2 | 1/2020 | Lashinski |
| 10,548,729 B2 | 2/2020 | Zipory et al. |
| 10,548,731 B2 | 2/2020 | Lashinski et al. |
| 10,561,498 B2 | 2/2020 | Gross et al. |
| 10,568,738 B2 | 2/2020 | Sheps et al. |
| 10,583,009 B2 | 3/2020 | Hauser et al. |
| 10,610,360 B2 | 4/2020 | Reich et al. |
| 10,653,524 B2 | 5/2020 | Khairkhahan et al. |
| 10,702,386 B2 | 7/2020 | Khairkhahan et al. |
| 10,751,180 B2 | 8/2020 | Schewel |
| 11,000,372 B2 | 5/2021 | Khairkhahan et al. |
| 11,026,791 B2 | 6/2021 | Genovese et al. |
| 11,076,957 B2 | 8/2021 | Mohl |
| 11,160,656 B2 | 11/2021 | Khairkhahan |
| 11,298,229 B2 | 4/2022 | Khairkhahan |
| 11,413,145 B2 | 8/2022 | Khairkhahan |
| 11,419,719 B2 | 8/2022 | Schewel et al. |
| 11,419,722 B2 | 8/2022 | Khairkhahan et al. |
| 11,426,279 B2 | 8/2022 | Khairkhahan et al. |
| 11,432,928 B2 | 9/2022 | Mohl |
| 11,464,634 B2 | 10/2022 | Khairkhahan et al. |
| 11,497,606 B2 | 11/2022 | Khairkhahan et al. |
| 11,504,237 B2 | 11/2022 | Gifford et al. |
| 11,534,302 B2 | 12/2022 | Khairkhahan et al. |
| 11,571,305 B2 | 2/2023 | Padala et al. |
| 11,622,759 B2 | 4/2023 | Khairkhahan et al. |
| 11,633,281 B2 | 4/2023 | Kappetein et al. |
| 11,648,119 B2 | 5/2023 | Khairkhahan et al. |
| 11,648,120 B2 | 5/2023 | Khairkhahan et al. |
| 11,672,659 B2 | 6/2023 | Khairkhahan et al. |
| 11,672,660 B2 | 6/2023 | Moh et al. |
| 11,678,986 B2 | 6/2023 | Khairkhahan et al. |
| 11,701,228 B2 | 7/2023 | Genovese et al. |
| 11,759,321 B2 | 9/2023 | Khairkhahan et al. |
| 11,883,291 B2 | 1/2024 | Gifford et al. |
| 11,974,921 B2 | 5/2024 | Khairkhahan et al. |
| 12,053,373 B2 | 8/2024 | McLean et al. |
| 12,109,116 B2 | 10/2024 | Khairkhahan et al. |
| 2001/0007956 A1 | 7/2001 | Letac et al. |
| 2001/0021872 A1 | 9/2001 | Bailey et al. |
| 2002/0029080 A1 | 3/2002 | Mortier et al. |
| 2002/0058995 A1 | 5/2002 | Stevens |
| 2002/0116024 A1 | 8/2002 | Goldberg et al. |
| 2002/0138135 A1 | 9/2002 | Duerig |
| 2002/0188301 A1 | 12/2002 | Dallara et al. |
| 2003/0023248 A1 | 1/2003 | Parodi |
| 2003/0100943 A1 | 5/2003 | Bolduc |
| 2003/0105474 A1 | 6/2003 | Bonutti |
| 2003/0135263 A1 | 7/2003 | Rourke et al. |
| 2003/0191497 A1 | 10/2003 | Cope |
| 2003/0199975 A1* | 10/2003 | Gabbay ............... A61F 2/2454 623/1.14 |
| 2004/0082956 A1 | 4/2004 | Baldwin et al. |
| 2004/0088047 A1 | 5/2004 | Spence et al. |
| 2004/0143323 A1 | 7/2004 | Chawla |
| 2004/0172046 A1 | 9/2004 | Hlavka et al. |
| 2004/0193217 A1 | 9/2004 | Lubbers et al. |
| 2004/0210307 A1 | 10/2004 | Khairkhahan |
| 2005/0004665 A1 | 1/2005 | Aklog |
| 2005/0004668 A1 | 1/2005 | Aklog et al. |
| 2005/0010287 A1 | 1/2005 | Macoviak et al. |
| 2005/0075727 A1 | 4/2005 | Wheatley et al. |
| 2005/0096740 A1 | 5/2005 | Langberg et al. |
| 2005/0107871 A1 | 5/2005 | Realyvasquez |
| 2005/0159810 A1 | 7/2005 | Filsoufi |
| 2005/0177180 A1 | 8/2005 | Kaganov et al. |
| 2005/0228495 A1 | 10/2005 | Macoviak |
| 2005/0261708 A1 | 11/2005 | Pasricha et al. |
| 2005/0267573 A9 | 12/2005 | Macoviak et al. |
| 2005/0283232 A1 | 12/2005 | Gabbay |
| 2006/0030885 A1 | 2/2006 | Hyde |
| 2006/0058871 A1 | 3/2006 | Zakay et al. |
| 2006/0122608 A1 | 6/2006 | Fallin et al. |
| 2006/0149368 A1 | 7/2006 | Spence |
| 2006/0190030 A1 | 8/2006 | To et al. |
| 2006/0252984 A1 | 11/2006 | Rahdert et al. |
| 2007/0005069 A1 | 1/2007 | Contiliano et al. |
| 2007/0049942 A1 | 3/2007 | Hindrichs et al. |

(56) References Cited

U.S. PATENT DOCUMENTS

| | | |
|---|---|---|
| 2007/0049970 A1 | 3/2007 | Belef et al. |
| 2007/0093890 A1 | 4/2007 | Eliasen et al. |
| 2007/0112352 A1 | 5/2007 | Sorensen et al. |
| 2007/0112425 A1 | 5/2007 | Schaller et al. |
| 2007/0118151 A1 | 5/2007 | Davidson |
| 2007/0129758 A1 | 6/2007 | Saadat |
| 2007/0185571 A1 | 8/2007 | Kapadia et al. |
| 2007/0233239 A1 | 10/2007 | Navia et al. |
| 2007/0239272 A1 | 10/2007 | Navia et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0250160 A1 | 10/2007 | Rafiee |
| 2007/0255399 A1 | 11/2007 | Eliasen et al. |
| 2007/0265658 A1 | 11/2007 | Nelson et al. |
| 2007/0265700 A1 | 11/2007 | Eliasen et al. |
| 2007/0265702 A1 | 11/2007 | Lattouf |
| 2007/0282375 A1 | 12/2007 | Hindrichs et al. |
| 2007/0293943 A1 | 12/2007 | Quinn |
| 2008/0065204 A1 | 3/2008 | Macoviak et al. |
| 2008/0109075 A1 | 5/2008 | Keranen |
| 2008/0125860 A1 | 5/2008 | Webler et al. |
| 2008/0125861 A1 | 5/2008 | Webler et al. |
| 2008/0195205 A1 | 8/2008 | Schwartz |
| 2008/0262609 A1* | 10/2008 | Gross ............... A61F 2/2445 623/2.38 |
| 2008/0319541 A1 | 12/2008 | Filsoufi |
| 2009/0012354 A1 | 1/2009 | Wood |
| 2009/0088836 A1 | 4/2009 | Bishop et al. |
| 2009/0177277 A1 | 7/2009 | Milo |
| 2009/0234404 A1 | 9/2009 | Fitzgerald et al. |
| 2009/0259304 A1 | 10/2009 | O'Beirne et al. |
| 2009/0259307 A1 | 10/2009 | Gross et al. |
| 2009/0287304 A1 | 11/2009 | Dahlgren et al. |
| 2009/0326648 A1 | 12/2009 | Machold et al. |
| 2010/0010538 A1 | 1/2010 | Juravic et al. |
| 2010/0069954 A1 | 3/2010 | Blaeser et al. |
| 2010/0121435 A1 | 5/2010 | Subramanian et al. |
| 2010/0121437 A1 | 5/2010 | Subramanian et al. |
| 2010/0131057 A1 | 5/2010 | Subramanian et al. |
| 2010/0161043 A1 | 6/2010 | Maisano et al. |
| 2010/0161047 A1 | 6/2010 | Cabiri et al. |
| 2010/0249947 A1 | 9/2010 | Lesh et al. |
| 2010/0262233 A1 | 10/2010 | He |
| 2010/0280603 A1 | 11/2010 | Maisano et al. |
| 2010/0280604 A1 | 11/2010 | Zipory et al. |
| 2010/0280605 A1 | 11/2010 | Hammer |
| 2010/0280606 A1 | 11/2010 | Naor |
| 2010/0286767 A1 | 11/2010 | Zipory et al. |
| 2010/0298929 A1 | 11/2010 | Thornton et al. |
| 2010/0312333 A1 | 12/2010 | Navia et al. |
| 2011/0004299 A1 | 1/2011 | Navia et al. |
| 2011/0082538 A1 | 4/2011 | Dahlgren et al. |
| 2011/0106245 A1 | 5/2011 | Miller et al. |
| 2011/0106247 A1 | 5/2011 | Miller et al. |
| 2011/0137397 A1 | 6/2011 | Chau et al. |
| 2011/0166649 A1 | 7/2011 | Gross et al. |
| 2011/0184510 A1 | 7/2011 | Maisano et al. |
| 2011/0224785 A1 | 9/2011 | Hacohen |
| 2011/0238088 A1 | 9/2011 | Bolduc et al. |
| 2011/0282361 A1 | 11/2011 | Miller |
| 2011/0288635 A1 | 11/2011 | Miller et al. |
| 2011/0301698 A1 | 12/2011 | Miller et al. |
| 2011/0319989 A1 | 12/2011 | Lane et al. |
| 2011/0319990 A1 | 12/2011 | Macoviak et al. |
| 2012/0016468 A1 | 1/2012 | Robin et al. |
| 2012/0022557 A1 | 1/2012 | Cabiri et al. |
| 2012/0022644 A1 | 1/2012 | Reich et al. |
| 2012/0078360 A1 | 3/2012 | Rafiee |
| 2012/0136436 A1 | 5/2012 | Cabiri et al. |
| 2012/0165930 A1 | 6/2012 | Gifford et al. |
| 2012/0197388 A1* | 8/2012 | Khairkhahan ..... A61B 17/0401 623/2.11 |
| 2012/0203336 A1 | 8/2012 | Annest |
| 2012/0245604 A1 | 9/2012 | Tegzes |
| 2012/0283757 A1 | 11/2012 | Miller et al. |
| 2012/0323316 A1 | 12/2012 | Chau et al. |
| 2012/0330410 A1 | 12/2012 | Hammer et al. |
| 2012/0330411 A1 | 12/2012 | Gross et al. |
| 2013/0023985 A1 | 1/2013 | Khairkhahan et al. |
| 2013/0096672 A1 | 4/2013 | Reich et al. |
| 2013/0116776 A1 | 5/2013 | Gross et al. |
| 2013/0116780 A1 | 5/2013 | Miller et al. |
| 2013/0131792 A1 | 5/2013 | Miller et al. |
| 2013/0190861 A1 | 7/2013 | Chau et al. |
| 2013/0190866 A1 | 7/2013 | Zipory et al. |
| 2013/0238024 A1 | 9/2013 | Taylor et al. |
| 2013/0282028 A1 | 10/2013 | Conklin et al. |
| 2013/0325110 A1 | 12/2013 | Khalil et al. |
| 2013/0338763 A1 | 12/2013 | Rowe et al. |
| 2014/0018906 A1 | 1/2014 | Rafiee |
| 2014/0025163 A1 | 1/2014 | Padala et al. |
| 2014/0039615 A1 | 2/2014 | Padala et al. |
| 2014/0067048 A1 | 3/2014 | Chau |
| 2014/0067054 A1 | 3/2014 | Chau et al. |
| 2014/0094903 A1 | 4/2014 | Miller et al. |
| 2014/0128965 A1 | 5/2014 | Rafiee |
| 2014/0142695 A1 | 5/2014 | Gross et al. |
| 2014/0148898 A1 | 5/2014 | Gross et al. |
| 2014/0222137 A1 | 8/2014 | Miller et al. |
| 2014/0243963 A1 | 8/2014 | Sheps et al. |
| 2014/0276648 A1 | 9/2014 | Hammer et al. |
| 2014/0277088 A1 | 9/2014 | Friedman |
| 2014/0309661 A1 | 10/2014 | Sheps et al. |
| 2014/0343668 A1 | 11/2014 | Zipory et al. |
| 2014/0358223 A1 | 12/2014 | Rafiee et al. |
| 2014/0379075 A1 | 12/2014 | Maurer et al. |
| 2015/0012087 A1 | 1/2015 | Miller et al. |
| 2015/0039083 A1 | 2/2015 | Rafiee et al. |
| 2015/0057682 A1 | 2/2015 | Kovach |
| 2015/0081014 A1 | 3/2015 | Gross et al. |
| 2015/0100116 A1 | 4/2015 | Mohl et al. |
| 2015/0105855 A1 | 4/2015 | Cabiri et al. |
| 2015/0112429 A1 | 4/2015 | Khairkhahan et al. |
| 2015/0112432 A1 | 4/2015 | Reich et al. |
| 2015/0119981 A1 | 4/2015 | Khairkhahan et al. |
| 2015/0164637 A1 | 6/2015 | Khairkhahan et al. |
| 2015/0182336 A1 | 7/2015 | Zipory et al. |
| 2015/0202043 A1 | 7/2015 | Zakai et al. |
| 2015/0230924 A1 | 8/2015 | Miller et al. |
| 2015/0257877 A1 | 9/2015 | Hernandez |
| 2015/0272586 A1 | 10/2015 | Herman et al. |
| 2015/0272734 A1 | 10/2015 | Sheps et al. |
| 2015/0297212 A1 | 10/2015 | Reich et al. |
| 2015/0366556 A1 | 12/2015 | Khairkhahan et al. |
| 2015/0366666 A1 | 12/2015 | Khairkhahan et al. |
| 2016/0008132 A1 | 1/2016 | Cabiri et al. |
| 2016/0030176 A1 | 2/2016 | Mohl et al. |
| 2016/0058557 A1 | 3/2016 | Reich et al. |
| 2016/0074164 A1 | 3/2016 | Naor |
| 2016/0089233 A1 | 3/2016 | Lee et al. |
| 2016/0106437 A1 | 4/2016 | van der Burg et al. |
| 2016/0113767 A1 | 4/2016 | Miller et al. |
| 2016/0157862 A1 | 6/2016 | Hernandez et al. |
| 2016/0158008 A1 | 6/2016 | Miller et al. |
| 2016/0262755 A1 | 9/2016 | Zipory et al. |
| 2016/0324639 A1 | 11/2016 | Nguyen et al. |
| 2016/0331523 A1 | 11/2016 | Chau et al. |
| 2016/0361168 A1 | 12/2016 | Gross et al. |
| 2016/0361169 A1 | 12/2016 | Gross et al. |
| 2017/0000609 A1 | 1/2017 | Gross et al. |
| 2017/0086975 A1 | 3/2017 | Gilmore et al. |
| 2017/0100249 A1 | 4/2017 | Miller et al. |
| 2017/0105839 A1 | 4/2017 | Subramanian et al. |
| 2017/0112618 A1 | 4/2017 | Li et al. |
| 2017/0135815 A1 | 5/2017 | Gross et al. |
| 2017/0135816 A1 | 5/2017 | Lashinski et al. |
| 2017/0189186 A1 | 7/2017 | Mohl |
| 2017/0196691 A1 | 7/2017 | Zipory et al. |
| 2017/0209270 A1 | 7/2017 | Miller et al. |
| 2017/0245993 A1 | 8/2017 | Gross et al. |
| 2017/0245994 A1 | 8/2017 | Khairkhahan et al. |
| 2017/0258588 A1 | 9/2017 | Zipory et al. |
| 2017/0258590 A1 | 9/2017 | Khairkhahan et al. |

(56) References Cited

U.S. PATENT DOCUMENTS

| | | |
|---|---|---|
| 2017/0265995 A1 | 9/2017 | Khairkhahan et al. |
| 2017/0296340 A1 | 10/2017 | Gross et al. |
| 2017/0325958 A1 | 11/2017 | Reich et al. |
| 2017/0325959 A1 | 11/2017 | Sheps et al. |
| 2017/0354500 A1 | 12/2017 | Martinez et al. |
| 2017/0367825 A1 | 12/2017 | Cabiri et al. |
| 2018/0008409 A1 | 1/2018 | Kutzik et al. |
| 2018/0014933 A1 | 1/2018 | Miller et al. |
| 2018/0014934 A1 | 1/2018 | Miller et al. |
| 2018/0049875 A1 | 2/2018 | Iflah et al. |
| 2018/0116797 A9 | 5/2018 | Miller et al. |
| 2018/0125657 A1 | 5/2018 | Dahlgren et al. |
| 2018/0228608 A1 | 8/2018 | Sheps et al. |
| 2018/0250133 A1 | 9/2018 | Reich et al. |
| 2018/0256318 A1 | 9/2018 | Khairkhahan |
| 2018/0256333 A1 | 9/2018 | Cabiri et al. |
| 2018/0256334 A1 | 9/2018 | Sheps et al. |
| 2018/0256865 A1 | 9/2018 | Finch et al. |
| 2018/0263776 A1 | 9/2018 | Gross et al. |
| 2018/0263777 A1 | 9/2018 | Gross et al. |
| 2018/0318080 A1 | 11/2018 | Quill et al. |
| 2018/0325670 A1 | 11/2018 | De Canniere |
| 2019/0008641 A1 | 1/2019 | Dahlgren et al. |
| 2019/0046318 A1 | 2/2019 | Miller et al. |
| 2019/0070004 A1 | 3/2019 | Ifah et al. |
| 2019/0076247 A1 | 3/2019 | Zeng |
| 2019/0076249 A1 | 3/2019 | Khairkhahan |
| 2019/0125325 A1 | 5/2019 | Sheps et al. |
| 2019/0133586 A1 | 5/2019 | Zipory et al. |
| 2019/0151090 A1 | 5/2019 | Gross et al. |
| 2019/0151093 A1 | 5/2019 | Keidar et al. |
| 2019/0159898 A1 | 5/2019 | Kutzik et al. |
| 2019/0167425 A1 | 6/2019 | Reich et al. |
| 2019/0175344 A1 | 6/2019 | Khairkhahan |
| 2019/0183644 A1 | 6/2019 | Hacohen |
| 2019/0201191 A1 | 7/2019 | McLean et al. |
| 2019/0216600 A1 | 7/2019 | Zipory et al. |
| 2019/0254821 A1 | 8/2019 | Rafiee et al. |
| 2019/0269512 A9 | 9/2019 | Lashinski |
| 2019/0269513 A9 | 9/2019 | Cabiri et al. |
| 2019/0274830 A1 | 9/2019 | Miller et al. |
| 2019/0282358 A1 | 9/2019 | Khairkhahan et al. |
| 2019/0282364 A1 | 9/2019 | Khairkhahan et al. |
| 2019/0290431 A1 | 9/2019 | Genovese et al. |
| 2019/0298332 A1 | 10/2019 | Khairkhahan et al. |
| 2019/0298522 A1 | 10/2019 | Subramanian et al. |
| 2019/0321049 A1 | 10/2019 | Herman et al. |
| 2019/0336288 A1 | 11/2019 | Gross et al. |
| 2019/0336289 A1 | 11/2019 | Miller et al. |
| 2019/0350703 A1 | 11/2019 | Weber et al. |
| 2019/0350705 A1 | 11/2019 | Schewel et al. |
| 2019/0374343 A1 | 12/2019 | Lashinski et al. |
| 2019/0374750 A1 | 12/2019 | Hammer et al. |
| 2019/0380834 A1 | 12/2019 | Rafiee |
| 2020/0015971 A1 | 1/2020 | Brauon et al. |
| 2020/0030097 A1 | 1/2020 | Khairkhahan et al. |
| 2020/0038186 A1 | 2/2020 | Gross et al. |
| 2020/0100899 A1 | 4/2020 | Miller et al. |
| 2020/0113685 A1 | 4/2020 | Miller et al. |
| 2020/0205966 A1 | 7/2020 | Khairkhahan et al. |
| 2020/0205975 A1 | 7/2020 | Khairkhahan |
| 2020/0205978 A1 | 7/2020 | Padala et al. |
| 2020/0205980 A1 | 7/2020 | Khairkhahan et al. |
| 2020/0214841 A1 | 7/2020 | Khairkhahan et al. |
| 2020/0222185 A1 | 7/2020 | Kappetein et al. |
| 2020/0275974 A1 | 9/2020 | Gifford et al. |
| 2020/0289265 A1 | 9/2020 | Gifford et al. |
| 2020/0330229 A1 | 10/2020 | Serraf et al. |
| 2020/0337843 A1 | 10/2020 | Khairkhahan et al. |
| 2020/0383776 A1 | 12/2020 | Schewel |
| 2020/0397567 A1 | 12/2020 | Khairkhahan et al. |
| 2021/0085462 A1 | 3/2021 | Gifford et al. |
| 2021/0196462 A1 | 7/2021 | Khairkhahan |
| 2021/0290390 A1 | 9/2021 | Genovese et al. |
| 2021/0298901 A1 | 9/2021 | Khairkhahan et al. |
| 2021/0346159 A1 | 11/2021 | Keränen |
| 2021/0353418 A1 | 11/2021 | Mohl |
| 2022/0000621 A1 | 1/2022 | Gifford et al. |
| 2022/0039944 A1 | 2/2022 | Khairkhahan |
| 2022/0039951 A1 | 2/2022 | Khairkhahan |
| 2022/0054269 A1 | 2/2022 | Khairkhahan |
| 2022/0079753 A1 | 3/2022 | Zimmerman et al. |
| 2022/0079755 A1 | 3/2022 | Zimmerman et al. |
| 2022/0096234 A1 | 3/2022 | Sorajja |
| 2022/0096236 A1 | 3/2022 | Guidotti et al. |
| 2022/0160499 A1 | 5/2022 | Miyashiro et al. |
| 2022/0160508 A1 | 5/2022 | Miyashiro et al. |
| 2022/0183837 A1 | 6/2022 | Tuval et al. |
| 2022/0183839 A1 | 6/2022 | Khairkhahan |
| 2022/0192822 A1 | 6/2022 | McLean et al. |
| 2022/0125579 A1 | 7/2022 | McLean et al. |
| 2022/0233311 A1 | 7/2022 | Khairkhahan |
| 2022/0273433 A1 | 8/2022 | Schewel et al. |
| 2022/0296368 A1 | 9/2022 | Tuval et al. |
| 2022/0354637 A1 | 11/2022 | Khairkhahan |
| 2022/0354647 A1 | 11/2022 | Khairkhahan |
| 2022/0354648 A1 | 11/2022 | Khairkhahan |
| 2022/0362012 A1 | 11/2022 | Khairkhahan |
| 2022/0409372 A1 | 12/2022 | Khairkhahan |
| 2023/0040410 A1 | 2/2023 | Khairkhahan |
| 2023/0105858 A1 | 4/2023 | Khalil et al. |
| 2023/0107129 A1 | 4/2023 | Mohl |
| 2023/0132907 A1 | 5/2023 | McLean et al. |
| 2023/0138388 A1 | 5/2023 | Padala et al. |
| 2023/0142064 A1 | 5/2023 | Chau et al. |
| 2023/0147741 A1 | 5/2023 | Khairkhahan |
| 2023/0181313 A1 | 6/2023 | Mohl et al. |
| 2023/0248518 A1 | 8/2023 | Khairkhahan |
| 2023/0270549 A1 | 8/2023 | Guidotti et al. |
| 2023/0277169 A1 | 9/2023 | Khairkhahan |
| 2023/0293298 A1 | 9/2023 | Khairkhahan |
| 2023/0293299 A1 | 9/2023 | Khairkhahan |
| 2023/0329865 A1 | 10/2023 | Kappetein et al. |
| 2023/0404757 A1 | 12/2023 | Khairkhahan |
| 2024/0016473 A1 | 1/2024 | Schewel et al. |
| 2024/0033083 A1 | 2/2024 | Khairkhahan |
| 2024/0041601 A1 | 2/2024 | Khairkhahan et al. |
| 2024/0341957 A1 | 10/2024 | Khairkhahan et al. |
| 2025/0041061 A1 | 2/2025 | Khairkhahan et al. |

FOREIGN PATENT DOCUMENTS

| | | |
|---|---|---|
| CN | 101056596 | 10/2007 |
| CN | 101068508 | 11/2007 |
| CN | 101947146 | 1/2011 |
| CN | 102065777 | 5/2011 |
| CN | 102458309 | 5/2012 |
| CN | 102665612 | 9/2012 |
| CN | 102781790 | 11/2012 |
| CN | 102933175 | 2/2013 |
| CN | 202821715 | 3/2013 |
| CN | 103118602 | 5/2013 |
| CN | 103338726 | 10/2013 |
| CN | 102905648 | 1/2015 |
| CN | 104394803 | 3/2015 |
| CN | 104582637 | 4/2015 |
| CN | 105287050 | 2/2016 |
| CN | 105451688 | 3/2016 |
| EP | 1 294 310 | 3/2003 |
| EP | 1 959 865 | 8/2008 |
| EP | 2 410 948 | 2/2012 |
| EP | 1 796 597 | 1/2013 |
| EP | 2 661 239 | 11/2013 |
| EP | 2 667 824 | 12/2013 |
| EP | 2 995 279 | 3/2016 |
| EP | 3 160 396 | 5/2017 |
| EP | 3 167 846 | 5/2017 |
| EP | 3 372 198 | 9/2018 |
| EP | 3 658 075 | 6/2020 |
| EP | 3 768 195 | 1/2021 |
| EP | 3 852 681 | 7/2021 |
| EP | 3 880 124 | 9/2021 |
| EP | 3 911 272 | 11/2021 |
| EP | 3 912 595 | 11/2021 |

(56) References Cited

FOREIGN PATENT DOCUMENTS

| | | |
|---|---|---|
| EP | 4 171 443 | 5/2023 |
| JP | S54-088693 | 7/1979 |
| JP | 2005-535384 | 11/2005 |
| JP | 2006-528911 | 12/2006 |
| JP | 2007-518492 | 7/2007 |
| JP | 2008-517672 | 5/2008 |
| JP | 2010-511469 | 4/2010 |
| JP | 2012-511402 | 5/2012 |
| JP | 2012-520716 | 9/2012 |
| JP | 2014-510563 | 5/2014 |
| JP | 2014-231015 | 12/2014 |
| JP | 2015-523898 | 8/2016 |
| JP | 2017-18675 | 1/2017 |
| JP | 2020-127779 | 8/2020 |
| WO | WO 97/007744 | 3/1997 |
| WO | WO 99/53869 | 10/1998 |
| WO | WO 2004/014258 | 2/2004 |
| WO | WO 2004/100803 | 11/2004 |
| WO | WO 2004/103162 | 12/2004 |
| WO | WO 2005/069875 | 8/2005 |
| WO | WO 2006/032051 | 3/2006 |
| WO | WO 2006/041877 | 4/2006 |
| WO | WO 2006/086434 | 8/2006 |
| WO | WO 2007/062054 | 5/2007 |
| WO | WO 2007/135101 | 11/2007 |
| WO | WO 2007/140470 | 12/2007 |
| WO | WO 2008/068756 | 6/2008 |
| WO | WO 2008/141322 | 11/2008 |
| WO | WO 2010/106438 | 9/2010 |
| WO | WO 2011/037891 | 3/2011 |
| WO | WO 2011/047168 | 4/2011 |
| WO | WO 2012/061809 | 5/2012 |
| WO | WO 2012/092437 | 7/2012 |
| WO | WO 2012/102928 | 8/2012 |
| WO | WO 2013/059747 | 4/2013 |
| WO | WO 2013/131069 | 9/2013 |
| WO | WO 2013/173587 | 11/2013 |
| WO | WO 2013/178335 | 12/2013 |
| WO | WO 2013/192107 | 12/2013 |
| WO | WO 2014/181336 | 11/2014 |
| WO | WO 2014/207575 | 12/2014 |
| WO | WO 2015/020971 | 2/2015 |
| WO | WO 2015/052570 | 4/2015 |
| WO | WO 2015/061533 | 4/2015 |
| WO | WO 2015/195823 | 12/2015 |
| WO | WO 2015/200497 | 12/2015 |
| WO | WO 2016/059639 | 4/2016 |
| WO | WO 2016/178136 | 11/2016 |
| WO | WO 2016/183485 | 11/2016 |
| WO | WO 2017/079279 | 5/2017 |
| WO | WO 2017/136596 | 8/2017 |
| WO | WO 2018/169878 | 9/2018 |
| WO | WO 2018/169878 A1 | 9/2018 |
| WO | WO 2019/116322 | 6/2019 |
| WO | WO 2019/222694 | 11/2019 |
| WO | WO 2019/241777 | 12/2019 |
| WO | WO 2020/055811 | 3/2020 |
| WO | WO 2021/055983 | 3/2021 |
| WO | WO 2022/006087 | 1/2022 |
| WO | WO 2022/018494 | 1/2022 |
| WO | WO 2023/105334 | 6/2023 |
| WO | WO 2023/114289 | 6/2023 |
| WO | WO 2023/218127 | 11/2023 |

OTHER PUBLICATIONS

Office Action for JP 2021-153169 dated Dec. 26, 2022.
Office Action for CA 2,958,065 dated Nov. 18, 2022.
Office Action for JP 2021-176431 dated Jan. 6, 2023.
Office Action for 2020-041944 dated Feb. 13, 2023.
Office Action for CN 202010539957.9 dated Mar. 22, 2023.
Extended European Search Report, EP 22214458, dated Mar. 24, 2023.
Office Action for CA 3,004,418 dated Dec. 13, 2022.
Office Action for 2021-513859 dated Jun. 14, 2023.
Office Action for JP 2021-153169 dated Jul. 3, 2023.
Office Action for CA 2,934,182 dated Jun. 30, 2021.
Office Action for CA 2,958,065 dated Jul. 9, 2021.
Office Action for JP 2018-543021 dated Oct. 4, 2021.
Office Action for JP 2020-085273 dated Aug. 23, 2021.
Office Action for JP 2020-082001 dated Nov. 29, 2021.
Office Action for CA 2,934, 182 dated Mar. 2, 2022.
Office Action for CA 2,958,065 dated Mar. 2, 2022.
Office Action for 2020-041944 dated Feb. 21, 2022.
Office Action for 2019-572351 dated Feb. 28, 2022.
International Search Report for Application No. PCT/US2021/016248 dated Mar. 29, 2022 in 15 pages.
Extended European Search Report, EP 19860754.1 dated Jun. 1, 2022.
International Search Report for Application No. PCT/US2022/071235 dated Jun. 27, 2022 in 13 pages.
Office Action for 2020-041944 dated Jul. 22, 2022.
Office Action for 2019-572351 dated Sep. 12, 2022.
Office Action for CN 202010539957.9 dated Nov. 3, 2022.
Biocina et al., Mitral Valve Repair With the New Mitrofast® Repair System, Dubrava University Hospital, Zagreb, Crotia, Mitrofast Abstract European Soc CVS 55th Congress—May 11-14, 2006 Suppl 1 to vol. 5.
Biocina, The arteficial coaptation surface concept in mitral valve repair, University of Zagreb School of Medicine, Department of Cardiac Surgery, Savudrija Mitrofast 2010.
Chiam et al., Percutaneous Transcatheter Mitral Valve Repair, The American College of Cardiology Foundation, JACC: Cardiovascular Interventions, vol. 4 No. 1, Jan. 2011:1-13.
Jassar et al., Posterior Leaflet Augmentation in Ischemic Mitral Regurgitation IncreasesLeaflet Coaptation and Mobility, The Society of Thoracic Surgeons, Ann Thorac Surg 2012; 94:1438-45.
Langer et al., Posterior mitral leaflet extension: An adjunctive repair option for ischemic mitralregurgitation?, Surgery for Acquired Cardiovascular Disease, The Journal of Thoracic and Cardiovascular Surgery, Apr. 2006, downloaded Jun. 18, 2011.
Mohl et al., The Angel Valve Concept, Vienna University of Technology, Medical University of Vienna, Technology Offer, 1 page.
Mohl et al., An Innovative Concept For Transcatheter Treatment of Annular Dilatation and Restrictive Leaflet Motion in Mitral Insufficiency, Medical University of Vienna, 1 page.
Piemonte et al., Cardiovascular™: The Mitral Valve Spacer, Presented at Transcatheter Cardiovascular Therapeutics Conference—TCT Conference, Oct. 2008.
Rumel et al., The Correction of Mitral Insufficiency with a Trans-Valvular PolyvinylFormalinized Plastic (Ivalon) Sponge Prosthesis: A Preliminary Report, American College of Chest Physicians, 1958;33;401-413, Dec. 2, 2010.
International Preliminary Report on Patentability for PCT/US2012/021744 mailed Aug. 8, 2013 in 15 pages.
International Search Report for Application No. PCT/US2013/046173 dated Oct. 4, 2013 in 15 pages.
International Search Report for Application No. PCT/US2014/061901 dated Jan. 26, 2015 in 14 pages.
International Search Report for Application No. PCT/US2015/036260 dated Oct. 1, 2015 in 20 pages.
International Search Report for Application No. PCT/US2015/037451 dated Oct. 6, 2015 in 12 pages.
International Search Report for Application No. PCT/US2016/060094 dated Feb. 9, 2017 in 8 pages.
International Search Report for Application No. PCT/US2018/022043 dated Jun. 25, 2018 in 13 pages.
Extended European Search Report, EP 12738989.8, dated May 24, 2016.
Office Action for EP 12738989.8 dated Mar. 3, 2017.
Office Action for EP 12738989.8 dated Sep. 19, 2017.
Extended European Search Report, EP 13806272.4, dated Nov. 11, 2015.
Extended European Search Report, EP 14856738.1, dated Jun. 7, 2017.

(56) References Cited

OTHER PUBLICATIONS

Extended European Search Report, EP 15809346.8, dated Feb. 13, 2018.
Extended European Search Report, EP 15812032.9, dated Oct. 18, 2017.
Extended European Search Report, EP 16862864.2, dated May 10, 2019.
Office Action for CA 2,825,520 dated Nov. 27, 2017.
Office Action for CA 2,825,520 dated Aug. 21, 2018.
Office Action for CA 2,877,344 dated Mar. 12, 2019.
Office Action for CA 2,877,344 dated Oct. 9, 2019.
Office Action for CA 2,877,344 dated Jul. 21, 2020.
Office Action for CN 201280006673.7 dated Dec. 10, 2014.
Office Action for CN 201280006673.7 dated Sep. 22, 2015.
Office Action for CN 201280006673.7 dated Feb. 1, 2016.
Office Action for CN 201380044122.4 dated Nov. 4, 2015.
Office Action for CN 201380044122.4 dated Aug. 24, 2016.
Office Action for CN 201480070933.6 dated May 10, 2017.
Office Action for CN 201480070933.6 dated Dec. 25, 2017.
Office Action for CN 201580044329.0 dated Jan. 17, 2018.
Office Action for CN 201580044329.0 dated Jul. 29, 2019.
Office Action for CN 201580045375.2 dated Nov. 12, 2018.
Office Action for CN 201680077877.8 dated Aug. 15, 2019.
Office Action for JP 2013-552015 dated Dec. 7, 2015.
Office Action for JP 2013-552015 dated Oct. 7, 2016.
Office Action for JP 2013-552015 dated Jun. 5, 2017.
Office Action for JP 2015-518499 dated Feb. 27, 2017.
Office Action for JP 2015-518499 dated Aug. 31, 2017.
Office Action for JP 2015-518499 dated Aug. 20, 2018.
Office Action for JP 2016-525999 dated Jul. 9, 2018.
International Search Report for Application No. PCT/US2019/050331 dated Jan. 23, 2020 in 9 pages.
Office Action for CN 201580044329.0 dated Mar. 3, 2020.
Office Action for EP 15812032.9, dated Jul. 6, 2020.
Office Action for CA 2,877,344 dated Dec. 23, 2020.
Office Action for CA 2,934, 182 dated Dec. 9, 2020.
Extended European Search Report, EP 18768736.3, dated Oct. 9, 2020.
International Search Report for Application No. PCT/US2020/065261 dated Apr. 13, 2021 in 13 pages.
Office Action for CN 201880031519.2 dated May 19, 2021.
Office Action for EP 13806272.4, dated Mar. 23, 2021.
Office Action for EP 14856738.1, dated Apr. 23, 2021.
Extended European Search Report, EP 20910735.8, dated Jan. 8, 2024.
Office Action for JP 2021-176431 dated Jul. 24, 2023.
Summons to attend oral proceedings, EP 15809346.8, dated Jun. 7, 2023.
Office Action for JP 2022-164138 dated Jul. 31, 2023.
Opposition to EP 3370650 filed Sep. 21, 2023.
Lasala, John M., and Jason H. Rogers. Interventional Procedures for Adult Structural Heart Disease. Elsevier/Saunders, 2014.
Hill, Arthur C et al. "Novel mitral repair device for the treatment of severe mitral regurgitation: preclinical ovine acute and chronic implantation model." Innovations (Philadelphia, Pa.) vol. 9,6 (2014): 432-8. doi: 10.1177/155698451400900607.
Iaizzo, Paul A. Handbook of Cardiac Anatomy, Physiology, and Devices. United States, Humana Press, 2009.
Sonne, Carolin et al. "Age and body surface area dependency of mitral valve and papillary apparatus parameters: assessment by real-time three-dimensional echocardiography." European journal of echocardiography: the journal of the Working Group on Echocardiography of the European Society of Cardiology vol. 10,2 (2009): 287-94. doi: 10.1093/ejechocard/jen237.
Opposition to EP 3157469 filed Sep. 14, 2022.
Office Action for JP 2021-212699 dated Sep. 19, 2023.
Office Action for CN 201980059862.2 dated Nov. 29, 2023.
Office Action for JP 2023-039771 dated Dec. 4, 2023.
Office Action for JP 2020-085273 dated May 31, 2021.
Office Action for CN 201480070933.6 dated Aug. 10, 2018.
Office Action for CN 201480070933.6 dated Apr. 17, 2019.
Office Action for CN 201580045375.2 dated Mar. 29, 2018.
Office Action for EP 15812032.9, dated Oct. 10, 2019.
Office Action for JP 2016-525999 dated Jun. 27, 2019.
Office Action for JP 2016-525999 dated Mar. 16, 2020.
Office Action for 2016-573983 dated Apr. 1, 2019.
Office Action for 2016-573983 dated Nov. 11, 2019.
Office Action for JP 2016-574967 dated May 7, 2019.
Office Action for JP 2016-574967 dated Dec. 26, 2019.
Office Action for 2016-573983 dated May 11, 2020.
Office Action for CN 201580044329.0 dated Aug. 26, 2020.
Office Action for JP 2016-574967 dated Jun. 29, 2020.
Office Action for JP 2018-543021 dated Oct. 27, 2020.
Office Action for JP 2020-082001 dated Mar. 29, 2021.
Summons to Attend Oral Proceedings, EP 13806272.4, dated Feb. 9, 2024.
Office Action for JP 2021-212699 dated Mar. 18, 2024.
Office Action for JP 2022-164138 dated Mar. 18, 2024.
Office Action for 2021-513859 dated Mar. 18, 2024.
Interlocutory Decision EP 15809346.8, dated Mar. 19, 2024.
Office Action for CN 202110375324.3 dated Apr. 30, 2024.
Office Action for CA 3,056,420 dated Feb. 16, 2024.
International Search Report and Written Opinion for Application No. PCT/US2024/027244 dated Sep. 25, 2024 in 16 pages.
Office Action for EP19860754.1 dated May 29, 2024.
Office Action for 2023-213880 dated Jul. 16, 2024.
Invitation to Pay Additional Search Fees for PCT/US2024/027244 dated Jul. 30, 2024.
Office Action for JP 2023-039771 dated Aug. 13, 2024.
Office Action for JP 2022-537714 dated Oct. 21, 2024.
Office Action for CN 202111212597.2 dated Jan. 8, 2025.
Office Action for 2023-213880 dated Jan. 15, 2025.

* cited by examiner

SYSTEMS AND METHODS FOR TRANSCATHETER TREATMENT OF VALVE REGURGITATION

CROSS-REFERENCE TO RELATED APPLICATIONS

The present application is a continuation application of U.S. application Ser. No. 16/220,322 filed Dec. 14, 2018, which is a continuation application of U.S. application Ser. No. 14/313,975 filed Jun. 24, 2014, which claims priority under 35 U.S.C. § 119 (e) to U.S. Provisional Application No. 61/895,647, filed on Oct. 25, 2013. Each of the foregoing applications of which are hereby incorporated by reference in their entireties. Any and all applications for which a foreign or domestic priority claim is identified in the Application Data Sheet as filed with the present application, are hereby incorporated by reference in their entirety under 37 CFR 1.57.

BACKGROUND OF THE INVENTION

Field of the Invention

The present invention generally provides improved medical devices, systems, and methods, typically for treatment of heart valve disease and/or for altering characteristics of one or more valves of the body. Embodiments of the invention include implants for treatment of mitral valve regurgitation.

The human heart receives blood from the organs and tissues via the veins, pumps that blood through the lungs where the blood becomes enriched with oxygen, and propels the oxygenated blood out of the heart to the arteries so that the organ systems of the body can extract the oxygen for proper function. Deoxygenated blood flows back to the heart where it is once again pumped to the lungs.

The heart includes four chambers: the right atrium (RA), the right ventricle (RV), the left atrium (LA) and the left ventricle (LV). The pumping action of the left and right sides of the heart occurs generally in synchrony during the overall cardiac cycle.

The heart has four valves generally configured to selectively transmit blood flow in the correct direction during the cardiac cycle. The valves that separate the atria from the ventricles are referred to as the atrioventricular (or AV) valves. The AV valve between the left atrium and the left ventricle is the mitral valve. The AV valve between the right atrium and the right ventricle is the tricuspid valve. The pulmonary valve directs blood flow to the pulmonary artery and thence to the lungs; blood returns to the left atrium via the pulmonary veins. The aortic valve directs flow through the aorta and thence to the periphery. There are normally no direct connections between the ventricles or between the atria.

The mechanical heartbeat is triggered by an electrical impulse which spreads throughout the cardiac tissue. Opening and closing of heart valves may occur primarily as a result of pressure differences between chambers, those pressures resulting from either passive filling or chamber contraction. For example, the opening and closing of the mitral valve may occur as a result of the pressure differences between the left atrium and the left ventricle.

At the beginning of ventricular filling (diastole) the aortic and pulmonary valves are closed to prevent back flow from the arteries into the ventricles. Shortly thereafter, the AV valves open to allow unimpeded flow from the atria into the corresponding ventricles. Shortly after ventricular systole (i.e., ventricular emptying) begins, the tricuspid and mitral valves normally shut, forming a seal which prevents flow from the ventricles back into the corresponding atria.

Unfortunately, the AV valves may become damaged or may otherwise fail to function properly, resulting in improper closing. The AV valves are complex structures that generally include an annulus, leaflets, chordae and a support structure. Each atrium interfaces with its valve via an atrial vestibule. The mitral valve has two leaflets; the analogous structure of the tricuspid valve has three leaflets, and opposition or engagement of corresponding surfaces of leaflets against each other helps provide closure or sealing of the valve to prevent blood flowing in the wrong direction. Failure of the leaflets to seal during ventricular systole is known as malcoaptation, and may allow blood to flow backward through the valve (regurgitation). Heart valve regurgitation can have serious consequences to a patient, often resulting in cardiac failure, decreased blood flow, lower blood pressure, and/or a diminished flow of oxygen to the tissues of the body. Mitral regurgitation can also cause blood to flow back from the left atrium to the pulmonary veins, causing congestion. Severe valvular regurgitation, if untreated, can result in permanent disability or death.

DESCRIPTION OF THE RELATED ART

A variety of therapies have been applied for treatment of mitral valve regurgitation, and still other therapies may have been proposed but not yet actually used to treat patients. While several of the known therapies have been found to provide benefits for at least some patients, still further options would be desirable. For example, pharmacologic agents (such as diuretics and vasodilators) can be used with patients having mild mitral valve regurgitation to help reduce the amount of blood flowing back into the left atrium. However, medications can suffer from lack of patient compliance. A significant number of patients may occasionally (or even regularly) fail to take medications, despite the potential seriousness of chronic and/or progressively deteriorating mitral valve regurgitation. Pharmacological therapies of mitral valve regurgitation may also be inconvenient, are often ineffective (especially as the condition worsens), and can be associated with significant side effects (such as low blood pressure).

A variety of surgical options have also been proposed and/or employed for treatment of mitral valve regurgitation. For example, open-heart surgery can replace or repair a dysfunctional mitral valve. In annuloplasty ring repair, the posterior mitral annulus can be reduced in size along its circumference, optionally using sutures passed through a mechanical surgical annuloplasty sewing ring to provide coaptation. Open surgery might also seek to reshape the leaflets and/or otherwise modify the support structure. Regardless, open mitral valve surgery is generally a very invasive treatment carried out with the patient under general anesthesia while on a heart-lung machine and with the chest cut open. Complications can be common, and in light of the morbidity (and potentially mortality) of open-heart surgery, the timing becomes a challenge-sicker patients may be in greater need of the surgery, but less able to withstand the surgery. Successful open mitral valve surgical outcomes can also be quite dependent on surgical skill and experience.

Given the morbidity and mortality of open-heart surgery, innovators have sought less invasive surgical therapies. Procedures that are done with robots or through endoscopes are often still quite invasive, and can also be time consuming, expensive, and in at least some cases, quite dependent on the surgeon's skill. Imposing even less trauma on these sometimes frail patients would be desirable, as would be providing therapies that could be successfully implemented by a significant number of physicians using widely distributed skills. Toward that end, a number of purportedly less invasive technologies and approaches have been proposed. These include devices which seek to re-shape the mitral annulus from within the coronary sinus; devices that attempt to reshape the annulus by cinching either above to below the native annulus; devices to fuse the leaflets (imitating the Alfieri stitch); devices to re-shape the left ventricle, and the like.

Perhaps most widely known, a variety of mitral valve replacement implants have been developed, with these implants generally replacing (or displacing) the native leaflets and relying on surgically implanted structures to control the blood flow paths between the chambers of the heart. While these various approaches and tools have met with differing levels of acceptance, none has yet gained widespread recognition as an ideal therapy for most or all patients suffering from mitral valve regurgitation.

Because of the challenges and disadvantages of known minimally invasive mitral valve regurgitation therapies and implants, still further alternative treatments have been proposed. Some of the alternative proposals have called for an implanted structure to remain within the valve annulus throughout the heart beat cycle. One group of these proposals includes a cylindrical balloon or the like to remain implanted on a tether or rigid rod extending between the atrium and the ventricle through the valve opening. Another group relies on an arcuate ring structure or the like, often in combination with a buttress or structural cross-member extending across the valve so as to anchor the implant. Unfortunately, sealing between the native leaflets and the full perimeter of a balloon or other coaxial body may prove challenging, while the significant contraction around the native valve annulus during each heart beat may result in significant fatigue failure issues during long-term implantation if a buttress or anchor interconnecting cross member is allowed to flex. Moreover, the significant movement of the tissues of the valve may make accurate positioning of the implant challenging regardless of whether the implant is rigid or flexible.

In light of the above, it would be desirable to provide improved medical devices, systems, and methods. It would be particularly desirable to provide new techniques for treatment of mitral valve regurgitation and other heart valve diseases, and/or for altering characteristics of one or more of the other valves of the body. The need remains for a device which can directly enhance leaflet coaptation (rather than indirectly via annular or ventricular re-shaping) and which does not disrupt leaflet anatomy via fusion or otherwise, but which can be deployed simply and reliably, and without excessive cost or surgical time. It would be particularly beneficial if these new techniques could be implemented using a less-invasive approach, without stopping the heart or relying on a heart-lung machine for deployment, and without relying on exceptional skills of the surgeon to provide improved valve and/or heart function.

SUMMARY OF THE INVENTION

The invention generally provides improved medical devices, systems, and methods. In some embodiments, the invention provides new implants, implant systems, and methods for treatment of mitral valve regurgitation and other valve diseases. In some embodiments, the implants comprise a coaptation assist body which remains within the blood flow path as the valve moves back and forth between an open-valve configuration and a closed valve configuration. The coaptation assist body may extend laterally across some, most, or all of the width of the valve opening, allowing coaptation between at least one of the native leaflets and the implant body. In some embodiments, also disclosed is an implant, which can be a cardiac implant, such as a coaptation assist body, cardiac patch, replacement heart valve, annuloplasty ring, pacemaker, sensor, or other device. At least one ribbon (e.g., clip) can be configured to extend from the implant body. The ribbon can be made of a shape memory material having a preformed shape with at least one curve. The ribbon can be movable from a first compressed configuration to a second expanded configuration. The ribbon can be configured to provide a force, such as a compressive force to clip to a body structure, such as an intracardiac structure. In some embodiments, the intracardiac structure is a single native valve leaflet, and the force is applied between a first surface of the ribbon and a second surface of the ribbon opposed from the first surface of the ribbon. The compressive force can be sufficient to secure the implant in the vicinity of the native valve annulus.

In some embodiments, an implant for treating mal-coaptation of a heart valve is provided. The heart valve can have an annulus and first and second leaflets with an open configuration and a closed configuration. The implant can include a coaptation assist body having a first coaptation surface configured to be disposed to the posterior leaflet, an opposed second surface configured to be disposed toward the anterior leaflet. The implant can include at least one ribbon configured to extend from the coaptation assist body. The ribbon can comprise a shape memory material having a preformed shape with at least one, two, or more discrete curves. The ribbon can be movable from a first compressed configuration to a second expanded configuration. The ribbon can be configured to provide a compressive force on a native valve leaflet between a first surface and a second surface opposed from the first surface of the ribbon. The compressive force can be sufficient to secure the implant, such as the coaptation assist body, in the vicinity of the native valve annulus. The ribbon can be configured to provide ventricular attachment of the implant. The ribbon can comprise a nitinol alloy. The ribbon can be self-expanding. The implant can include a plurality of ribbons. The ribbon can be configured to engage the left ventricle wall. The ribbon can be configured to engage the anterior or the posterior leaflet. The ribbons can resist movement of the implant. The implant can include at least one eyelet configured to accept a portion of an anchor there through. The implant can include a clip and pledget configured to secure the anchor to the coaptation assist body.

In some embodiments, an implant for treating mal-coaptation of a heart valve is provided. The heart valve can have an annulus and first and second leaflets with an open configuration and a closed configuration. The implant can include a coaptation assist body having a first coaptation surface configured to be disposed to the posterior leaflet, an opposed second surface configured to be disposed toward the anterior leaflet. The implant can include a first anchor selectively deployable at a first target location. The implant can include a first rail coupled to the first anchor. The implant can include a second anchor selectively deployable, independently of the deployment of the first anchor, at a second location of the heart. The implant can include a second rail coupled to the second anchor. The coaptation assist body can be configured to slide along the first rail and the second rail to the implantation site. The coaptation assist body can be configured to slide along the first rail and the second rail when collapsed to fit within a delivery catheter. The coaptation assist body can be configured to slide along the first rail and the second rail when expanded upon exiting a delivery catheter. The first rail can be a suture. The second rail can be a suture. The ventricular anchor can be unfolded and held in relation to the coaptation assist body when the coaptation assist body slides along the first rail and the second rail. The ventricular anchor can traverse the mitral valve when the coaptation assist body slides along the first rail and the second rail. The implant can include a clip and pledget configured to secure the first anchor to the coaptation assist body. The implant can include a clip and pledget configured to secure the second anchor to the coaptation assist body. The first rail can be configured to be removed once first anchor is secured to the coaptation assist body. The second rail can be configured to be removed once second anchor is secured to the coaptation assist body.

In some embodiments, an implant for treating mal-coaptation of a heart valve, comprises a coaptation assist body having a first coaptation surface, an opposed second surface, each surface bounded by a first lateral edge; a first anchor selectively deployable at a first target location of the heart near the second leaflet on the annulus and coupleable to the coaptation assist body near the superior edge; a second anchor selectively deployable, independently of the deployment of the first anchor, at a second location of the heart in the ventricle such that the coaptation assist body, when coupled to both the first anchor and the second anchor, extends from the first target location across the valve to the second target location; and wherein the second anchor is a ventricular anchor capable of engaging a wall of the left ventricle.

In some embodiments, a method for treating mal-coaptation of a heart valve in a patient, the heart valve having an annulus and first and second leaflets, the first and second leaflets each comprising a proximal surface, a distal surface, a coaptation edge and an annular edge; the annulus further defining a valve plane, the valve plane separating an atrium proximally and a ventricle distally, the method comprises: selectively deploying a first anchor into heart tissue near anterior and posterior fibrous trigones; selectively deploying a second anchor near the left ventricle wall; coupling the first anchor and the second anchor to a coaptation assist body comprising a coaptation surface and a leaflet surface such that the coaptation assist body is suspended across the valve plane from the atrium proximally to the ventricle distally.

DETAILED DESCRIPTION

Figure 1A:
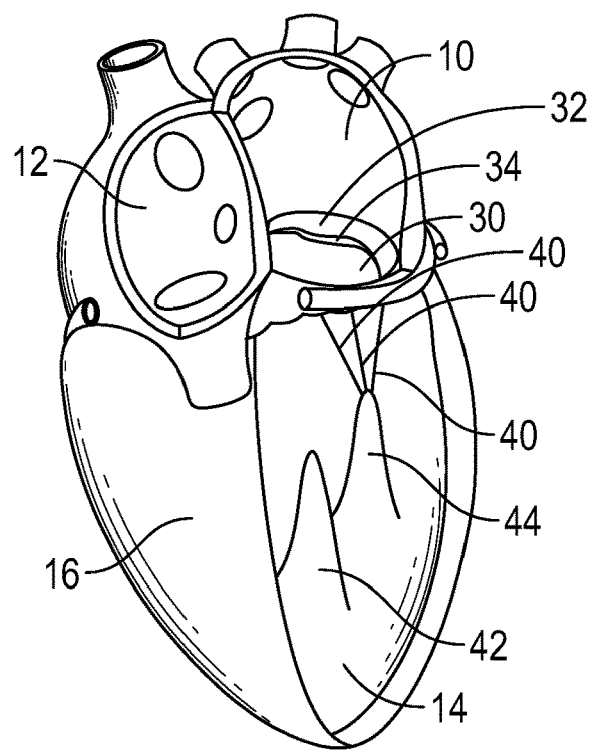
FIGS. 1A-1F schematically illustrate some of the tissues of the heart and mitral valve, as described in the Background section and below, and which may interact with the implants and systems described herein.
Figure 1B:
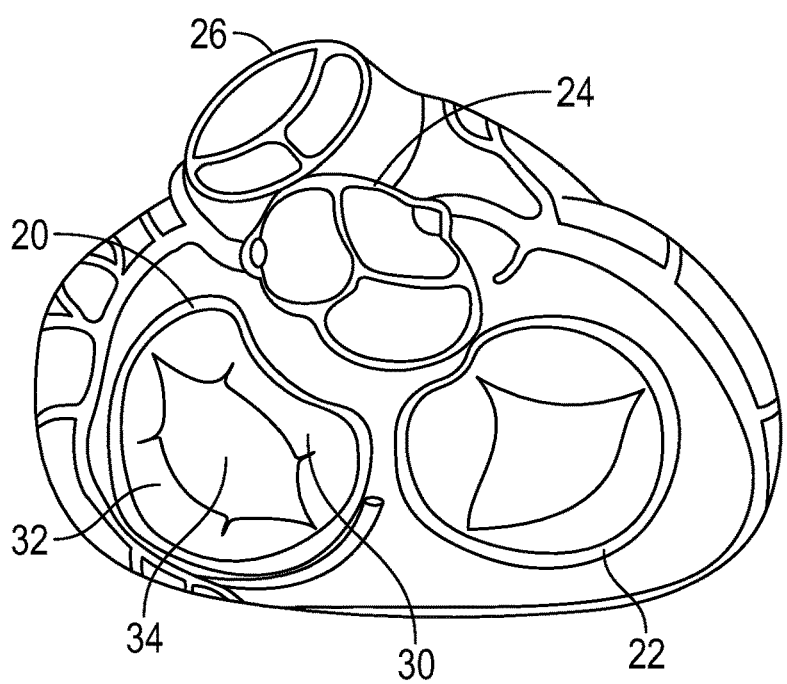
Figure 1C:
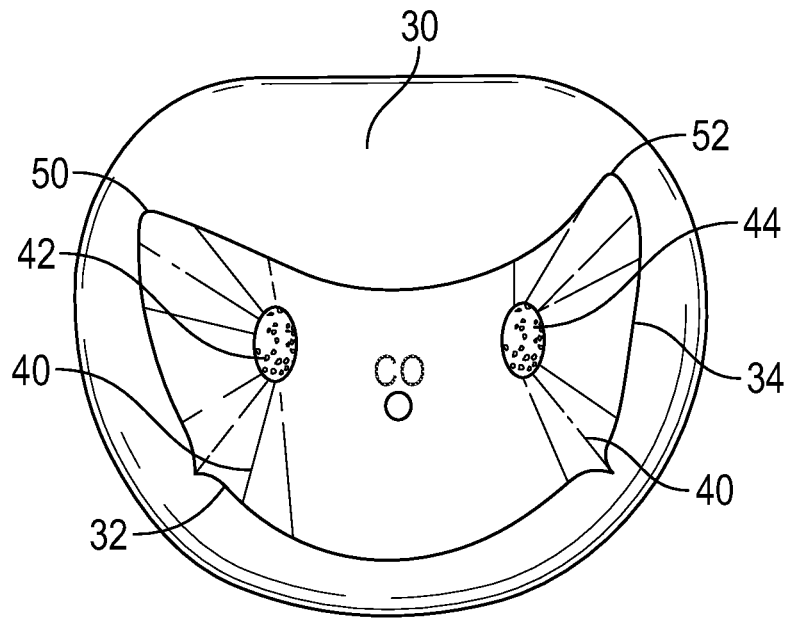
Figure 1D:
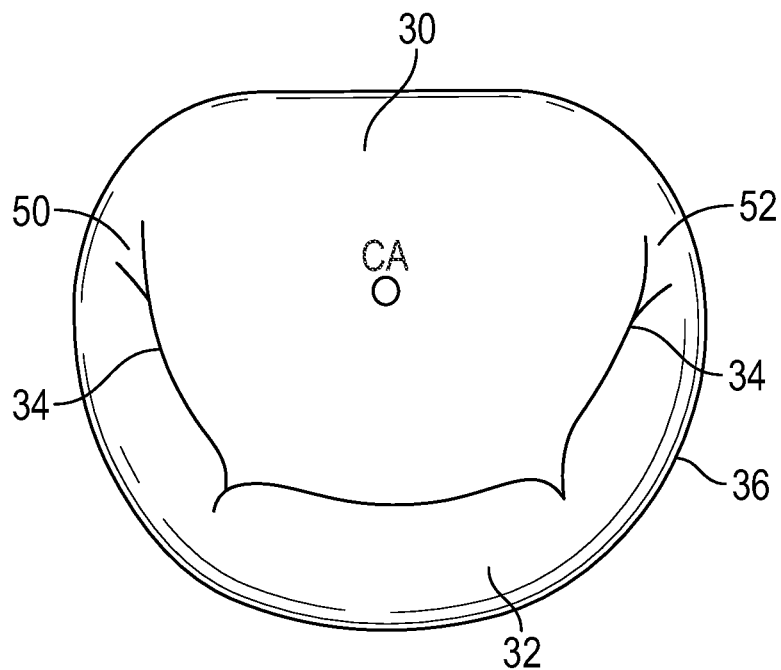

Disclosed herein are improved medical devices, systems, and methods, often for treatment of mitral valve regurgitation and other valve diseases including tricuspid regurgitation. While the description that follows includes reference to the anterior leaflet in a valve with two leaflets such as the mitral valve, it is understand that "anterior leaflet" could refer to one or more leaflets in a valve with multiple leaflets. For example, the aortic valve or tricuspid valve typically has 3 leaflets so the "anterior" could refer to one or two of the medial, lateral, and posterior leaflets. The implants described herein will generally include a coaptation assist body (sometimes referred to herein as a valve body) which is generally along the blood flow path as the leaflets of the valve move back and forth between an open-valve configuration (with the anterior leaflet separated from valve body) and a closed-valve configuration (with the anterior leaflet engaging opposed surfaces of the valve body). The valve body will be disposed between the native leaflets to close the gap caused by mal-coaptation of the native leaflets by providing a surface for at least one of the native leaflets to coapt against, while effectively replacing second native leaflet in the area of the valve which it would occlude during systole, were it functioning normally. The gaps may be lateral (such as may be caused by a dilated left ventricle and/or mitral valve annulus) and/or axial (such as where one leaflet prolapses or is pushed by fluid pressure beyond the annulus when the valve should close).

Among other uses, the coaptation assistance devices, implants, and methods described herein may be configured for treating functional and/or degenerative mitral valve regurgitation (MR) by creating an artificial coaptation zone within which at least one of the native mitral valve leaflets can seal. The structures and methods herein will largely be tailored to this application, though alternative embodiments might be configured for use in other valves of the heart and/or body, including the tricuspid valve, valves of the peripheral vasculature, the inferior vena cava, or the like.

Referring to FIGS. 1A-1D, the four chambers of the heart are shown, the left atrium 10, right atrium 12, left ventricle 14, and right ventricle 16. The mitral valve 20 is disposed between the left atrium 10 and left ventricle 14. Also shown are the tricuspid valve 22 which separates the right atrium 12 and right ventricle 16, the aortic valve 24, and the pulmonary valve 26. The mitral valve 20 is composed of two leaflets, the anterior leaflet 30 and posterior leaflet 32. In a healthy heart, the edges of the two leaflets oppose during systole at the coaptation zone 34.

Figure 1E:
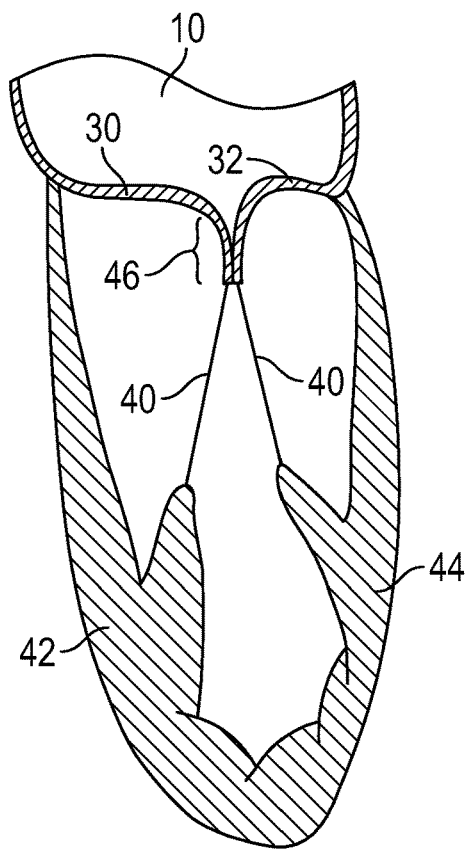

The fibrous annulus 36, part of the cardiac skeleton, provides attachment for the two leaflets 30, 32 of the mitral valve 20, referred to as the anterior leaflet 30 and the posterior leaflet 32. The leaflets 30, 32 are axially supported by attachment to the chordae tendinae 40. The chordae 40, in turn, attach to one or both of the papillary muscles 42, 44 of the left ventricle 14. In a healthy heart, the chordae 40 support structures tether the mitral valve leaflets 30, 32, allowing the leaflets 30, 32 to open easily during diastole but to resist the high pressure developed during ventricular systole. In addition to the tethering effect of the support structure, the shape and tissue consistency of the leaflets 30, 32 helps promote an effective seal or coaptation. The leading edges of the anterior and posterior leaflet come together along a funnel-shaped zone of coaptation 34, with a lateral cross-section 46 of the three-dimensional coaptation zone (CZ) being shown schematically in FIG. 1E.

Figure 1F:
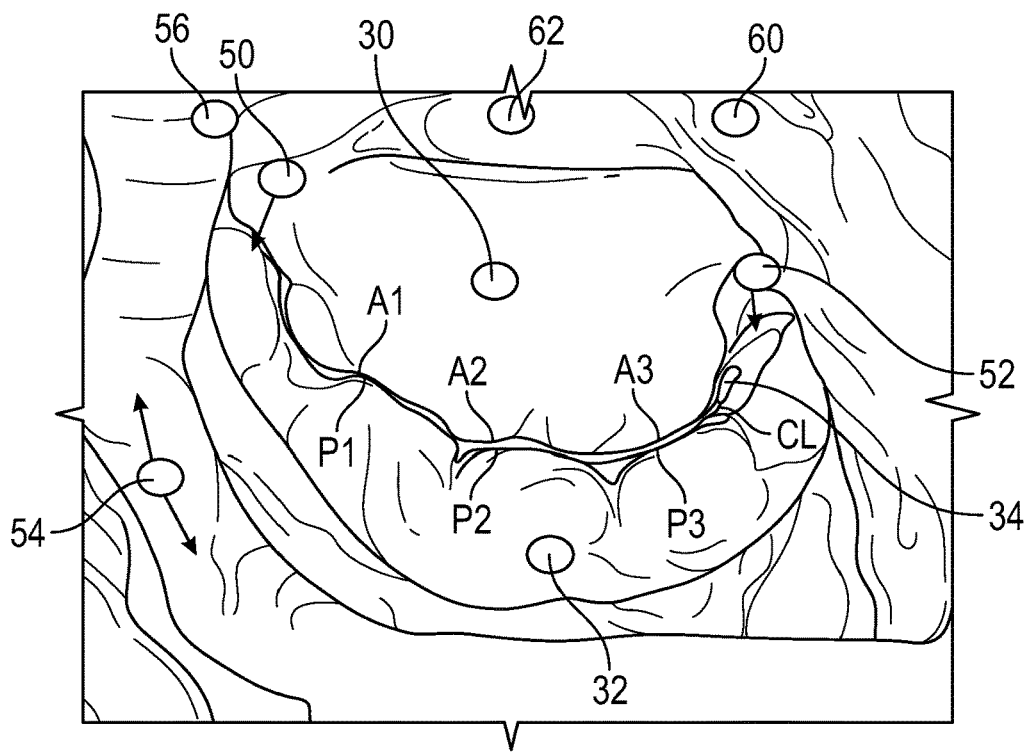

The anterior and posterior mitral leaflets 30, 32 are dissimilarly shaped. The anterior leaflet 30 is more firmly attached to the annulus overlying the central fibrous body (cardiac skeleton), and is somewhat stiffer than the posterior leaflet 32, which is attached to the more mobile posterior mitral annulus. Approximately 80 percent of the closing area is the anterior leaflet 30. Adjacent to the commissures 50, 52, on or anterior to the annulus 36, lie the left (lateral) 56 and right (septal) 60 fibrous trigones which are formed where the mitral annulus is fused with the base of the non-coronary cusp of the aorta (FIG. 1F). The fibrous trigones 56, 60 form the septal and lateral extents of the central fibrous body 62. The fibrous trigones 56, 60 may have an advantage, in some embodiments, as providing a firm zone for stable engagement with one or more annular or atrial anchors. The coaptation zone 34 between the leaflets 30, 32 is not a simple line, but rather a curved funnel-shaped surface interface. The first 50 (lateral or left) and second 52 (septal or right) commissures are where the anterior leaflet 30 meets the posterior leaflet 32 at the annulus 36. As seen most clearly in the axial views from the atrium of FIGS. 1C, 1D, and 1F, an axial cross-section of the coaptation zone 34 generally shows the curved line CL that is separated from a centroid of the annulus CA as well as from the opening through the valve during diastole CO. In addition, the leaflet edges are scalloped, more so for the posterior leaflet 32 versus the anterior leaflet 30. Mal-coaptation can occur between one or more of these A-P (anterior-posterior) segment pairs A1/P1, A2/P2, and A3/P3, so that mal-coaptation characteristics may vary along the curve of the coaptation zone 34.

Figure 2A:
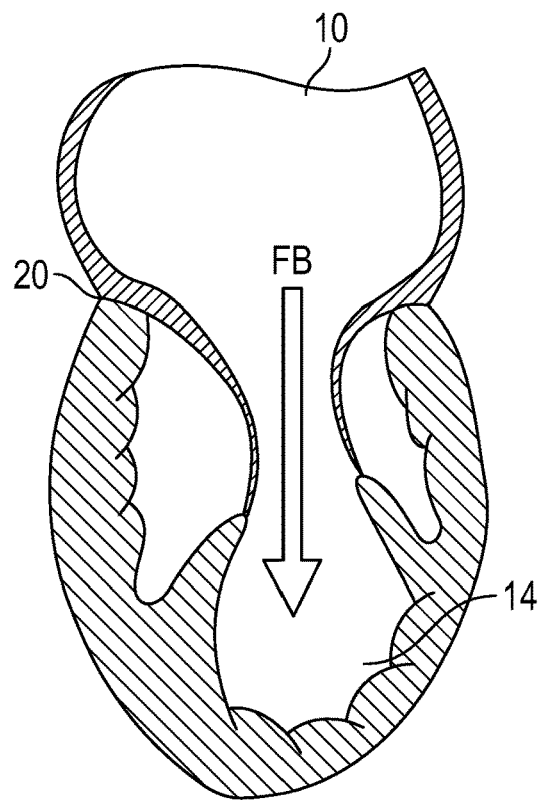
FIG. 2A illustrates a simplified cross-section of a heart, schematically showing mitral valve function during diastole.
Figure 2B:
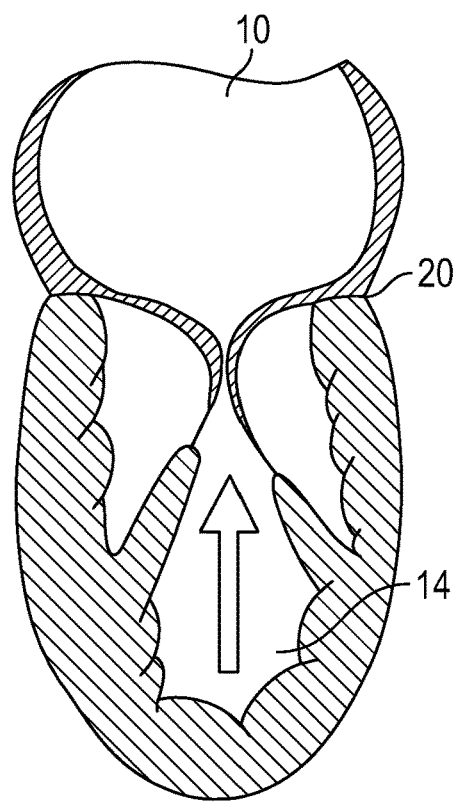
FIG. 2B illustrates a simplified cross-section of a heart, schematically showing mitral valve function during systole.

Referring now to FIG. 2A, a properly functioning mitral valve 20 of a heart is open during diastole to allow blood to flow along a flow path FP from the left atrium 10 toward the left ventricle 14 and thereby fill the left ventricle 14. As shown in FIG. 2B, the functioning mitral valve 20 closes and effectively seals the left ventricle 14 from the left atrium 10 during systole, first passively then actively by increase in ventricular pressure, thereby allowing contraction of the heart tissue surrounding the left ventricle 14 to advance blood throughout the vasculature.

Referring to FIGS. 3A-3B and 4A-4B, there are several conditions or disease states in which the leaflet edges of the mitral valve 20 fail to oppose sufficiently and thereby allow blood to regurgitate in systole from the left ventricle 14 into the left atrium 10. Regardless of the specific etiology of a particular patient, failure of the leaflets to seal during ventricular systole is known as mal-coaptation and gives rise to mitral regurgitation.

Figure 3A:
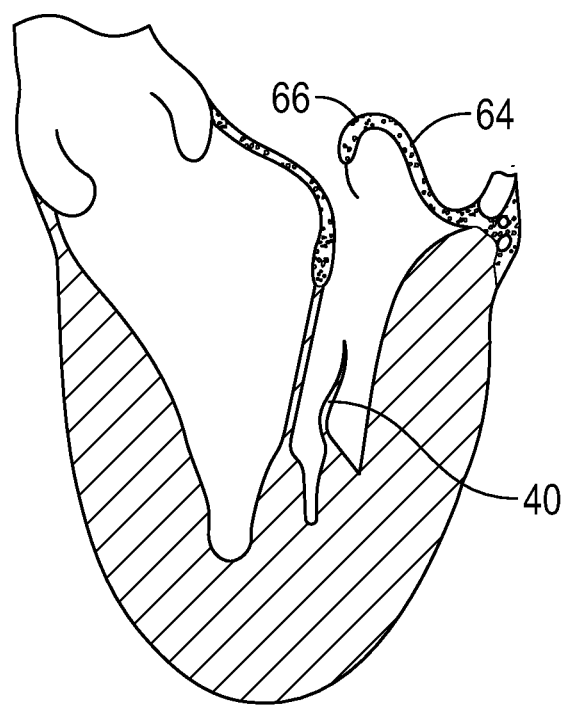
FIGS. 3A-3B illustrate a simplified cross-section of a heart, schematically showing mitral valve regurgitation during systole in the setting of mal-coaptation of the mitral valve leaflets.

Generally, mal-coaptation can result from either excessive tethering by the support structures of one or both leaflets 30, 32, or from excessive stretching or tearing of the support structures. Other, less common causes include infection of the heart valve, congenital abnormalities, and trauma. Valve malfunction can result from the chordae tendinae 40 becoming stretched, known as mitral valve prolapse, and in some cases tearing of the chordae 40 or papillary muscle 44, known as a flail leaflet 64, as shown in FIG. 3A. Or if the leaflet tissue itself is redundant, the valves may prolapse so that the level of coaptation occurs higher into the left atrium 10, opening the valve 20 higher in the left atrium 10 during ventricular systole 66. Either one of the leaflets 30, 32 can undergo prolapse or become flail. This condition is sometimes known as degenerative mitral valve regurgitation.

Figure 3B:
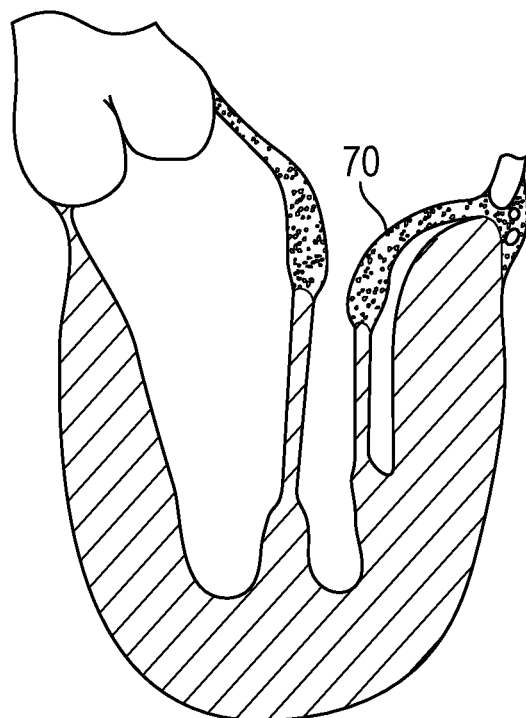

In excessive tethering, as shown in FIG. 3B, the leaflets 30, 32 of a normally structured valve may not function properly because of enlargement of or shape change in the valve annulus 36: so-called annular dilation 70. Such functional mitral regurgitation generally results from heart muscle failure and concomitant ventricular dilation. And the excessive volume load resulting from functional mitral regurgitation can itself exacerbate heart failure, ventricular and annular dilation, thus worsening mitral regurgitation.

Figure 4A:
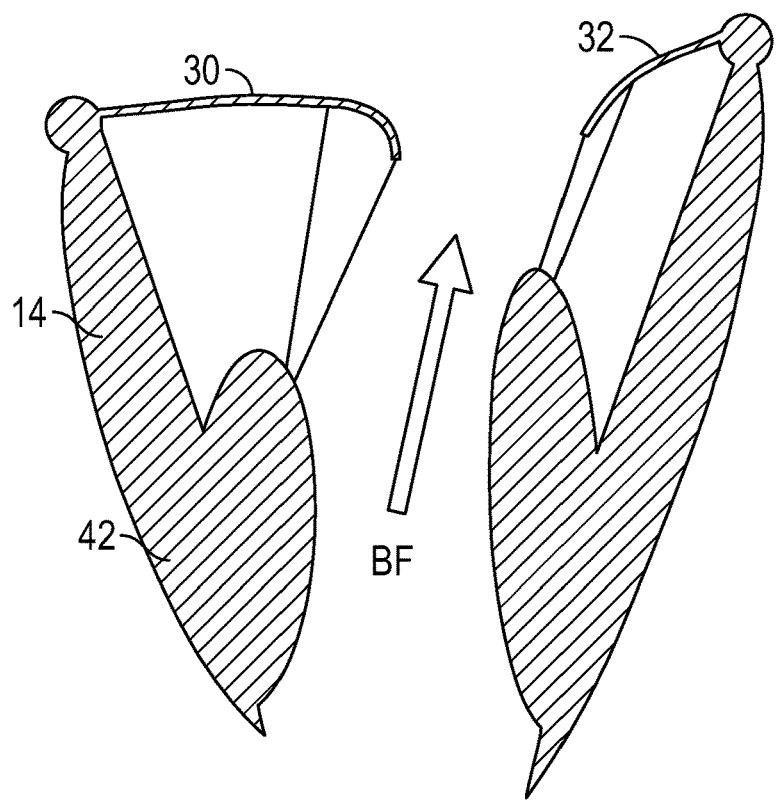
FIG. 4A illustrates a stylized cross section of a heart, showing mitral valve mal-coaptation in the settings of functional mitral valve regurgitation.
Figure 4B:
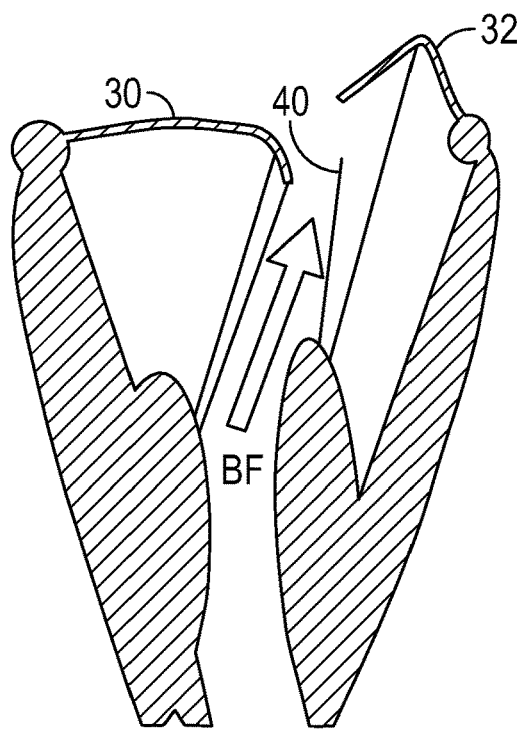
FIG. 4B illustrates a stylized cross section of a heart, showing mitral valve mal-coaptation in the settings of degenerative mitral valve regurgitation.

FIG. 4A-4B illustrate the backflow BF of blood during systole in functional mitral valve regurgitation (FIG. 4A) and degenerative mitral valve regurgitation (FIG. 4B). The increased size of the annulus 36 in FIG. 4A, coupled with increased tethering due to hypertrophy of the left ventricle 14 and papillary muscles 42, 44, prevents the anterior leaflet 30 and posterior leaflet 32 from opposing, thereby preventing coaptation. In FIG. 4B, the tearing of the chordae 40 causes prolapse of the posterior leaflet 32 upward into the left atrium 10, which prevents opposition against the anterior leaflet 30. In either situation, the result is backflow of blood into the left atrium 10, which decreases the effectiveness of left ventricle compression.

FIGS. 5A-5D show four views of an embodiment of a coaptation assistance device 80 which comprises a body 82. The body 82 comprises a first surface 84 disposed toward a mal-coapting native leaflet, in the instance of a mitral valve 20, the posterior leaflet 32 and a second surface 86 which may be disposed toward the anterior leaflet 30. The first and second surfaces 84, 86 can be considered a coaptation surface. The superior edge 90 of the body 82 may be curved to match the general shape of the annulus 36 or adjoining atrial wall. The coaptation assistance device 80 can comprise a frame 88 configured to provide structural support to the coaptation assistance device 80. In some embodiments, the frame 88 is collapsible to fit within a delivery catheter, as described herein.

Figure 5A:
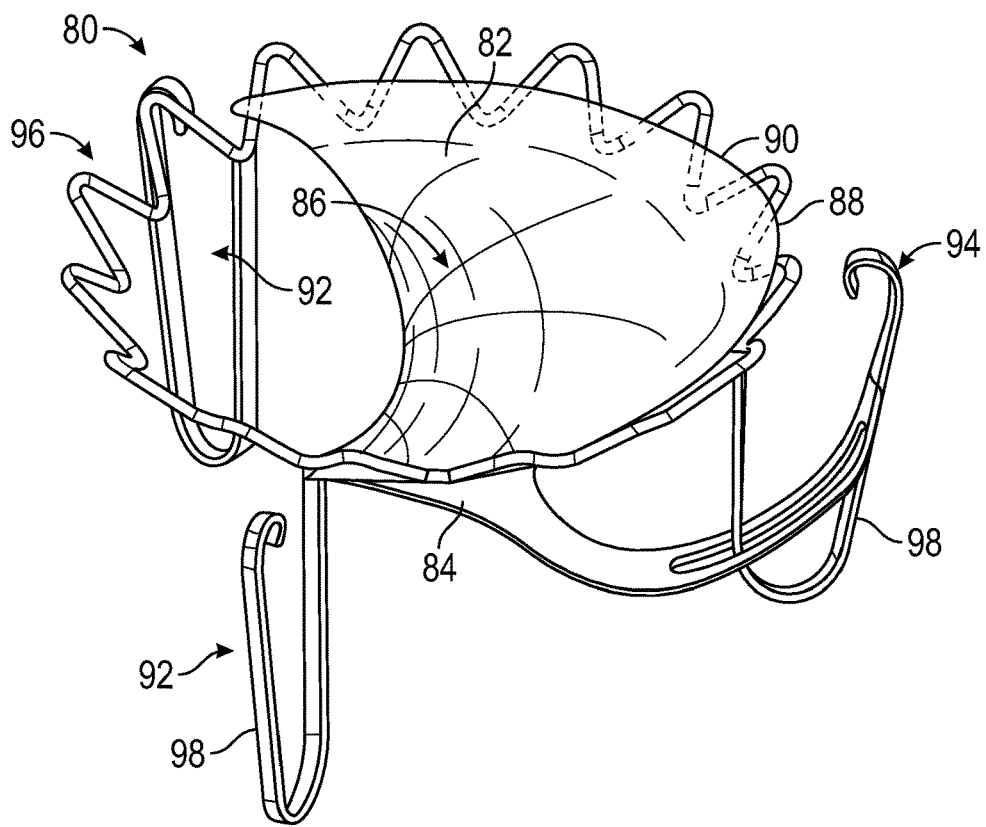
FIG. 5A schematically illustrates an embodiment of the coaptation assistance device.
Figure 5B:
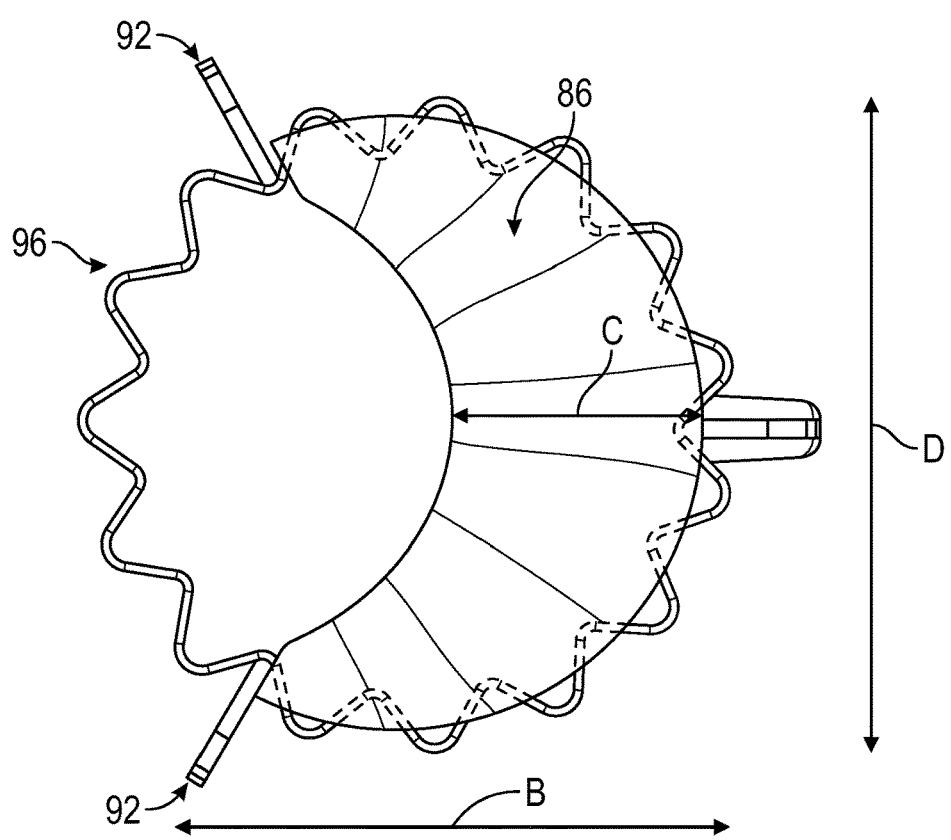
FIG. 5B schematically illustrates a top view of the coaptation assistance device of FIG. 5A.
Figure 5C:
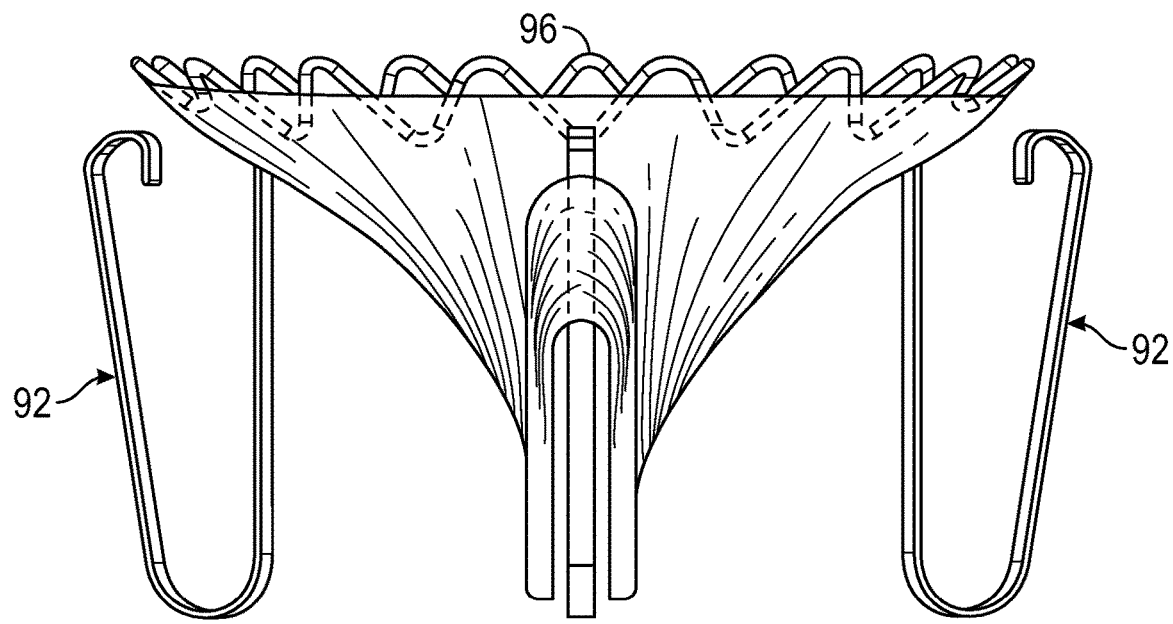
FIGS. 5C-5D schematically illustrates lateral views of the coaptation assistance device of FIG. 5A.
Figure 6A:
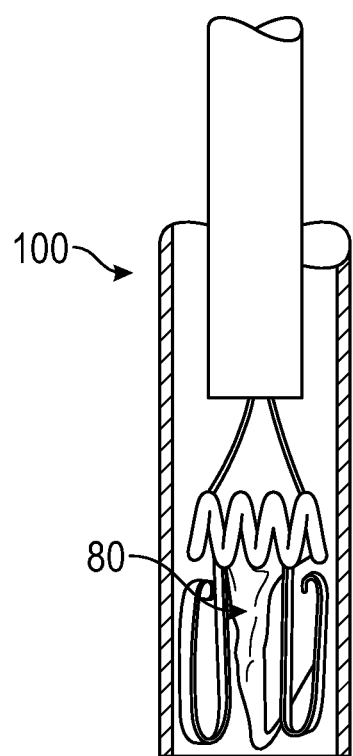
FIG. 6A schematically illustrates the coaptation assistance device of FIG. 5A in its collapsed state.

The coaptation assistance device 80 may include one or a plurality of anchors to stabilize the device, such as atrial anchors and/or ventricular anchors, with the anchors optionally providing redundant fixation. As shown in FIG. 5A, the implant has lateral commissural anchors 92 which may help maintain the shape and position of the coaptation assistance device 80 once deployed in the heart. In some embodiments, the lateral commissural anchors 92 are placed under the leaflets 30, 32 at the site of commissures 50, 52. The coaptation assistance device 80 can also have a posterior anchor 94. In some embodiments, the posterior anchor 94 engages the area under the posterior leaflet 32. As shown in FIG. 5A, the commissural anchors 92 and the posterior anchors 94 can each comprise ribbons 98 that have a bias such that they can exert a force, and rest against the tissue of the heart, such as the ventricle. The ribbons 98 function as anchors and resist movement of the coaptation assistance device 80, and can do so without penetrating the myocardium in some embodiments. The positioning of the ribbons 98 against features of the anatomy may provide stability of the coaptation assistance device 80. The ribbons 98 may comprise bio-inert materials such as, for example, Platinum/Ir, a Nitinol alloy, and/or stainless steel. In some embodiments, the ribbons 98 comprise NiTi. In some embodiments, the ribbons 98 have a pre-determined curve. The material selection combined with the selected shape provides anchors 92, 94 that are spring loaded. The ribbons 98 extend in a direction, such as downward, from the frame 88. The ribbons 98 curve and then extend upward, forming a generally U-shaped configuration. The ribbons 98 comprise a rounded top surface configured to abut tissue. Other shapes for the ribbons 98 are contemplated. As disclosed herein, the coaptation assistance device 80 is collapsed inside the delivery catheter 100 as shown in FIG. 6A. The spring loaded ribbons 98 are capable of being collapsed within the delivery catheter. Upon exiting the catheter, the spring loaded ribbons 98 rapidly expand into the preformed shape. In some embodiments, the ribbons 98 are provided for ventricular attachment. The ribbons 98 allow for very rapid attachment of the coaptation assistance device 80 to the tissue, since the ribbons 98 do not rely on annular sutures and do not require tying knots in some embodiments. The deployment of the ribbons 98 can be faster than engaging a helical anchor, for instance.

In some embodiments, the coaptation assistance device 80 includes an annular anchor 96. The annular anchor 96 can be, in some embodiments, a radially expandable stent-like structure, as shown in FIG. 5A. Like the commissural anchors 92, the annular anchor 96 can be collapsed to fit inside a catheter, described herein. In some embodiments, the annular anchor 96 can be delivered to the site of the mitral valve 20. In some embodiments, the annular anchor 92 is intended for placement in the mitral annulus 36. The annular anchor 96 may include a plurality of barbs for acute fixation to the surrounding tissue. In some embodiments, the annular anchor 96 may be simply held in place via radial forces. The annular anchor 96, if it is included, may be covered with biocompatible materials such as ePTFE or Dacron to promote endothelialization and, optionally, chronic tissue ingrowth or encapsulation of the annular anchor for additional stability.

In other embodiments, the atrial anchors may comprise a plurality of helixes, clips, harpoon or barb-shaped anchors, or the like, appropriate for screwing or engaging into the annulus 36 of the mitral valve 20, tissues of the ventricle 14, other tissues of the atrium 10, or other tissue. The body 82 can include one or more features such as eyelets or tethers to couple with the atrial anchors.

The coaptation assistance device 80 has a geometry which permits it to traverse the mitral valve 20 between attachment sites in the left atrium 10 and left ventricle 14, to provide a coaptation surface 86 for the anterior leaflet 30 to coapt against, and attach to the left atrium 10 or annulus 36 such that it effectively seals off the posterior leaflet 32. In the instance that the posterior leaflet 32 is or has been removed, the coaptation assistance device 80 replaces the posterior leaflet 32.

Figure 5D:
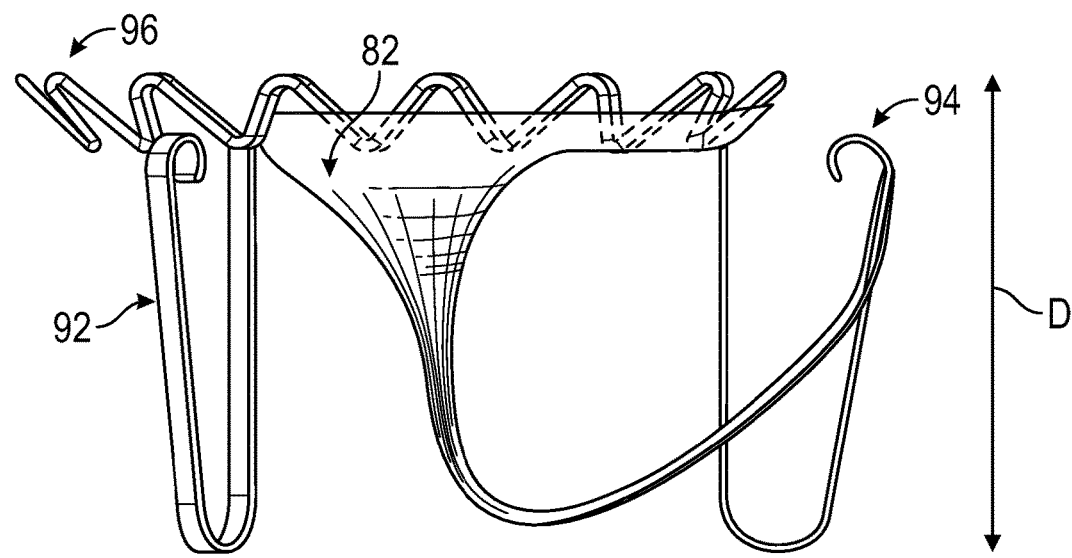

Different sized coaptation assistance device 80, particularly the different sized bodies 82, can be placed such that the native anterior leaflet 30 opposes the coaptation surface 86 at the appropriately established coaptation point, blocking flow of blood during contraction of the left ventricle 14. In order to accomplish this, a variety of sizes of coaptation assistance device 80 are provided, with differing dimensions configured to fit varying anatomies. As seen in the top view of FIG. 5B, there is a dimension A which is an intercommissural distance. This distance may be, for example, within a range of about 20 mm to about 80 mm, and in one embodiment about 40 mm. There is a dimension B which is an anterior-posterior diameter. This diameter may be, for example, within a range of about 20 mm to about 60 mm, and in one embodiment about 35 mm. There is a dimension C which is the anterior-posterior projection. This dimension may be within a range of, e.g., about 10 mm to about 30 mm depending on the mitral valve regurgitation (MR). For degenerative MR, this dimension may be, e.g., within a range of about 10 mm to about 20 mm. For functional MR, this dimension may be, e.g., within a range of about 20 mm to about 30 mm. As shown in FIG. 5D, there is a dimension D which is the coaptation assistance device 80 height. This dimension may be, e.g., within a range of about 20 mm to about 50 mm, and in one embodiment about 25 mm.

Turning now to FIGS. 6A-6D, an embodiment of the coaptation assistance device 80 is shown. It can be seen that in some embodiments, the coaptation assistance device 80 is collapsed inside the delivery catheter 100. The stent-like structure of the frame 88 of the coaptation assistance device 80 including the structure of the annular anchor 96 and commissural anchors 92 allows the coaptation assistance device 80 to be collapsed.

Figure 6B:
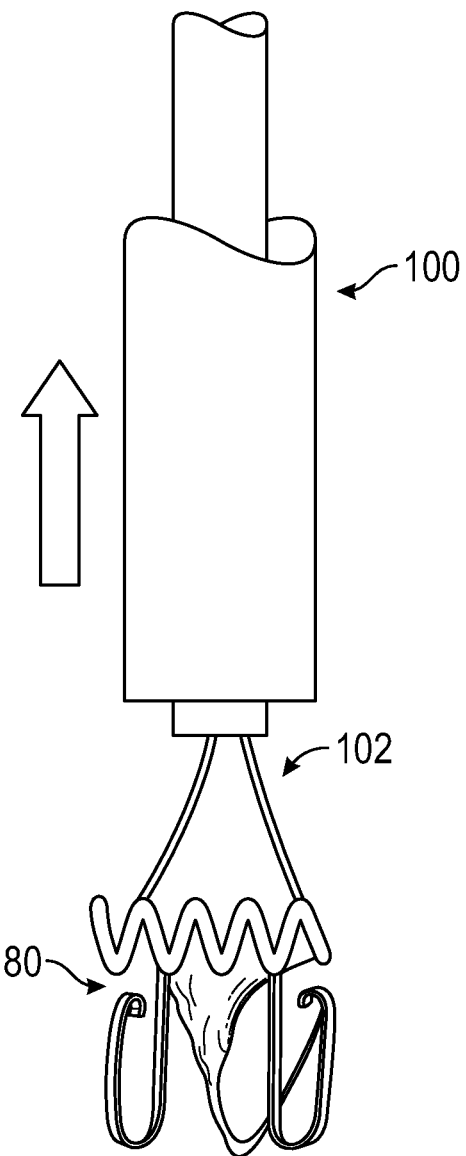
FIG. 6B schematically illustrates the coaptation assistance device of FIG. 5A as it is deployed.
Figure 6D:
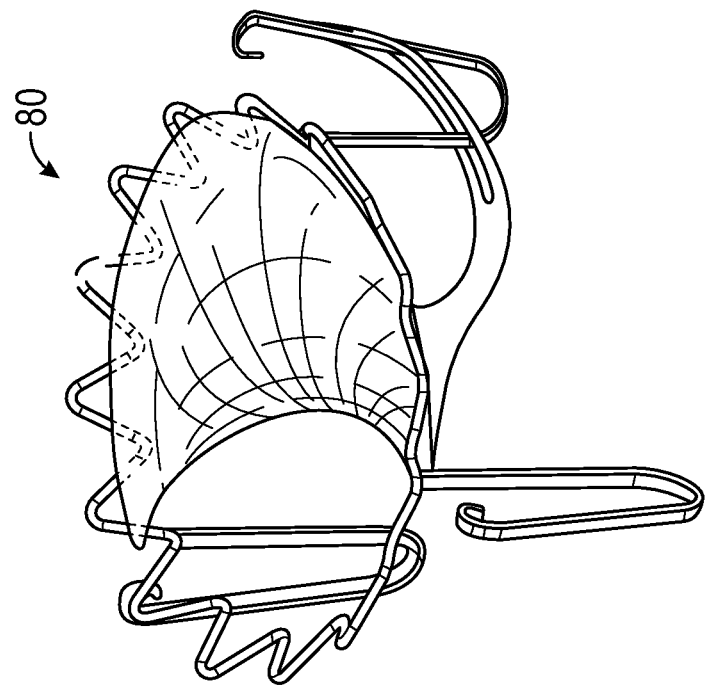
FIG. 6D schematically illustrates the coaptation assistance device of FIG. 5A deployed.
Figure 6C:
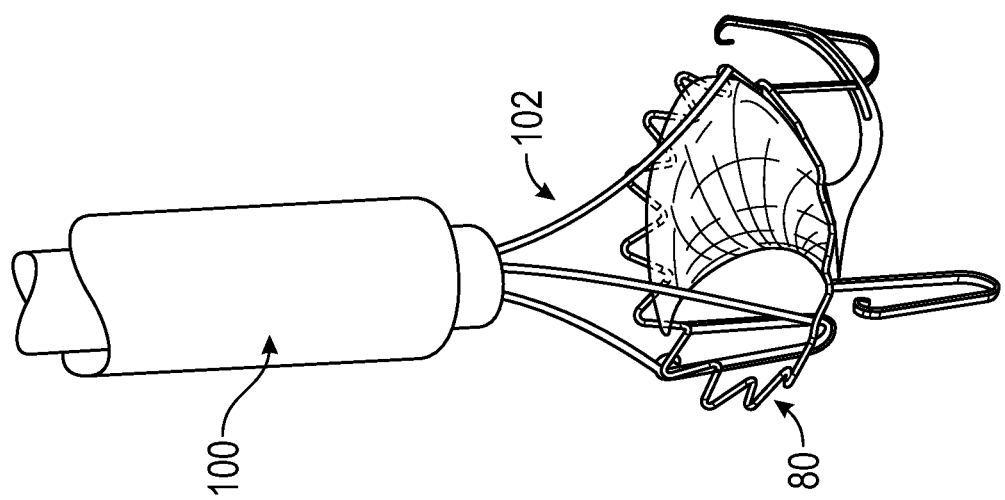
FIG. 6C schematically illustrates the coaptation assistance device of FIG. 5A deployed with connecting struts.

In the embodiment shown in FIGS. 6B-6C, a number of struts 102 may couple to the coaptation assistance device 80. The struts 102 may connect to the coaptation assistance device 80 at any number of locations, e.g., superior edge 90, annular anchor 94, commissural anchors 92, to a ventricular hub described herein. The struts 102 couple the coaptation assistance device 80 to the catheter 100 and/or implant introducer 104. Each strut 102 may comprise a single longitudinal element or be doubled over to comprise two or more strands. A single strut 102 may be comprised of a strand of Nitinol wire, suture, or other material which loops toward the superior aspect of the implant. This loop area may provide reinforcement around an interruption in the covering material. In some embodiments, the struts 102 could include clips, jaws, adhesive, or another mechanism to form a releasable attachment between the struts 102 and the coaptation assistance device 80. The struts 102 may be, as shown, placed such that they are relatively evenly spaced, or may be concentrated toward the center or lateral edges of the coaptation assistance device 80. The struts 102 may be coupleable with the anchors 92, 94, 96 which may be deployed into various locations including the mitral annulus 36, left atrium 10, left auricle, one of the fibrous trigones 56, or the left ventricle 14.

As shown in FIGS. 6A-6D, the body 82 of the coaptation assistance device 80 can be delivered by a delivery catheter 100 and may be capable of expanding from a smaller profile to a larger profile to dimensions appropriate for placement in between the valve's native leaflets 30, 32. The coaptation assistance device 80 is expanded as it is exposed from the tip of the delivery catheter 100. In some embodiments, the delivery catheter 100 is pulled back to expose the coaptation assistance device 80 as shown by the arrow in FIG. 6B. The exposed coaptation assistance device 80 is detached from the delivery catheter 100 as shown in FIG. 6D, for instance by releasing the struts 102.

Figure 7:
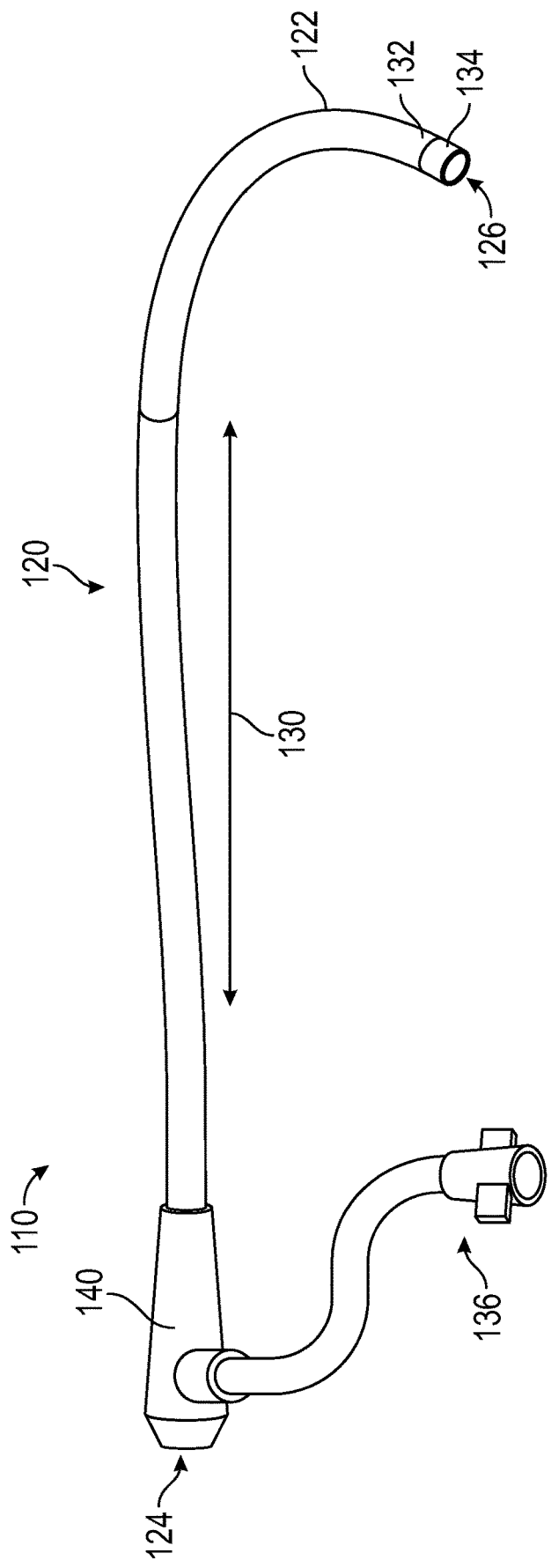
FIG. 7 schematically illustrates an embodiment of the transseptal sheath.

Turning now toward implantation, a coaptation assistance device 180 may be implanted through a minimally invasive or transcatheter technique utilizing a delivery system 106. The coaptation assistance device 180 can be substantially similar to the coaptation assistance device 80 described herein. The delivery system 106 can include one or more of the following devices: a transseptal sheath 110 shown in FIG. 7, an anchor delivery catheter 112 shown in FIG. 8, an implant delivery catheter 114 shown in FIGS. 9A-9B, and a clip delivery catheter 116 shown in FIG. 10. As illustrated in FIG. 7, the delivery system 106 may include a transseptal sheath 110 having a shaft 120 that may be made of a polymeric or other material. In some embodiments, the shaft 120 is a braid or coil reinforced polymer shaft. In some embodiments, the shaft 120 has multiple durometers, such as a first smaller durometer at a first location and a second larger durometer at a second location distal or proximal to the first location. In some embodiments, the transseptal sheath 110 is pre-shaped. The shaft 120 can include at least one through lumen (e.g., two, or more through lumens). In some embodiments, the transseptal sheath 110 comprises an actively deflectable tip 122 to facilitate navigation into the left ventricle 14. The deflectable tip 122 can be controlled by various mechanisms, for instance via pullwires operably attached to the deflectable tip 122 and connected to a proximal control.

The transseptal sheath 110 may include a seal 124 to accommodate various instruments and guidewires inserted therein. The seal can accommodate diameters including the outer diameter of the anchor delivery catheter 112, the implant delivery catheter 114, and the clip delivery catheter 116. In some embodiments, the accommodated diameters can be up to 22 Fr. The transseptal sheath 110 may include lined inner diameter 126. The lined inner diameter 126 may be within a range of about 10 to about 22 Fr, and in one embodiment preferably 16 Fr. The transseptal sheath 110 has sufficient length over a section 130 to span from the access point (e.g., outside the body) to the tip of the left ventricle 14. The access point may be via groin/femoral access. This length may be, e.g., within a range of about 80 cm to about 120 cm, and in one embodiment about 100 cm. The transseptal sheath 110 may include atraumatic tip 132. The tip 132 may include a marker band 134 for visualization. The transseptal sheath 110 may include flush port 136 operably connected to the central lumen of shaft 120 at a proximal hub 140 as illustrated. The system may further include additional ports, including flush, irrigation and/or aspiration ports to remove fluid or air from the system and allow injection of fluids such as saline or contrast media to the site of implantation.

Figure 8:
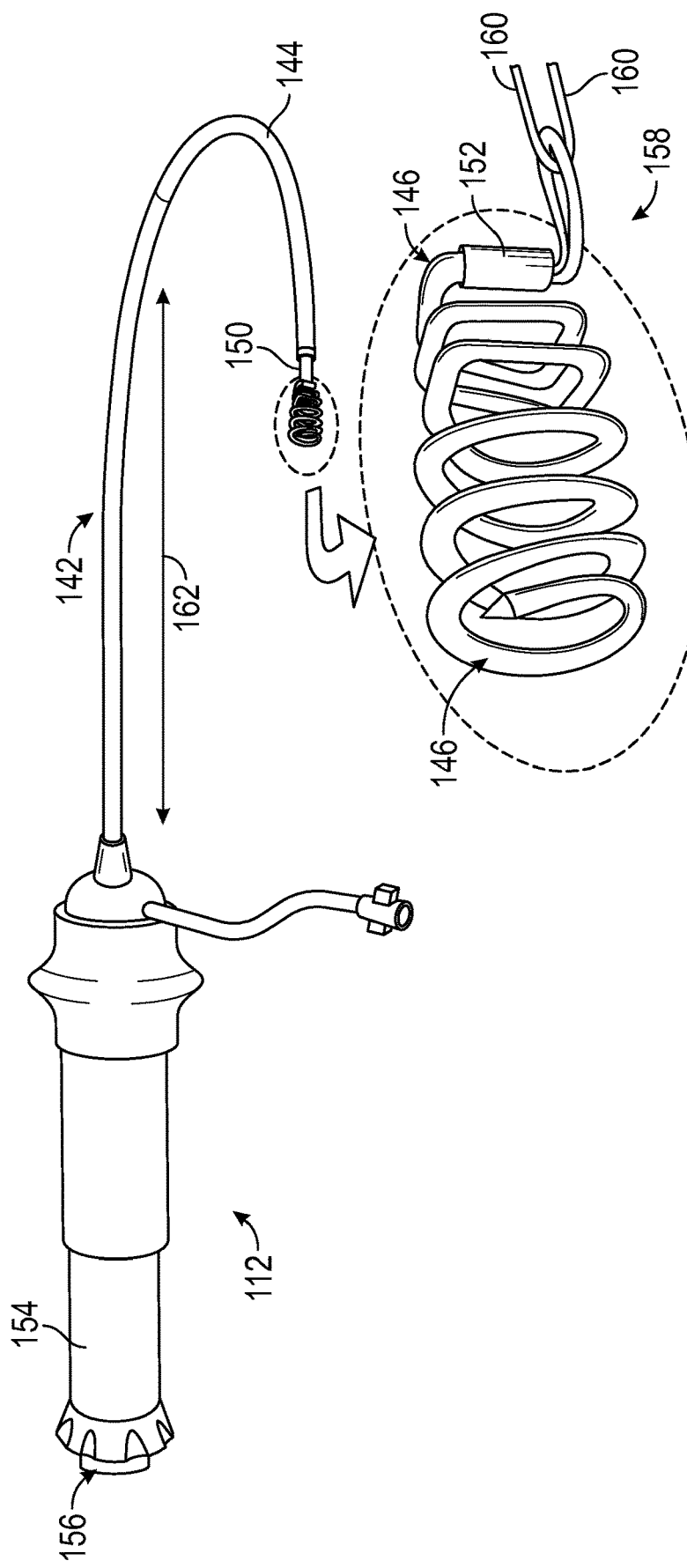
FIG. 8 illustrates an embodiment of the anchor delivery catheter.

Referring now to FIG. 8, aspects of the anchor delivery catheter 112 are illustrated. FIG. 8 shows an embodiment of the anchor delivery catheter 112. The anchor delivery catheter 112 may include a shaft 142 made of a material such as a polymer. In some embodiments, the shaft 142 is a braid or coil reinforced polymer shaft. In some embodiments, the shaft 142 has multiple durometers, such as a first smaller durometer at a first location and a second larger durometer at a second location distal or proximal to the first location. The anchor delivery catheter 112 has sufficient length over a section 162 to span from the access point (e.g., outside the body) and through the transseptal sheath 110. This length may be, e.g., within a range of about 90 cm to about 130 cm, and in one embodiment about 110 cm. In other embodiments, the anchor delivery catheter 112 comprises an actively deflectable tip 144 to facilitate navigation of the anchors to the anchoring sites. The anchor delivery catheter 112 is configured to deploy an anchor 146.

The anchor delivery catheter 112 may include a drive shaft 150. The drive shaft 150 is configured to couple with a drive continuation 152 to allow transmission of torque to the anchor 146. In some embodiments, the drive shaft 150 is flexible. In some embodiments, the drive shaft 150 is capable of being advanced or retracted. The anchor delivery catheter 112 may include a handle 154. The handle 154 may include a knob 156 to enable simple manipulation of the torque or position of the anchor 146. The knob is internally connected to the drive shaft 150 thereby allowing transmission of torque to the anchor 146 when the knob 156 is rotated.

The anchor 146 has an outer diameter which may be within a range of about 1 to about 6 mm, and in one embodiment preferably 4 mm. The anchor 146 may be helical with a pitch within a range of about 0.4 to about 1.5 mm, and in one embodiment preferably 0.8 mm. The anchor 146 in some embodiments has a wire diameter which may be within a range of about 0.25 to about 0.75 mm, and in one embodiment preferably 0.5 mm. The anchor 146 may be coupled to the drive continuation 152. As shown, the drive continuation 152 can be a square continuation of the anchor helix. However, the drive continuation 152 may be of any shape, such as triangular or hexagonal, capable of transmitting the torque imparted by the drive shaft 150. The anchor 146 can include anchor suture 158. The anchor delivery catheter 112 may include one or more rails 160 (e.g., sutures, guidewires) attached to the proximal end of anchor 146 and/or the anchor suture 158. For the anchor 146 shown in FIG. 8, such as the trigonal anchor, the rails 160 (e.g., sutures, guidewires) facilitate subsequent proper placement of the coaptation assistance device 180. For some method, the rails 160 are cut after anchor placement.

Figure 9A:
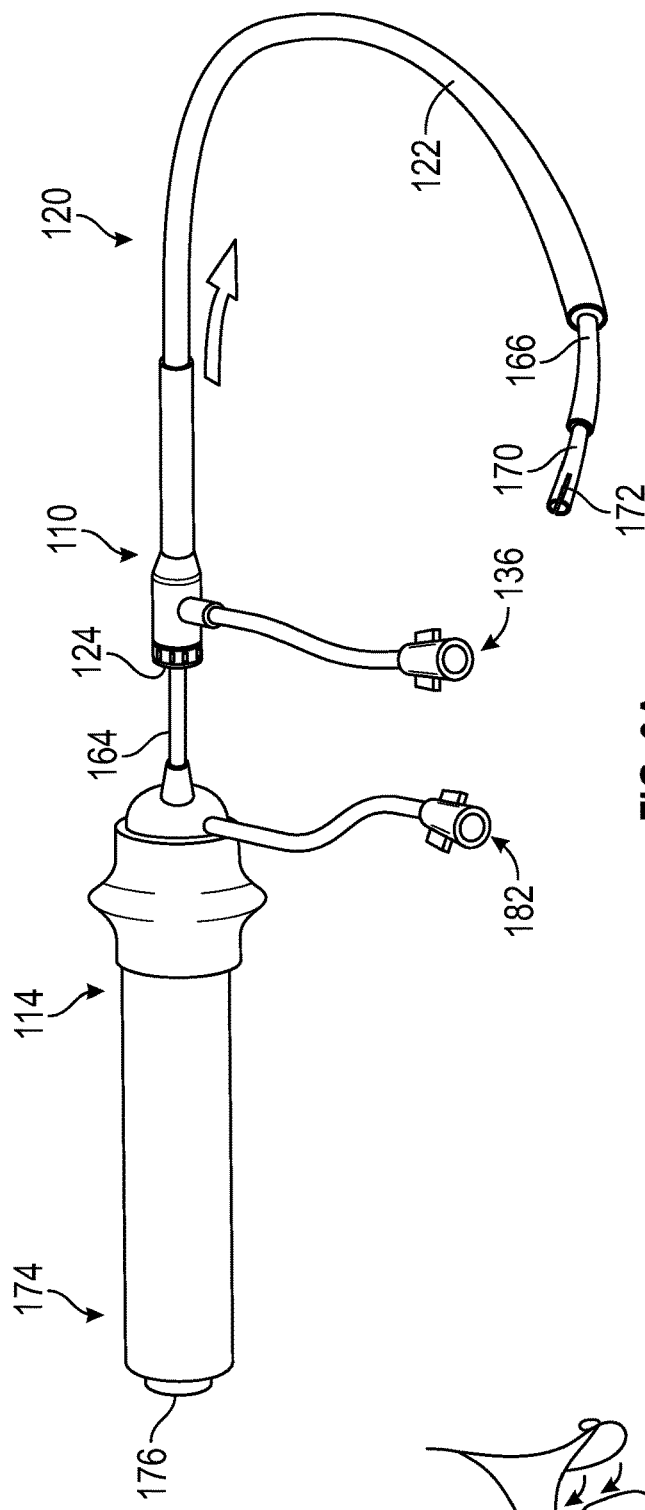
FIG. 9A schematically illustrates an embodiment of an implant delivery catheter and the transseptal sheath of FIG. 7.

Referring now to FIG. 9A, aspects of the implant delivery catheter 114 are illustrated. The implant delivery catheter 114 can be inserted into the transseptal sheath 110 shown. The seal 124 is sized to accommodate the implant delivery catheter 114. The transseptal sheath 110 allows the introduction of the implant delivery catheter 114 through a lumen of the shaft 120 and into the left atrium 10. The transseptal sheath 110 may include a variable stiffness outer shaft 120 with at least one lumen, the lumen sized to allow insertion of the implant delivery catheter 114 and/or coaptation assistance device 180 through the lumen. The deflectable tip 122 and/or a deflectable portion of the shaft 120 may facilitate alignment of the coaptation assistance device 180 with the valve leaflets 30, 32.

The implant delivery catheter 114 comprises a shaft 164. The shaft 164 can be a variable stiffness shaft, with the stiffness varying along a dimension, for instance along the length. The shaft 164 can include at least one through lumen (e.g., two, or more through lumens). The shaft 164 can be include a deflectable tip 166 configured for deflecting along at least a distal section. The deflectable tip 166 can be controlled by various mechanisms, for instance via pullwires operably attached to the deflectable tip 166 and connected to a proximal control.

The delivery catheter may further include an implant introducer 170. The implant introducer 170 can be sized to pass through the shaft 164 of the implant delivery catheter 114. The implant introducer 170 can include a slot 172. The implant delivery catheter 114 may further include a handle 174 to manipulate the implant delivery catheter 114 within the transseptal sheath 110 and/or body of the patient. The handle 174 may include a knob 176 to enable simple manipulation of the position of the coaptation assistance device 180. The knob 176 is internally connected to the implant introducer 170 thereby allowing transmission of movement to the implant introducer 170 when the knob 176 is manipulated. In some embodiments, the knob 176 can manipulate the docking and undocking of the coaptation assistance device 180 with the implant delivery catheter 114. The handle 174 may further include one or more ports 182, such as a flush, irrigation and/or aspiration port to remove the air from the system and allow injection of fluids such as saline or contrast media to the site of implantation.

Figure 9C:
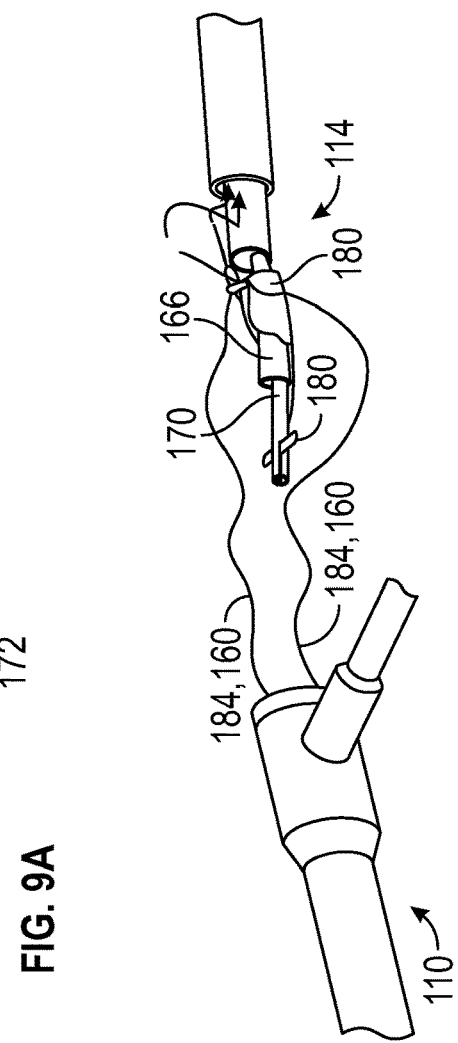
FIG. 9C schematically illustrates the advancement of the coaptation assistance device over two rails.
Figure 9B:
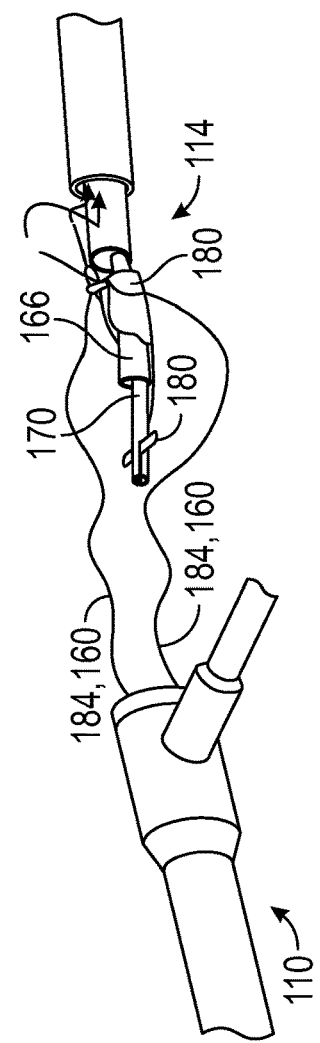
FIG. 9B schematically illustrates the attachment of the coaptation assistance device to the implant delivery catheter.

As shown in FIG. 9B, the coaptation assistance device 180 is inserted into the implant delivery catheter 114. The coaptation assistance device 180 is shown in the top view of FIG. 9B. In some embodiments, the coaptation assistance device 180 is unfolded in the direction of the arrows as shown in the middle view of FIG. 9B. The coaptation assistance device 180 can be coupled to the implant introducer 170. In some embodiments, a portion of the coaptation assistance device 180 is held within the slot 172. In some embodiments, a portion of the coaptation assistance device 180 folds around the deflectable tip 166 of the implant delivery catheter 114 in the direction of the arrows shown in the bottom view of FIG. 9B. The coaptation assistance device 180 can be coupled to the implant introducer 170 and the deflectable tip 166 of the implant delivery catheter 114. As shown in FIG. 9C, the attached coaptation assistance device 180 can slide along (e.g., engage) one or more rails 184 (e.g., two rails 184), which may be rails 160 coupled to anchor 146. The rails 184 can extend through transseptal sheath 110 from the anchor 146 to the coaptation assistance device 180. The coaptation assistance device 180 can advance over two rails as shown in FIG. 9C. In some embodiments, the rails 184 extend through eyelets or other apertures of the coaptation assistance device 180. The rails 184 can extend through (e.g., be pulled through) the implant delivery catheter 114. The rails 184 can help guide the coaptation assistance device 180 toward the implantation site and/or toward the anchor 146. The rails 184 in some embodiments are flexible guidewires and/or sutures. In some embodiments, the rails 184 are pulled in the direction of the arrows to advance the coaptation assistance device 180 and/or implant delivery catheter 114 through the transseptal sheath 110. In some embodiments, systems that include a plurality of rails 160, such as two rails 160 for example advantageously allows for more controlled and symmetric deployment of the coaptation assistance device.

Figure 10:
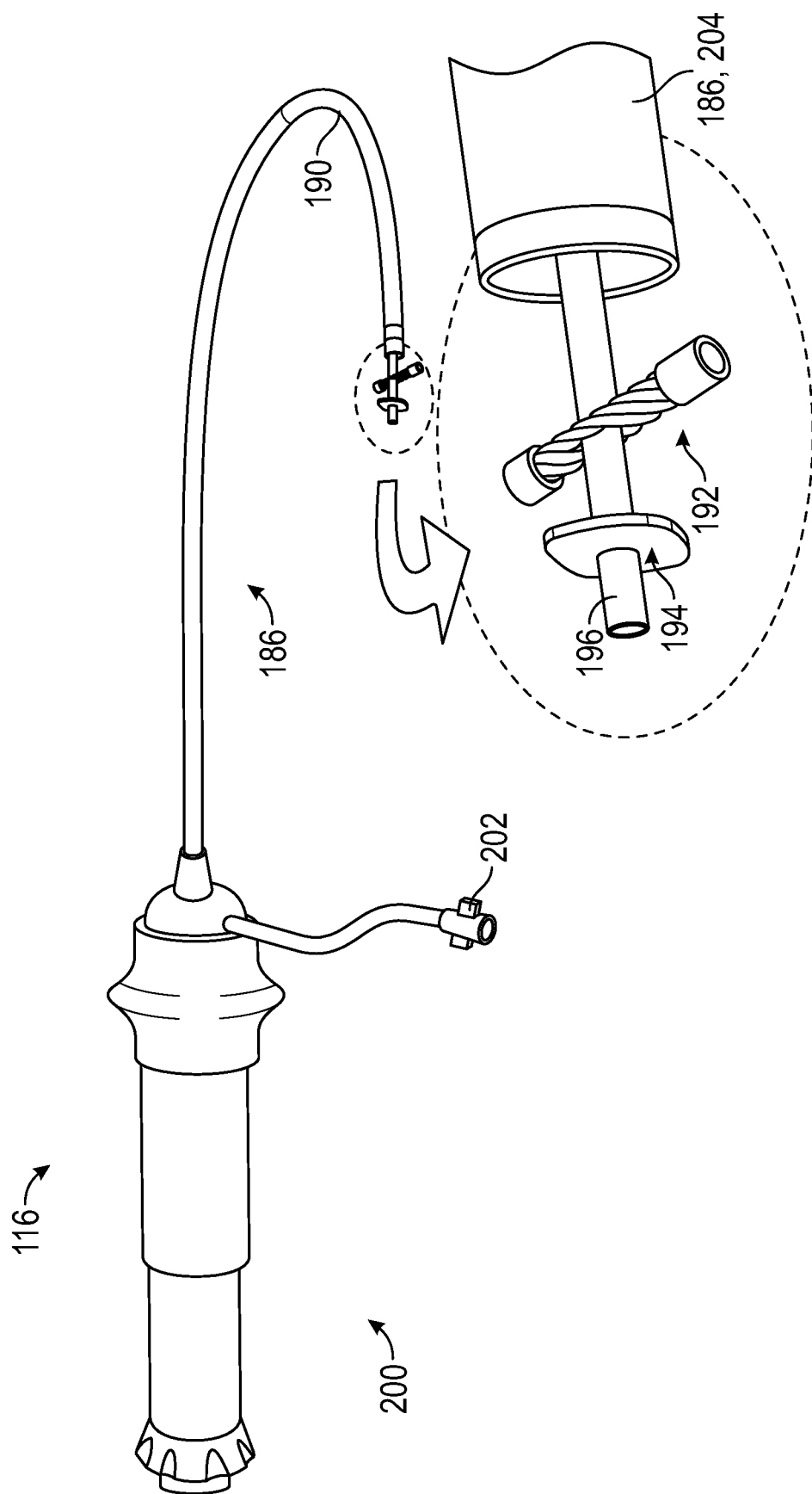
FIG. 10 schematically illustrates an embodiment of a clip delivery catheter.

Referring now to FIG. 10, aspects of the clip delivery catheter 116 are illustrated. The clip delivery catheter 116 comprises a shaft 186. The shaft 186 can be a variable stiffness shaft, with the stiffness varying along a dimension, for instance along the length. The shaft 186 may include a polymer shaft. In some embodiments, the shaft 186 is a braid or coil reinforced polymer shaft. In some embodiments, the shaft 186 has multiple durometers. The shaft 186 can include at least one through lumen (e.g., two, or more through lumens). In some embodiments, the shaft 186 comprises an actively deflectable tip 190 to facilitate navigation of various clips 192 and/or pledgets 194 to the anchoring sites. The clips 192 and pledgets 194 may be comprised of any suitable material, such as suture, flexible material, Nitinol, metal, or plastic. In one embodiment, the preferred material is Nitinol. The deflectable tip 190 can be configured for deflecting along at least a distal section. The deflectable tip 190 can be controlled by various mechanisms, for instance via pullwires operably attached to the deflectable tip 190 and connected to a proximal control.

The clip delivery catheter 116 has sufficient length to fully pass through the transseptal sheath 110 with additional length provided for tip deflection. This distance may be within a range of, e.g., about 90 cm to about 130 cm, and in one embodiment about 110 cm. The delivery catheter may further include a hypotube 196. The implant hypotube 196 can be sized to pass through the shaft 186 of the clip delivery catheter 116. The clip delivery catheter 116 may further include a handle 200 to manipulate the clip delivery catheter 116 within the transseptal sheath 110 and/or body of the patient to steer the hypotube 196 of the clip delivery catheter. The handle 200 may also deploy the clip 192 and/or pledget 194 to the intended site. The handle 200 may further include one or more ports 202, such as a flush, irrigation and/or aspiration port to remove the air from the system and allow injection of fluids such as saline or contrast media to the site of implantation.

The hypotube 196 or other elongate member extends through the clip 192 and/or the pledget 194. In some embodiments, the clip 192 and/or the pledget 194 are initially loaded on the hypotube 196, as shown. In some embodiments, a second hypotube 204 coaxial with and having a larger diameter than the hypotube 196 is used to push the clip 192 and/or the pledget 194 from the hypotube 196. In some embodiments, the deflectable tip 190 having a larger diameter than the hypotube 196 is used to push the clip 192 and/or the pledget 194 from the hypotube 196. Other mechanism can be used to push the clip 192 and/or the pledget 194 (e.g., pusher wire, jaws).

The clip delivery catheter 116 may include pledget 194. The pledget 194 may be of generally circular shape as shown, or may be square or rectangular, elliptical, or any other desired form. The pledget 194 may be comprised of any one of a number of suitable materials known to those of skill in the art. In some instances it may be advantageous to use a material which promotes tissue ingrowth, enhancing the connection of the coaptation assist device 180 to the patient's tissue. In other embodiments, a material which inhibits or is inert with respect to tissue ingrowth may be preferred, such as ePTFE, VTFE, PTFE (poly tetrafluoroethylene), Teflon, polypropylene, polyester, polyethylene terephthalate, or any suitable material. In some embodiments, a coating may be placed on the pledget 194 to inhibit or encourage tissue ingrowth. One or more anchors 146 may penetrate the material of the pledget 194 at a suitable position, securing the pledget 194 to underlying cardiac tissue. Thus, in some embodiments, the pledget 194 may comprise an easily punctured material, such as structural mesh, felt, or webbing.

The clip delivery catheter 116 may include clip 192. In one embodiment, the clip 192 is made from twisted strands of a metal or alloy, e.g., NiTi 2-30 to form a cable. In some embodiments, eight strands are twisted to form clip 192. In one embodiment, the strand diameters are within a range of about 0.01 to about 0.010 inches, and in one embodiment about 0.006 inches.

Figure 11B:
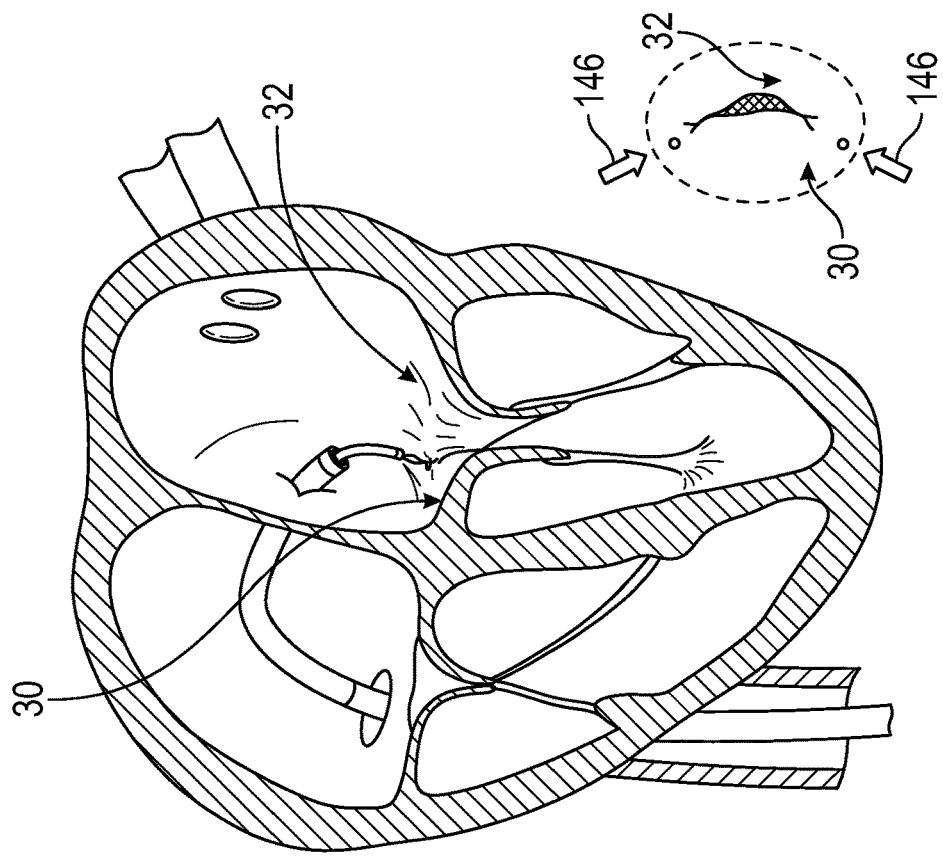
FIG. 11B schematically illustrates the engagement of the first trigonal anchor and the placement of the anchors.
Figure 11A:
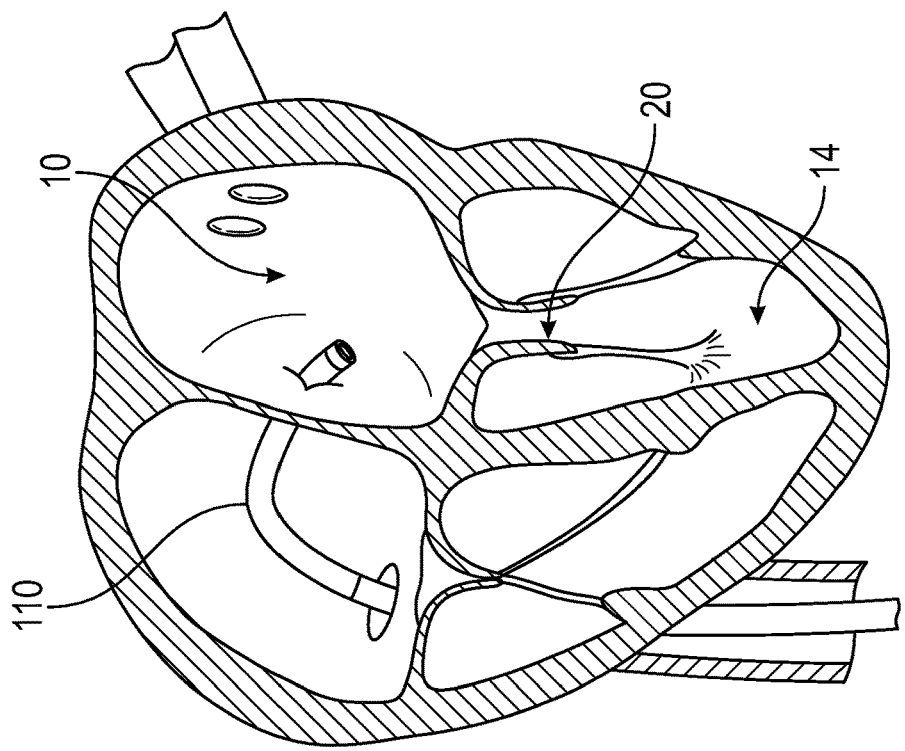
FIG. 11A schematically illustrates the insertion of the transseptal sheath.

Referring now to FIGS. 11A-11F, the implantation steps of one embodiment of the method is shown. As shown in FIG. 11A, a transseptal method for treatment of MR will often include gaining access to the left atrium 10 via a transseptal sheath 110. Access to the femoral vein may be obtained, for example, using the Seldinger technique. From the femoral vein, access can then be obtained via the right atrium 12 to the left atrium 10 by a transseptal procedure. A variety of conventional transseptal access techniques and structures may be employed, so that the various imaging, guidewire advancement, septal penetration, and contrast injection or other positioning verification steps need not be detailed herein.

Transseptal sheaths, such as the transseptal sheath 110 and/or other transseptal sheaths, can have an elongate outer sheath body of the shaft 120 extending between a proximal handle 140 to a distal end, with the handle 140 having an actuator (not shown) for steering a distal segment and/or deflectable tip 122 of the shaft 120 similar to that described above. A distal electrode and/or marker 134 near the distal end of sheath body can help position the sheath within the left atrium. In some embodiments, an appropriately sized deflectable transseptal sheath 110 without steering capability may be guided into position in the left atrium 10 by a steerable transseptal sheath 110 or may be advanced into the left atrium 10 without use of a steerable transseptal sheath 110. Alternatively, deployment may proceed through a lumen of the steerable sheath. Regardless, in some embodiments an outer access sheath will preferably be positioned so as to provide access to the left atrium LA via a sheath lumen.

Referring now to FIG. 11B, the anchor delivery catheter 112 may be advanced through the outer transseptal sheath 110 and into the left atrium 10. The distal end and/or the deflectable tip 144 of the anchor delivery catheter 112 moves within the left atrium 10 by manipulating the proximal handle 154 and by articulating the actuator of the handle (not shown) so as to selectively bend the distal end and/or the deflectable tip 144 of the anchor delivery catheter 112, bringing the distal end of the anchor delivery catheter 112 into alignment and/or engagement with candidate locations for deployment of an anchor 146. The anchor delivery catheter 112 can be aligned optionally under guidance of 2D or 3D intracardiac, transthoracic, and/or transesophageal ultrasound imaging, Doppler flow characteristics, fluoroscopic or X-ray imaging, or another imaging modality.

In some embodiments, an electrode (not shown) at the distal end of the anchor delivery catheter 112 optionally senses electrogram signals and transmits them to an electrogram system EG so as to help determine if the candidate site is suitable, such as by determining that the electrogram signals include a mix of atrial and ventricular components within a desired range (such as within an acceptable threshold of 1:2). Contrast agent or saline may be introduced through the anchor delivery catheter 112.

As shown in FIG. 11B, the anchor 146, for instance a first trigonal anchor, is delivered and engaged with the implantation site. Another anchor, for instance a second trigonal anchor is delivered and engaged with another implantation site. The locations of the anchors 146 are shown in relationship to the anterior leaflet 30 and the posterior leaflet 32 as shown in the smaller snapshot. As shown in FIG. 11C, in some embodiments, each anchor 146 comprises at least one rail 160 (e.g., suture, guidewire) such that the coaptation assistance device 180 can be advance over the rail 160. The coaptation assistance device 180 is advanced over one or more rails 160 (e.g., two rails) as shown by the arrows in FIG. 11C. In this way, the rails 160 facilitate placement of the coaptation assistance device 180. The coaptation assistance device 180 is advanced over the posterior leaflet 32, as shown.

Figure 11D:
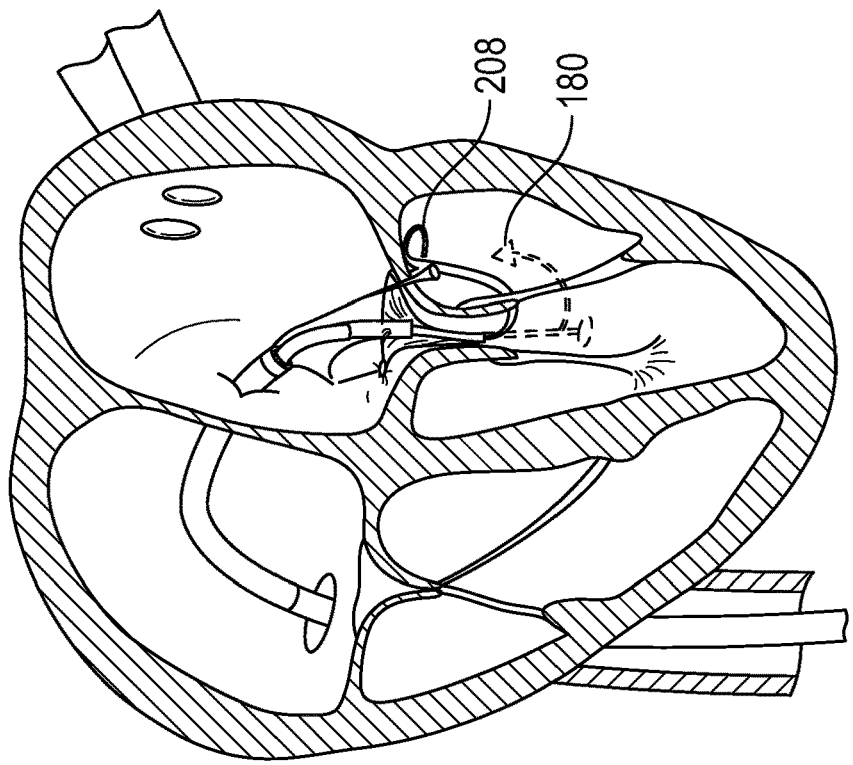
FIG. 11D schematically illustrates the engagement of a ventricular anchor.
Figure 11C:
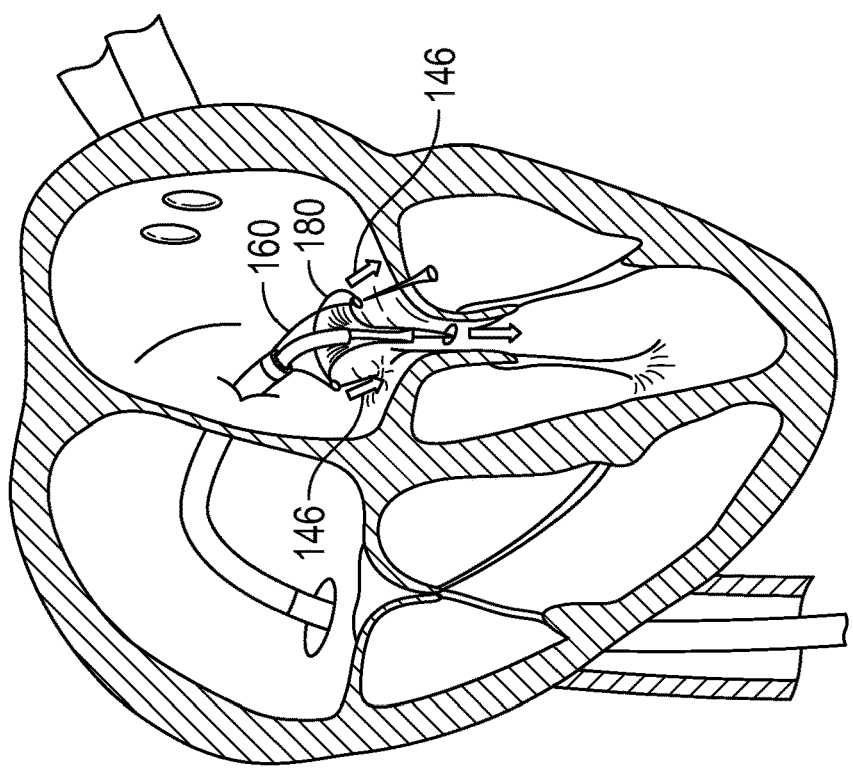
FIG. 11C schematically illustrates the coaptation assistance device deployed and advanced over two rails.
Figure 11F:
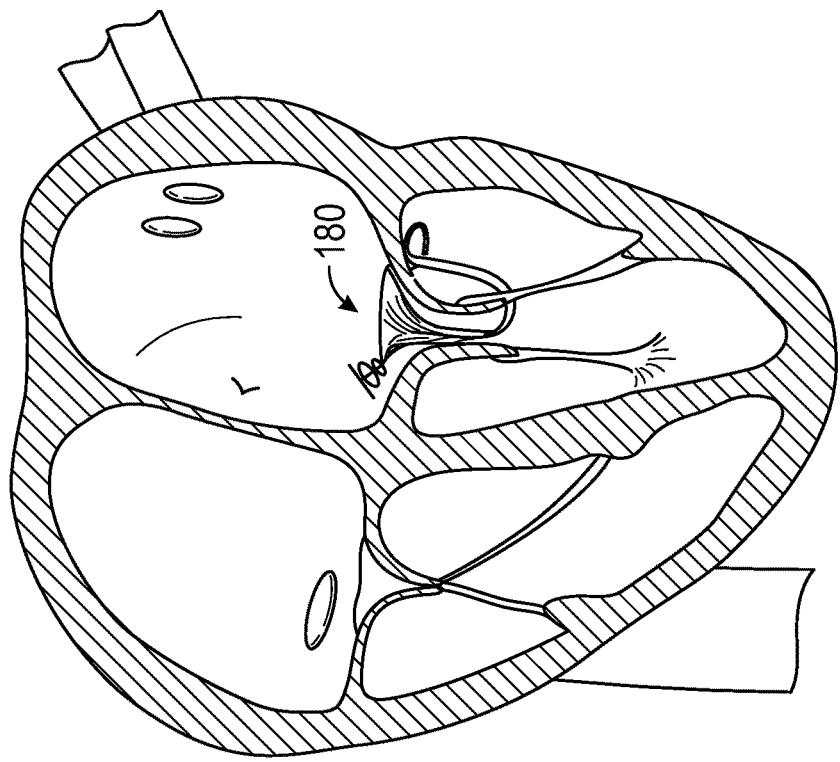
FIG. 11F schematically illustrates the coaptation assistance device deployed across the mitral valve.
Figure 11E:
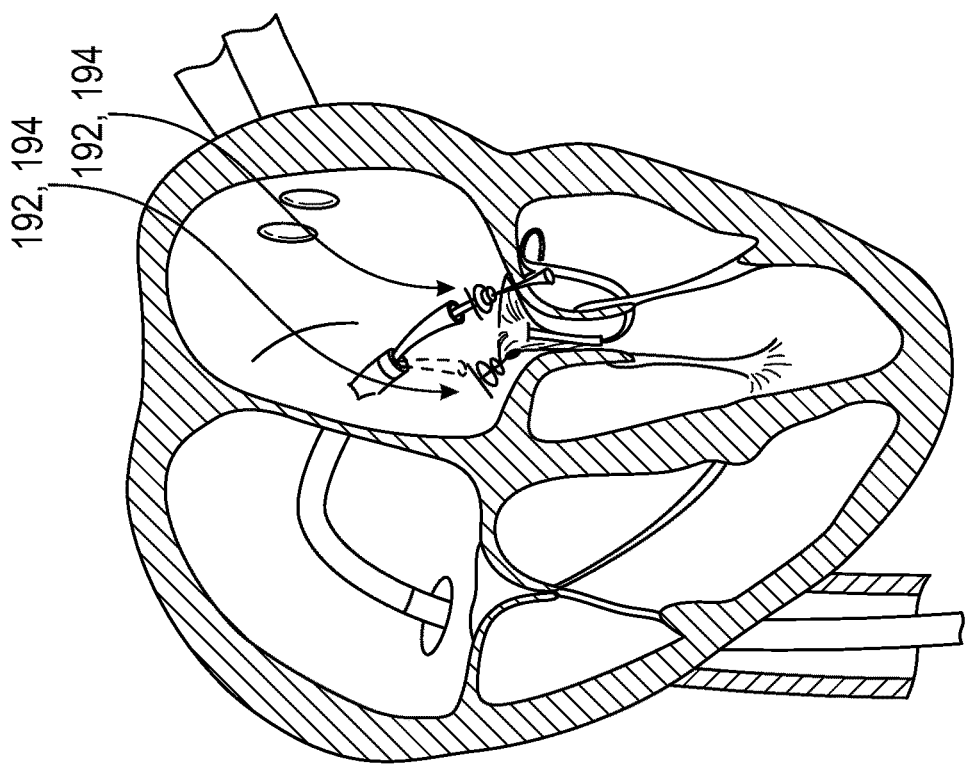
FIG. 11E schematically illustrates the engagement of a clip and a pledget.

As shown in FIG. 11D, the coaptation assistance device 180 is extended through the mitral valve 20 into the left ventricle 14. In some embodiments, the coaptation assistance device 180 may have a ventricular anchor 208 (e.g., ribbon such as the ribbons described herein or other ventricular anchor) that is expanded and engaged to attach the coaptation assistance device 180. After placement of the coaptation assistance device 180 the coaptation assistance device 180 can be locked on the anchors 146 (such as trigonal anchors) by one or more clips 192 and/or one or more pledgets 194, as shown in FIG. 11E. After the coaptation assistance device 180 is deployed and/or locked on the anchors 146, the delivery system 106 is removed, as shown in FIG. 11F.

The aforementioned method can be performed by a physician. In one embodiment, a manufacturer can provides one, some or all of the following: coaptation assistance devices, for instance coaptation assistance device 180, transseptal sheath 110, anchor delivery catheter 112, implant delivery catheter 114, and clip delivery catheter 116. In some embodiments, the manufacturer provides a kit containing some or all of the devices previously described.

In some embodiments, the manufacturer provides instructions for use of the system including one or more of the following steps, or any step previously described in the drawings. The steps may include: gaining access to the left atrium 10 via the transseptal sheath 110; gaining access to the femoral vein via the Seldinger technique; gaining access via the right atrium 12 to the left atrium 10 by a transseptal procedure, utilizing a variety of conventional transseptal access techniques and structures. The steps may include: positioning the transseptal sheath 110 within the left atrium 10; deploying the anchor delivery catheter 112 through the transseptal sheath 110 and into the left atrium 10; bringing the distal end of the anchor delivery catheter 112 into alignment and/or engagement with candidate locations for deployment of the anchor 146; and determining if the candidate site is suitable. The steps may include: delivering and/or engaging the anchor 146, which may be the first trigonal anchor; deploying the rail 160 attached to the anchor 146; advancing the coaptation assistance device 180 over the rail 160; delivering and/or engaging the second anchor 146, which may be a second trigonal anchor; deploying the rail 160 attached to the second anchor; advancing the coaptation assistance device 180 over the rail 160 of the first anchor 146 and the rail 160 of the second anchor 146; facilitating placement of the coaptation assistance device 180 with the rails 160; and positioning the coaptation assistance device 180 over the posterior leaflet 32. The steps may include: extending the coaptation assistance device 180 through the mitral valve 20 into the left ventricle 14; expanding a ventricular anchor 208 of the coaptation assistance device 180; locking the coaptation assistance device 180 on the one or more anchors 146 by the clip 192 and/or the pledget 194; and removing the delivery system 106. These instructions can be written, oral, or implied.

Figure 12A:
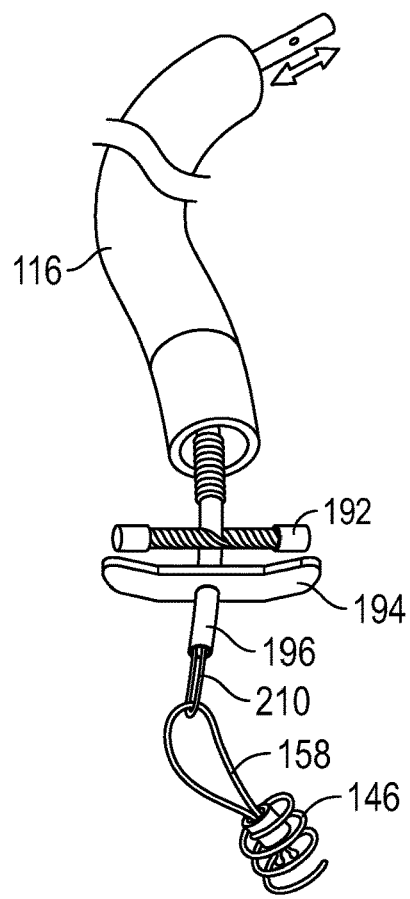
FIG. 12A schematically illustrates a clip and a pledget initially loaded on a hypotube of the clip delivery catheter of FIG. 10.
Figure 12B:
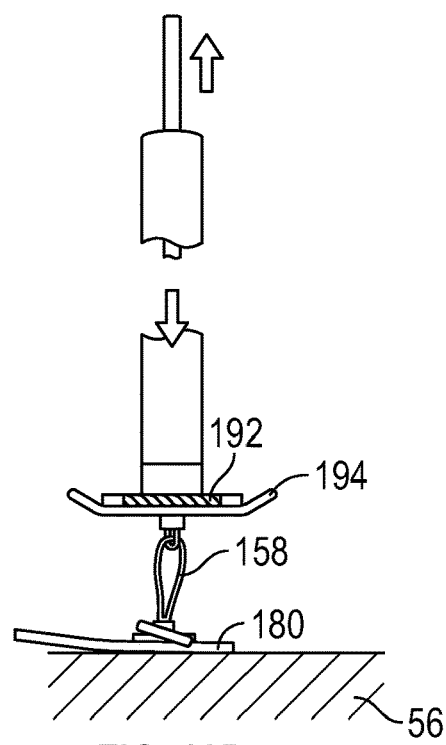
FIG. 12B schematically illustrates the engagement of the clip with an anchor suture.

Referring now to FIGS. 12A-12D, the method of clip 192 and pledget 194 placement is shown. As shown in FIG. 12A, in some embodiments the clip 192 and pledget 194 are initially loaded on the hypotube 196. A guide suture 210 extends in a loop from the hypotube 196. The guide suture 210 can engage the anchor suture 158. The anchor suture 158 is connected to the anchor 146 as shown in FIG. 12A. The hypotube 196 is retracted into the clip delivery catheter 116, as shown by the upward arrow in FIG. 12B. The distal tip of the clip delivery catheter 116 pushes downward on the clip 192, as shown by the downward arrow in FIG. 12B. The clip 192 presses against the pledget 194 and both the clip 192 and the pledget 194 are pressed downward by the clip delivery catheter 116. The clip 192 and the pledget 194 are advanced along the anchor suture 158. The compression force of the clip 192 on the anchor suture 158 locks the clip 192 on the anchor suture 158. The pledget 194 is prevented from translation along the anchor suture 158 by the locking of the clip 192. In some embodiments, the second hypotube 204 is pressed downward on the clip 192 and the pledget 194 instead of, or in addition to, the tip of the clip delivery catheter 116.

Figure 12D:
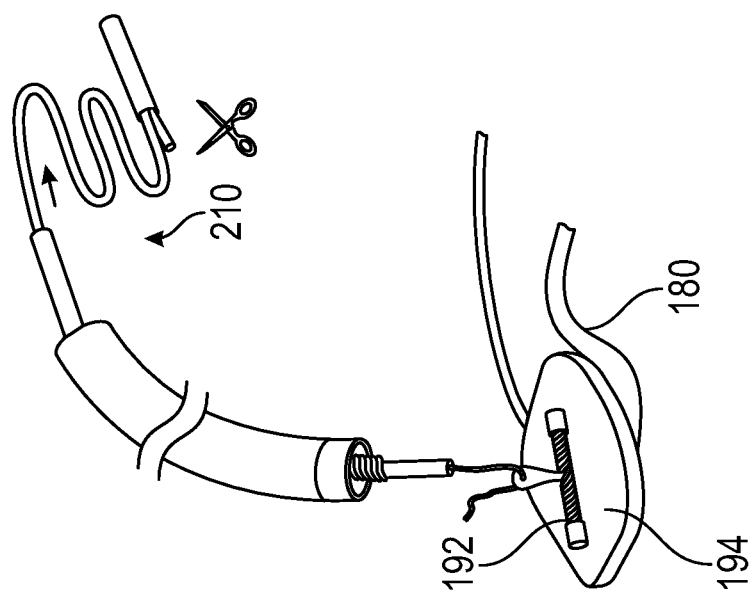
FIG. 12D schematically illustrates the cutting of the guide suture.
Figure 12C:
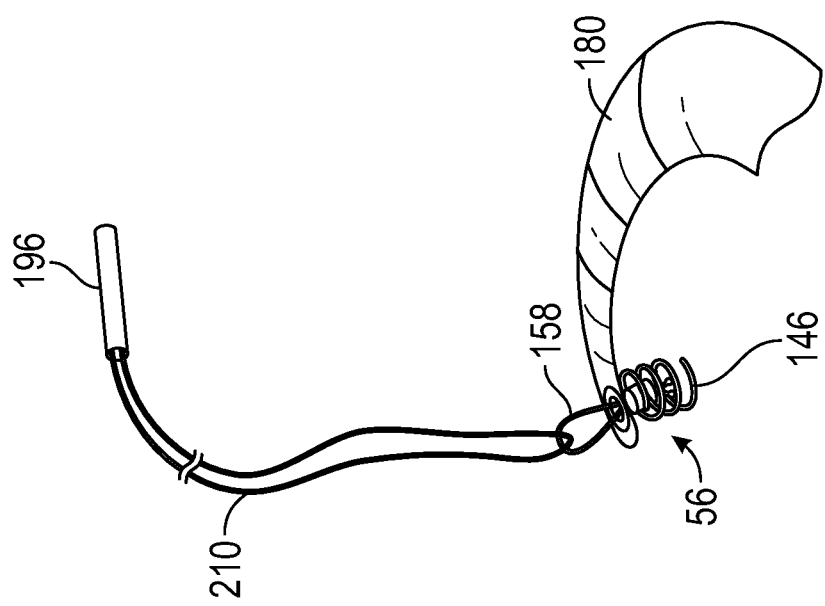
FIG. 12C schematically illustrates the hypotube crimped over a guide suture.

As shown in FIG. 12C, the guide suture 210 can extend from the hypotube 196. In some embodiments, the hypotube 196 is crimped over the guide suture 210. This crimping allows easy introduction of the clip 192 and/or the pledget 194 over the guide suture 210. This crimping also ensures a proper connection between the hypotube 196 and the anchor 146. After the clip 192 and/or the pledget 194 is locked, the guide suture 210 can be cut and retracted through the clip delivery catheter 116, as shown in FIG. 12D.

The aforementioned method can be performed by a physician. In one embodiment, a manufacturer can provide one, some or all of the following: the clip 192, the pledget 194, the hypotube 196, the second hypotube 204, the anchor 146, the anchor suture 158, the guide suture 210, and clip delivery catheter 116. In some embodiments, the manufacture provides a kit containing some or all of the devices previously described.

In some embodiments, the manufacturer provides instructions for use of the system including one or more of the following steps, or any step previously described or inherent in the drawings. The steps may include: initially loading the clip 192 and/or the pledget 194 on the hypotube 196; extending the guide suture 210 from the hypotube 196; engaging the guide suture 210 to the anchor suture 158; connecting the anchor suture 158 to the anchor 146; retracting the hypotube 196 into the clip delivery catheter 116; pressing the distal tip of the clip delivery catheter 116 downward on the clip 192; pressing the clip 192 against the pledget 194; pressing both the clip 192 and the pledget 194 downward; and advancing the clip 192 and the pledget 194 along the anchor suture 158. The steps may include: crimping the hypotube 196 over the guide suture 210; cutting the guide suture 210 after the clip 192 is locked; and retracting the guide suture 210 through the clip delivery catheter 116. These instructions can be written, oral, or implied.

Figure 13:
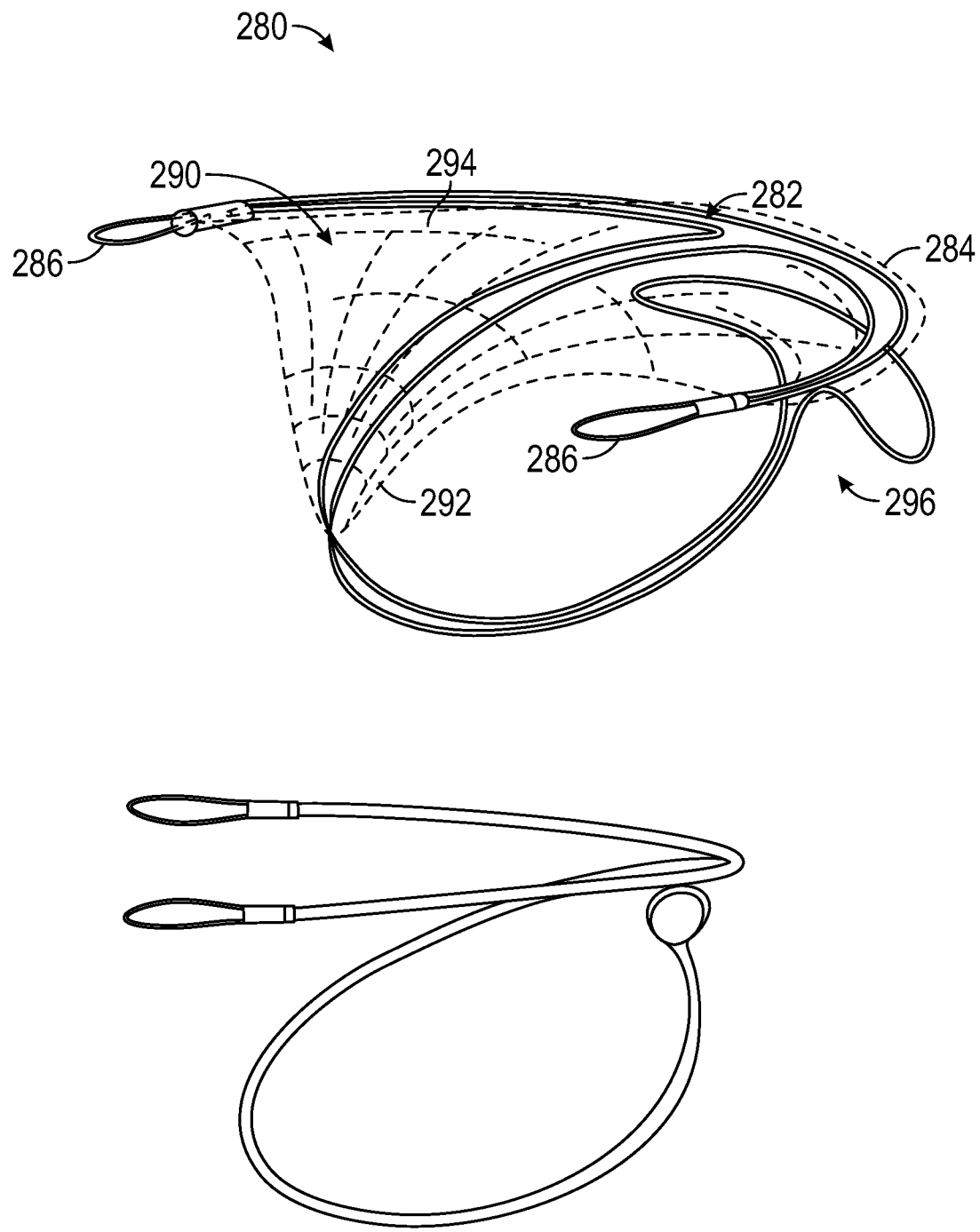
FIG. 13 schematically illustrates an embodiment of the coaptation assistance device.

Turning now to FIG. 13, an embodiment of the coaptation assistance device 280 is shown. The coaptation assistance device 280 can be substantially similar to the coaptation assistance device 80, 180 described herein. The coaptation assistance device 280 can include frame 282 configured to provide structural support to the coaptation assistance device 280. In some embodiments, the frame 282 is collapsible to fit within a delivery catheter, as described herein. In some embodiments, the frame 282 defines a superior edge 284. The frame 282 can include anchor eyelets 286 configured to accept an anchor, such as anchor 146 or other trigonal anchors. The eyelets 286 can be integrated into the surface of the coaptation assistance device 280 or coupled to the coaptation assistance device 280 by any mechanism known in the art. The eyelets 286 correspond to the region of the coaptation assistance device 280 that may be secured to the anterior and posterior fibrous trigones 56, 60. In general, the trigones 56, 60 are located approximately 1-10 mm lateral or medial to their respective commissures 50, 52, and about 1-10 mm more anterior than the commissures 50, 52. In other embodiments, different anchor arrangements may connect the superior edge 284 of the coaptation assistance device 280 can to an anchor, such as anchor 146. For instance, the superior edge 284 can include a hub (not shown) for an anchor to extent or a tether (not shown) connecting the anchor or a hub to the superior edge 284. In some embodiments, the medial end of a tether or the hub is connected to the eyelet 286.

Alternate engagement means are contemplated for connecting the coaptation assistance device 280 to each anchor, including the eyelets 286 and hubs (not shown), but also including other connection means such as, for example, sutures, staples, adhesive or clips. In alternative embodiments, the anchors may form an integrated part of the device. In some embodiments, both anchors inserted within the eyelet 286 are helical anchors. There are many possible configurations for anchoring means, compositions of anchors, and designs for anchoring means.

The coaptation assistance device 280 comprises a body 290. The body 290 comprises a first surface 292 disposed toward a mal-coapting native leaflet, in the instance of a mitral valve 20, the posterior leaflet 32 and a second surface 294 which may be disposed toward the anterior leaflet 30. The first and second surfaces 292, 294 can be considered cooptation surface. The coaptation assistance device 280 can have a geometry which permits it to traverse the mitral valve 20 between attachment sites in the left atrium 10 and/or the left ventricle 14, to provide a coaptation surface 294 for the anterior leaflet 30 to coapt against, and attach to the left atrium 10 or annulus 36 such that it effectively seals off the posterior leaflet 32. In the instance that the posterior leaflet 32 is or has been removed, the coaptation assistance device 280 replaces the posterior leaflet 32.

In some embodiments, the coaptation surface 292, 294 of the coaptation assistance device 280 passes superiorly and radially inwardly from the superior edge 284, before passing distally, in a longitudinal direction perpendicular to the valve plane, or radially inwardly or outwardly with respect to the valve plane.

In some embodiments, the first surface 292 and the second surface 294 of the coaptation assistance device 280 further comprise a covering comprised of ePTFE, polyurethane foam, polycarbonate foam, biologic tissue such as porcine pericardium, or silicone.

One possible frame 282 structure is shown, with frame 282 connecting the eyelets 286. Other frame elements may be incorporated into the coaptation assistance device 280. The frame 282 may be shaped in any number of ways to assist in maintaining the desired shape and curvature of the coaptation assistance device 280. The frame 282 can be made of Nitinol, stainless steel, polymer, or other appropriate materials, and can substantially assist in maintain the geometry of the coaptation assistance device 280, permitting choice of any of a wide variety of covering materials best suited for long term implantation in the heart and for coaptation against the anterior leaflet 30.

The coaptation assistance device 280 may include one or a plurality of anchors, such as anchor 146, to stabilize the coaptation assistance device 280. The coaptation assistance device 280 can also have a ventricular anchor 296 (e.g., ribbons described herein). In some embodiments, the ventricular anchor 296 engages the area under the posterior leaflet 32, the atrial and/or ventricular anchors optionally providing redundant fixation. The anchors may include a plurality of barbs for acute fixation to the surrounding tissue. In other embodiments, the anchors may comprise a plurality of helixes, clips, harpoon or barb-shaped anchors, or the like, appropriate for screwing or engaging the annulus 36 of the mitral valve 20, tissues of the ventricle, and/or other tissues of the atrium, or the atrial or ventricular anchors may attach to the tissue by welding using RF or other energy delivered via the elongate anchor coupling body.

In some embodiments, a ventricular anchor 296 may be included in the form of a tether or other attachment means extending from the valve 20 thru the ventricle septum to the right ventricle 16, or through the apex into the epicardium or pericardium, which may be secured from outside the heart in and combined endo/epi procedure. When helical anchors are used, they may comprise bio-inert materials such as Platinum/Ir, a Nitinol alloy, and/or stainless steel.

Figure 14A:
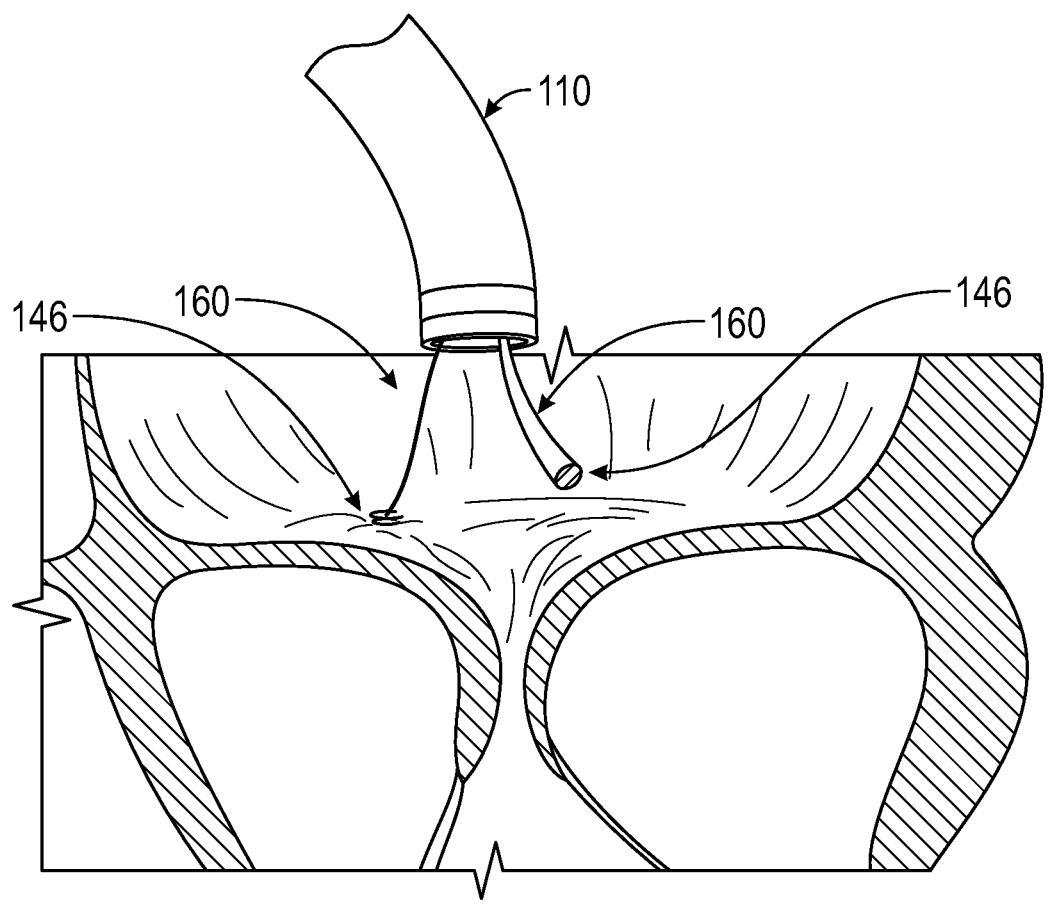
FIG. 14A schematically illustrates the insertion of the transseptal catheter.

Referring now to FIGS. 14A-14D, the implantation steps of one embodiment of the method is shown. As shown in FIG. 14A, a transseptal method for treatment of MR can include gaining access to the left atrium 10 via the transseptal sheath 110. Access to the femoral vein may be obtained using the Seldinger technique. From the femoral vein, access can then be obtained via the right atrium 12 to the left atrium 10 by a transseptal procedure. A variety of conventional transseptal access techniques and structures may be employed, so that the various imaging, guidewire advancement, septal penetration, and contrast injection or other positioning verification steps need not be detailed herein.

Referring now to FIG. 14A, non-limiting candidate locations are illustrated for deployment of an anchor, such as anchor 146, optionally under guidance of 2D or 3D intracardiac, transthoracic, and/or transesophageal ultrasound imaging, Doppler flow characteristics, fluoroscopic or X-ray imaging, or another imaging modality. In some embodiments, a guidewire is used to advance the anchors 146 to the desired location. In some embodiment, a posteromedial trigonal anchor 146 is placed and an anterolateral trigonal anchor 146 is placed using the guidewire.

Figure 14B:
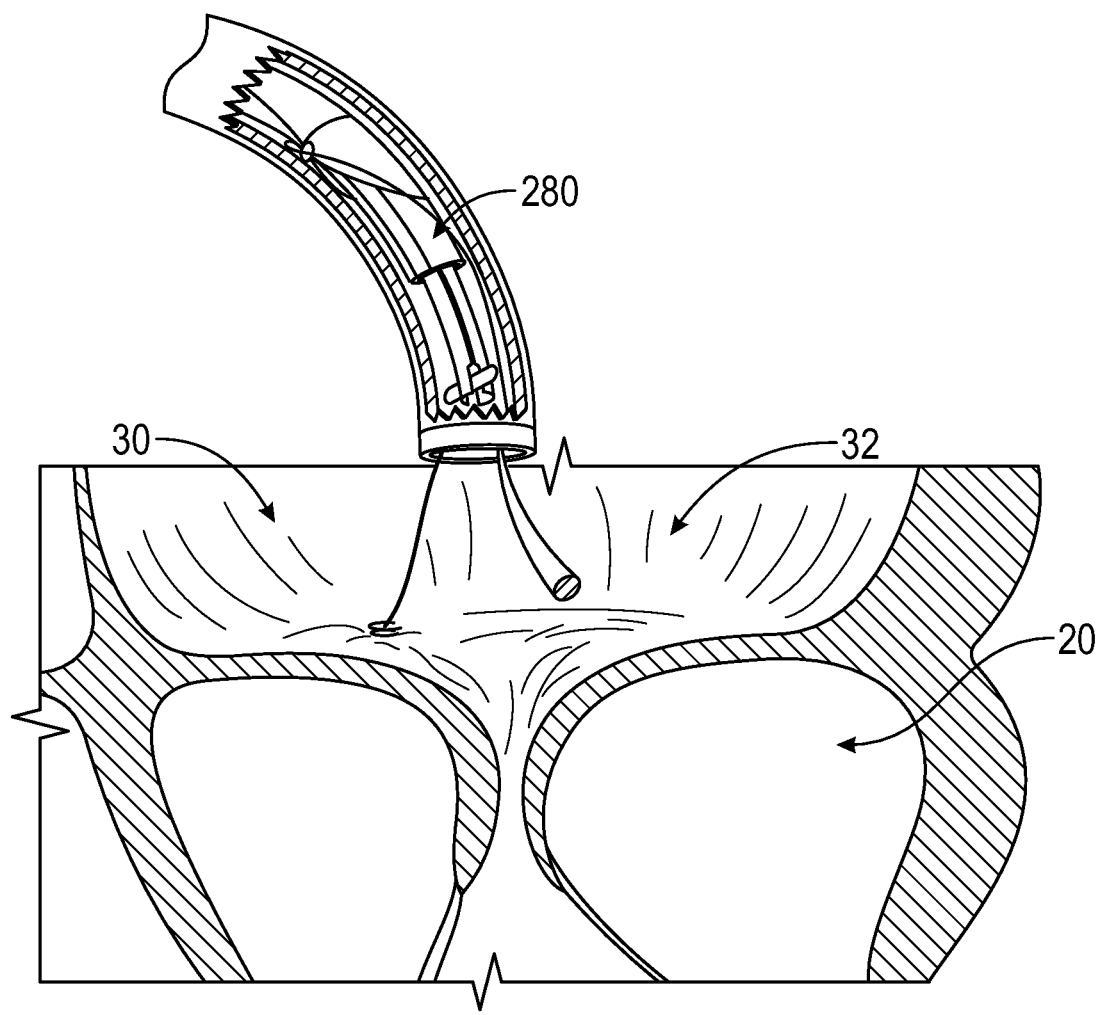
FIG. 14B schematically illustrates the collapsed coaptation assistance device of FIG. 13 and the placement of the anchors.

As shown in FIG. 14B, the first and second trigonal anchors 146 are delivered and engaged. The locations of the trigonal anchors 146 are shown in relationship to the anterior leaflet 30, the posterior leaflet 32, and mitral valve 20 as shown. In some embodiments, each trigonal anchor 146 comprises at least one guidewire or rail 160 such that the coaptation assistance device 280 can be advanced over the rails 160. In some embodiments, the rails 160 advance through a portion of the coaptation assistance device 280 and through the transseptal catheter 110. In some embodiments, the rails 160 extend through eyelets 286.

It can be seen that in some embodiments, the coaptation assistance device 280 is collapsed inside the anchor delivery catheter 112. The radially expandable and/or collapsible structure including frame 282, which can be stent-like in some embodiments, allows the implant to be collapsed. In some embodiments, the coaptation assistance device 280 is collapsed and delivered through the transseptal catheter 110 over the rails 160.

Figure 14C:
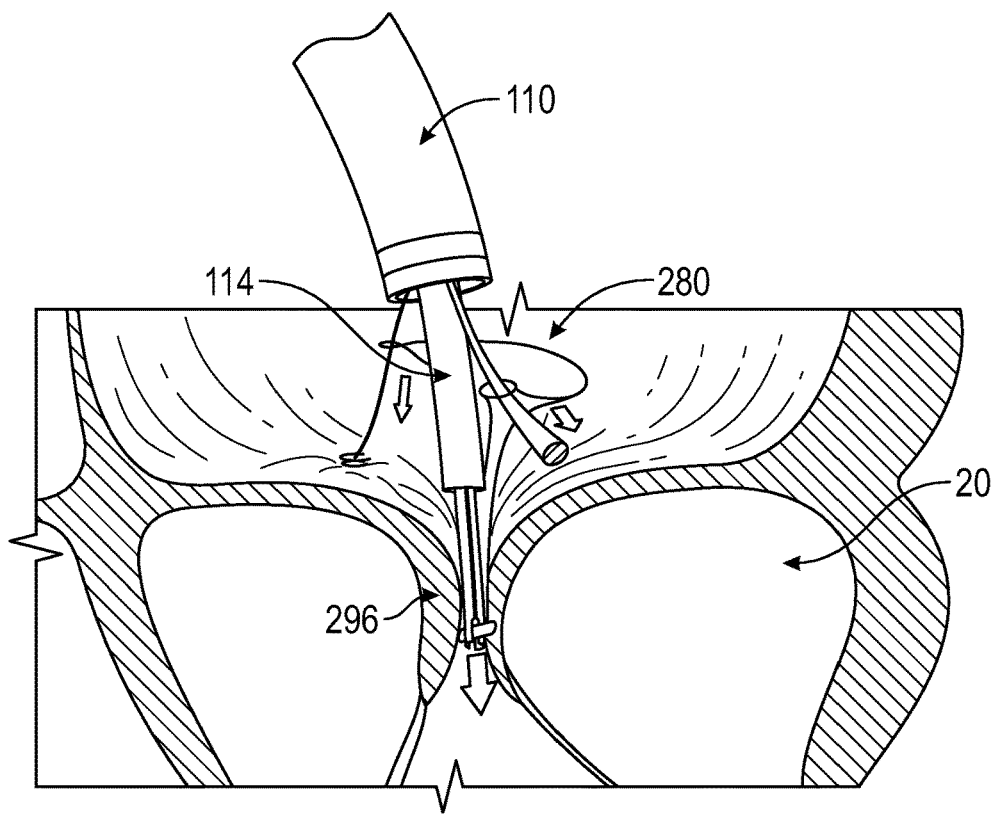
FIG. 14C schematically illustrates the coaptation assistance device deployed and advanced over guidewires.

As shown, after two trigonal anchors 146 are delivered and received; the coaptation assistance device 280 is advanced over two rails 160 as shown by the arrows in FIG. 14C. In this way, the rails 160 facilitate placement of the coaptation assistance device 280. As the coaptation assistance device 280 is delivered over the rails 160, the coaptation assistance device 280 exits the implant delivery catheter 114, allowing the coaptation assistance device 280 to be exposed and expanded.

The coaptation assistance device 280 can be delivered by the implant delivery catheter 114 and may be capable of expanding from a smaller profile to a larger profile to dimensions appropriate for placement in between the valve's native leaflets 30, 32. The coaptation assistance device 280 is expanded as it is exposed from the tip of the implant delivery catheter 114 as shown. In some embodiments, the implant delivery catheter 114 is pulled back to expose the coaptation assistance device 280. The coaptation assistance device 280 is advanced over the posterior leaflet 32.

Figure 14D:
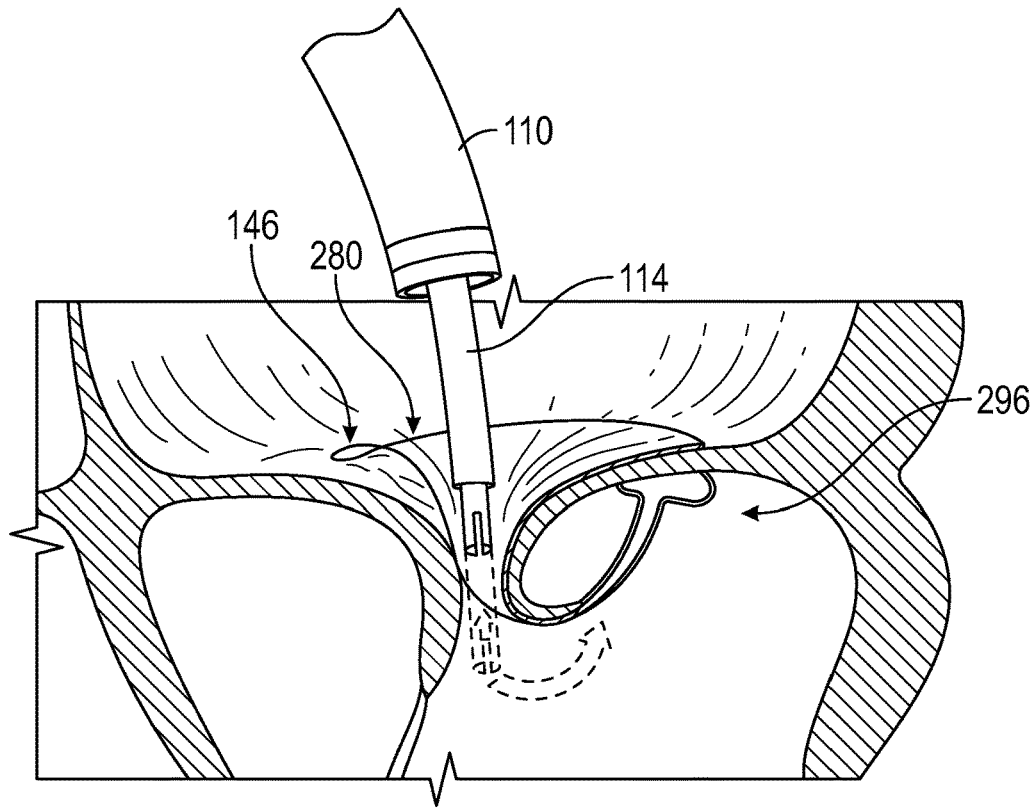
FIG. 14D schematically illustrates the engagement of a ventricular anchor.

As shown in FIG. 14C, the coaptation assistance device 280 can extend through the mitral valve 20 into the left ventricle 14. In some embodiments, the coaptation assistance device 280 may have a ventricular anchor 296 that is expanded to attach the coaptation assistance device 280 to ventricular tissue. The ventricular anchor 296 of the coaptation assistance device 280 can be delivered by the implant delivery catheter 114. A shown in FIG. 14D, the implant delivery catheter 114 is retracted into the transseptal catheter 110. The ventricular anchor 296 of the coaptation assistance device 280 is released and can assume a curved shape as shown. After placement of the coaptation assistance device 280, in some embodiments, the coaptation assistance device 280 is locked on the anchors 146 by one or more clips 192 and/or pledget 194, as shown in FIG. 14D. After the coaptation assistance device 280 is locked on the anchors 146, the catheter delivery system 106 is removed. In some embodiments, the rails 160 are also removed.

The aforementioned method can be performed by a physician. In one embodiment, a manufacturer can provide one, some or all of the following: coaptation assistance device 280, transseptal sheath 110, anchor delivery catheter 112, implant delivery catheter 114, and clip delivery catheter 116. In some embodiments, the manufacturer provides a kit containing some or all of the devices previously described.

In some embodiments, the manufacturer provides instructions for use of the system including one or more of the following steps, or any step previously described or inherent in the drawings. The steps may include: gaining access to the left atrium 10 via a transseptal sheath 110; gaining access to the femoral vein via the Seldinger technique; gaining access via the right atrium 12 to the left atrium 10 by a transseptal procedure, utilizing a variety of conventional transseptal access techniques and structures. The steps may include: positioning the transseptal sheath 110 within the left atrium 10; deploying an anchor delivery catheter 112 through the transseptal sheath 110 and into the left atrium 10; bringing the distal end of the anchor delivery catheter 112 into alignment and/or engagement with candidate locations for deployment of an anchor 146; and determining if the candidate site is suitable. The steps may include: collapsing the coaptation assistance device 280 inside the implant delivery catheter 114; delivering the coaptation assistance device 280 through the transseptal sheath 110 over the rails 160; expanding the coaptation assistance device 280 as it exits the implant delivery catheter 114; and retracting the implant delivery catheter 114. The steps may include: delivering and/or engaging the anchor 146, which may be the first trigonal anchor; deploying a raid 160 attached to each anchor 146; advancing the coaptation assistance device 280 over the rail 160; delivering and/or engaging the second anchor 146, which may be the second trigonal anchor; deploying the rail 160 attached to the second anchor; advancing the coaptation assistance device 180 over the rails 160 delivering and/or engaging the second anchor 146; facilitating placement of the coaptation assistance device 180; and positioning the coaptation assistance device 180 over the posterior leaflet 32. The steps may include: extending the coaptation assistance device 180 through the mitral valve 20 into the left ventricle 14; expanding a ventricular anchor 296 of the coaptation assistance device 180; locking the coaptation assistance device 180 on the anchors 146 by one or more clips 192 and/or pledgets 194; and removing the catheter delivery system 106. These instructions can be written, oral, or implied.

Figure 15:
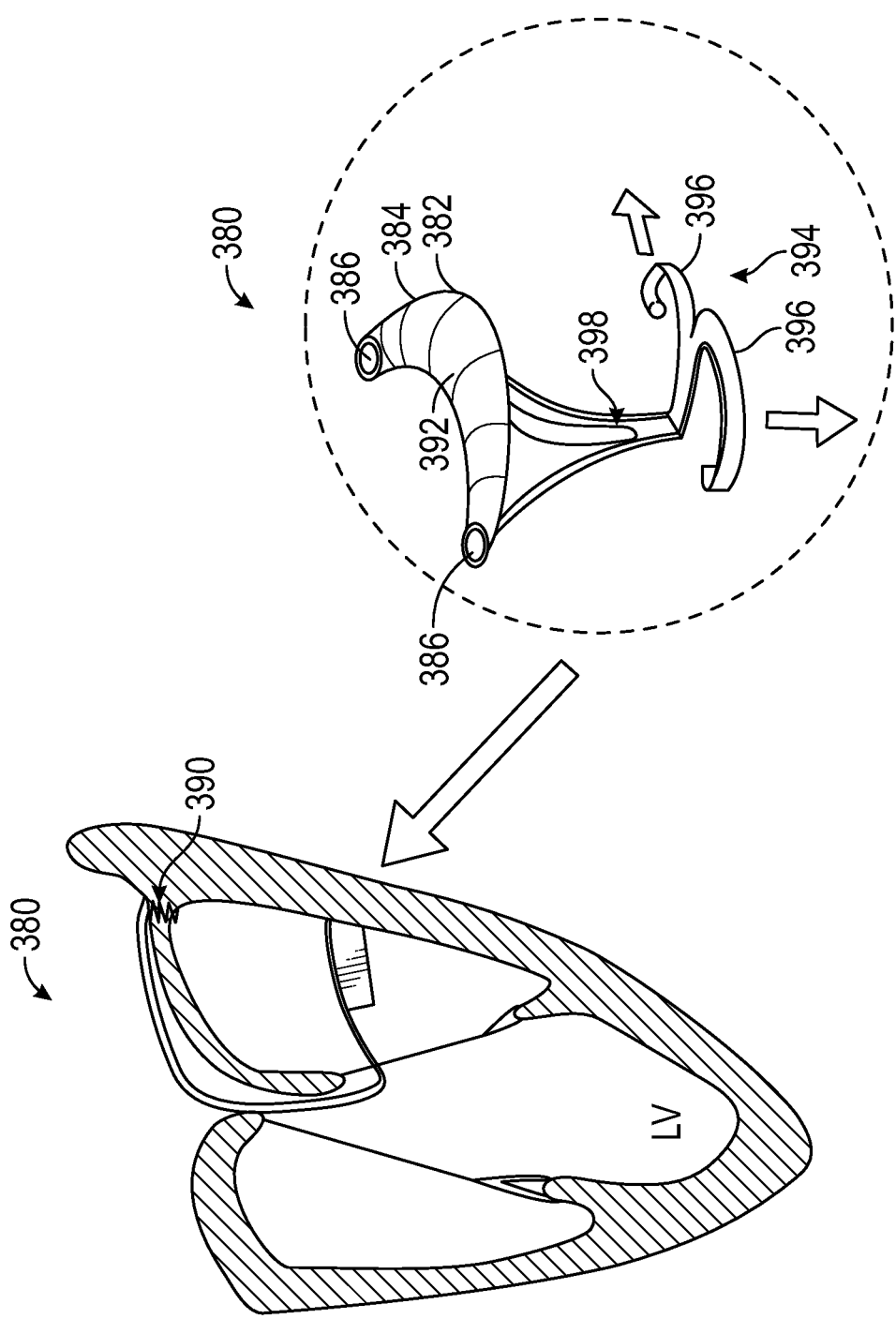
FIG. 15 schematically illustrates an embodiment of the coaptation assistance device.

Turning now to FIG. 15, an embodiment of the coaptation assistance device 380 is shown. The coaptation assistance device 380 can be substantially similar to the coaptation assistance device 80, 180, 280 described herein. The coaptation assistance device 380 can include frame 382 configured to provide structural support to the coaptation assistance device 380. In some embodiments, the frame 382 is collapsible to fit within a delivery catheter, such as implant delivery catheter 114. In some embodiments, the frame 382 defines a superior edge 384. The frame 382 can include anchor eyelets 386 configured to accept an anchor, such as anchor 146. In some embodiments, such as shown in FIG. 15, the eyelets 386 are configured to accept a commissure anchor 390. Commissure anchor locations are provided, such as at lateral ends of an arcuate body portion of the coaptation assistance device 380 as shown. In some embodiments, the commissure anchor 390 is substantially similar or identical to the anchor 146 described herein. The eyelets 386 can be integrated into the surface of the coaptation assistance device 380 or coupled to the coaptation assistance device 380 by any mechanism known in the art. The eyelets 386 correspond to the region of the coaptation assistance device 280 that may be secured to the lateral commissures 50, 52. In other embodiments, different anchor arrangements may connect the frame 382 of the coaptation assistance device 280 to anchors. In other embodiments, different anchor arrangements may connect the frame 282 and/or edge of the coaptation assistance device 380 to the corresponding anatomic structure. In some embodiments, one or more of the commissure anchors 390 are helical anchors, as shown. There are many possible configurations for anchoring, compositions of anchors, and designs as, for example, previously described.

The coaptation assistance device 380 comprises a body 392, which may be configured to permit relatively normal circulation of blood in the ventricular chamber. The body 392 may be elongate and narrow between the anterior and posterior surfaces, taking up minimal space and allowing movement of blood from one side to another and past both lateral aspects of the coaptation assistance device 380.

The coaptation assistance device 380 may include one or a plurality of ventricular anchors 394. The atrial anchors and ventricular anchors can optionally provide redundant fixation. The atrial anchors may include a plurality of barbs for acute fixation to the surrounding tissue. In other embodiments, the atrial anchors may comprise a plurality of helixes, clips, harpoon or barb-shaped anchors, or the like, appropriate for engaging tissues of the ventricle. As shown in FIG. 15, the ventricular anchor can comprise two ribbons 396 that rest against the wall of the left ventricle 14. While two ribbons 396 are shown, in some embodiments one or more ribbons 396 are used (e.g., one, two, three, four etc.). This position may provide stability of the coaptation assistance device 380 and/or the base 398 of the coaptation assistance device 380. When ventricular anchors 394 are used, they may comprise bio-inert materials such as, for example, Platinum/Ir, a Nitinol alloy, and/or stainless steel. In some embodiments, the ribbons 396 comprise NiTi. In some embodiments, the ribbons 396 have a pre-determined curve. The material selection combined with the selected shape provides a ventricular anchor 394 that is spring loaded. In some embodiments, the spring loaded ribbons 396 engage tissues of the left ventricle 14 as shown. Each ribbon 396 can form, for example, a generally U-shaped configuration. The ribbons 396 function as anchors and resist movement of the coaptation assistance device 380. The ribbons 396 together can form a generally W-shaped configuration. The ribbons 396 comprise a rounded surface configured to abut tissue. In some embodiments, the anchors abut tissue and can exert a force on the tissue to stabilize the coaptation assistance device 380, but do not penetrate through one or more tissue layers, e.g., the endocardium or myocardium. In some embodiments, the anchors include a pair of arms with a bias that when in an unstressed configuration can clip onto a portion of the ventricular wall to stabilize the coaptation assistance device, such as in a non-traumatic manner with respect to the ventricular wall. The size and shape of the ribbons can be determined based upon the dimensions of the left ventricle 14, and the left ventricle wall which the ribbons 396 may abut. The ribbons 396 can be generally parallel to the base of the posterior leaflet 32. Other shapes for the ribbons 396 are contemplated. As disclosed herein, the coaptation assistance device 380 is collapsed inside the delivery catheter, such as implant delivery catheter 114. The spring loaded ribbons 396 are capable of being collapsed within the delivery catheter. Upon exiting the catheter, the spring loaded ribbons 396 rapidly expand into the preformed shape. In some embodiments, the ribbons 396 are provided for ventricular attachment. The ribbons 396 allow for very rapid attachment of the coaptation assistance device 380 to the tissue, since the ribbons 396 do not rely on annular sutures and do not require tying knots. The deployment of the ribbons 396 can be faster than engaging a helical anchor, for instance.

Figure 16:
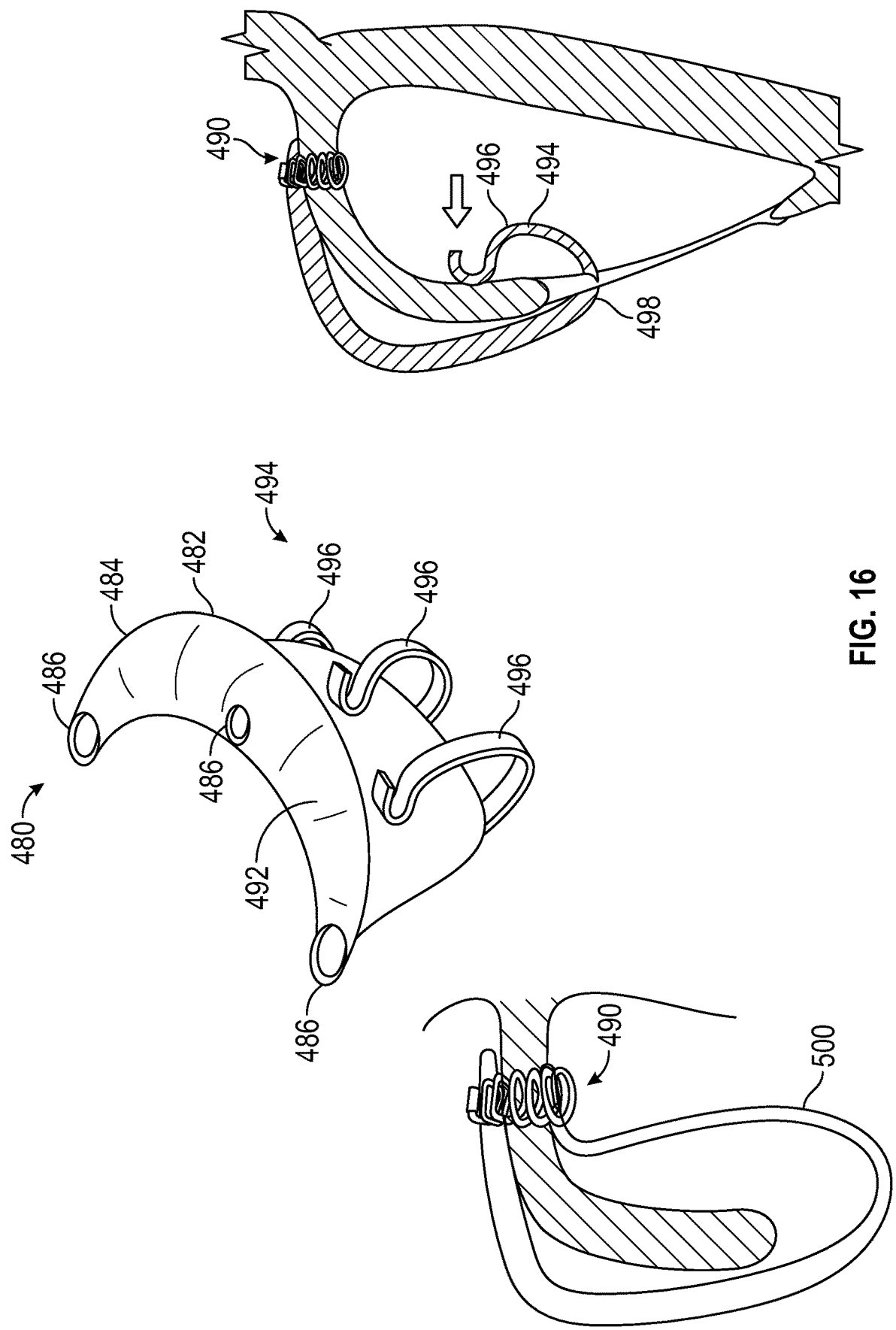
FIG. 16 schematically illustrates an embodiment of the coaptation assistance device.

Turning now to FIG. 16, an embodiment of the coaptation assistance device 480 is shown. The coaptation assistance device 480 can be substantially similar to the coaptation assistance device 80, 180, 280, 380 described herein. The coaptation assistance device 480 can include frame 482 configured to provide structural support to the coaptation assistance device 480. In some embodiments, the frame 482 is collapsible to fit within a delivery catheter, such as implant delivery catheter 114. In some embodiments, the frame 482 defines a superior edge 484. The frame 482 can include anchor eyelets 486 configured to accept an anchor, such as anchor 146. In some embodiments, such as shown in FIG. 16, the eyelets 486 are configured to accept an anchor 490. A plurality of locations for eyelets 486 are provided as shown in FIG. 16. In other embodiments, different anchor arrangements may connect the edge of the coaptation assistance device 480 to the corresponding anatomic structure. In some embodiments, the anchors 490 are helical anchors, as shown. There are many possible configurations for anchoring means, compositions of anchors, and designs for anchoring means. In some embodiments, the anchor 490 can be substantially similar or identical to anchor 146.

The coaptation assistance device 480 may include one or a plurality of atrial anchors 490 and ventricular anchors 494, with the anchors optionally providing redundant fixation. In some embodiments, the atrial anchors 490 may comprise a plurality of helixes, clips, harpoon or barb-shaped anchors, or the like, appropriate for engaging tissues of the ventricle. The atrial anchors 490 may extend through the posterior leaflet as shown. As shown in FIG. 16, the ventricular anchor 494 comprises a plurality of, e.g., three spring-loaded clips or ribbons 496 configured to engage at least a portion of a mitral valve 20, e.g., a portion of posterior leaflet 32 resides in between the ribbons 496 and the body 482. A clip or ribbon can has a bias (e.g., by virtue of its shape memory properties) such that one, two, or more surfaces exert a force, such as a compressive force, on a body structure such as a valve leaflet as shown sufficient to anchor the implant in place. For example, a first portion of a clip can apply a force against a first surface of a valve leaflet as illustrated, and a second portion of the clip can apply a force or rest against a second side of the leaflet, the second side of the leaflet opposite the first side of the leaflet. While three ribbons 496 are shown, in some embodiments any number of ribbons 496 can be used (e.g., one, two, three, four, etc.). This position may provide stability of the coaptation assistance device 480 and/or the implant base 498. This position may not require additional anchoring of the coaptation assistance device to the ventricle 14 or elsewhere. When ribbons 496 are used, they may comprise, e.g., bio-inert materials such as Platinum/Ir, a Nitinol alloy, and/or stainless steel. In some embodiments, the ribbons 496 comprise NiTi. In some embodiments, the ribbons 496 have a predetermined curve. The material selection combined with the selected shape provides a ventricular anchor 496 that is spring loaded. The ribbons 496 rest against the posterior leaflet, as shown. In some embodiments, the spring loaded ribbons 496 engage other tissues of the mitral valve. Each ribbon 496 can form a generally S-shaped configuration. The ribbons 496 function as anchors and resist movement of the coaptation assistance device 480. The ribbons 496 comprise a rounded surface configured to abut tissue. The size and shape of the ribbons 496 can be determined based upon the dimensions of the posterior leaflet 32 which the ribbons 496 may abut. The ribbons 496 can be generally parallel to the tip of the posterior leaflets 32. Other shapes for the ribbons 496 are contemplated. As disclosed herein, the coaptation assistance device 480 is collapsed inside the delivery catheter. The spring loaded ribbons 496 are capable of being collapsed within the delivery catheter, such as implant delivery catheter 114. Upon exiting the catheter, the spring loaded ribbons 496 rapidly expand into the preformed shape. In some embodiments, the ribbons 496 are provided for ventricular attachment. The ribbons 496 allow for very rapid attachment of the coaptation assistance device 480 to the tissue, since the ribbons 496 do not rely on annular sutures and do not require tying knots. The deployment of the ribbons 496 can be faster than engaging a helical anchor, for instance.

In an alternative embodiment, the ribbons 500 are provided. The ribbons 500 extend to the base of the posterior leaflet 32 and align with the anchor 490. The anchor 490 positioned on the posterior leaflet 32 may penetrate the leaflet 32 and connect with the ribbon 500. Alternatively, anchors 490 positioned on the ribbons 500 may penetrate the posterior leaflet from the opposite direction. In some embodiments, the anchor 490 can engage the upper, left atrium side of the coaptation assistance device 480 and the ribbons 500 located in the left ventricle. This configuration may improve the stability of the coaptation assistance device 480. Each ribbon 500 can form a generally L-shaped configuration. The ribbons 500 comprise a rounded surface configured to abut the ventricular side of the posterior leaflet 32. The size and shape of the ribbons can be determined based upon the dimensions of the posterior leaflet 32 which the ribbons 500 may abut. The ribbons 500 can be generally parallel to the tip of the posterior leaflet 32. Other shapes for the ribbons 500 are contemplated. As disclosed herein, the coaptation assistance device 480 is collapsed inside the delivery catheter. The spring loaded ribbons 500 are capable of being collapsed within the delivery catheter, such as implant delivery catheter 114. Upon exiting the catheter, the spring loaded ribbons 500 rapidly transform from a first compressed configuration into the preformed shape of the second expanded configuration. In some embodiments, the clips or ribbons 500 are linear or substantially linear in a compressed configuration. In some embodiments, the ribbons 500 are provided for ventricular attachment. The ribbons 500 allow for very rapid attachment of the coaptation assistance device 480 to the tissue, since the ribbons 500 do not rely on annular sutures and do not require tying knots. The deployment of the ribbons 500 can be faster in some cases than engaging a helical anchor, for instance.

In some embodiments, the clips or ribbons as disclosed in connection with various embodiments herein can be advantageously utilized with a wide variety of cardiac implants not limited to the coaptation assistance devices disclosed herein. For example, the clips or ribbons can be operably connected to replacement heart valves such as mitral or aortic valves, for example, for anchoring and stabilization. In some embodiments, the clips or ribbons can exert a force to clip or otherwise attach onto one or more native valve leaflets, in order to anchor a replacement heart valve in the valve annulus.

Figure 17A:
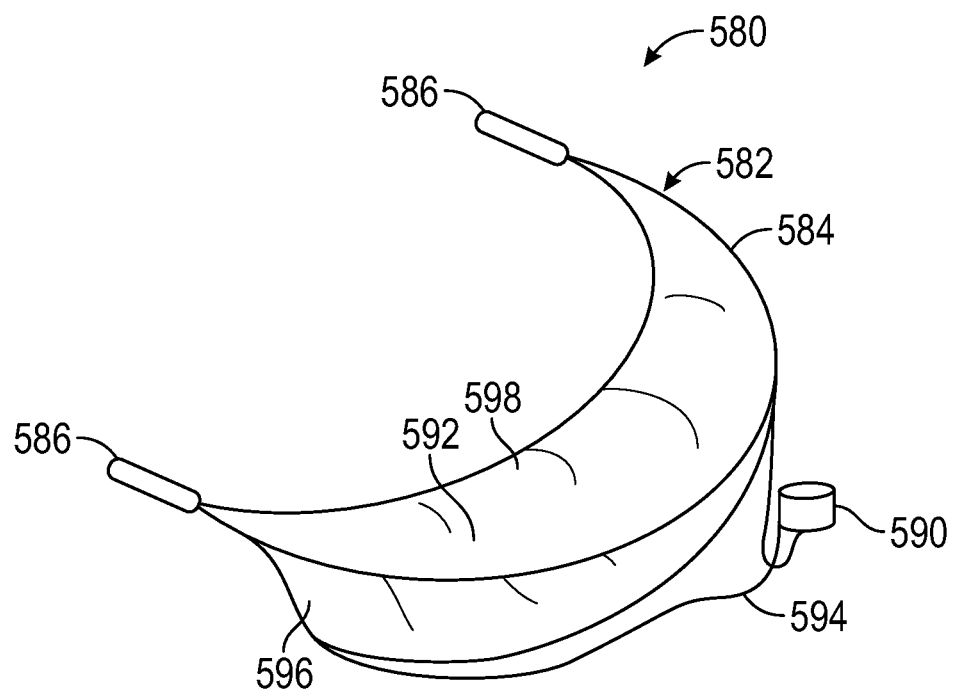
FIG. 17A schematically illustrates an embodiment of the coaptation assistance device.
Figure 17B:
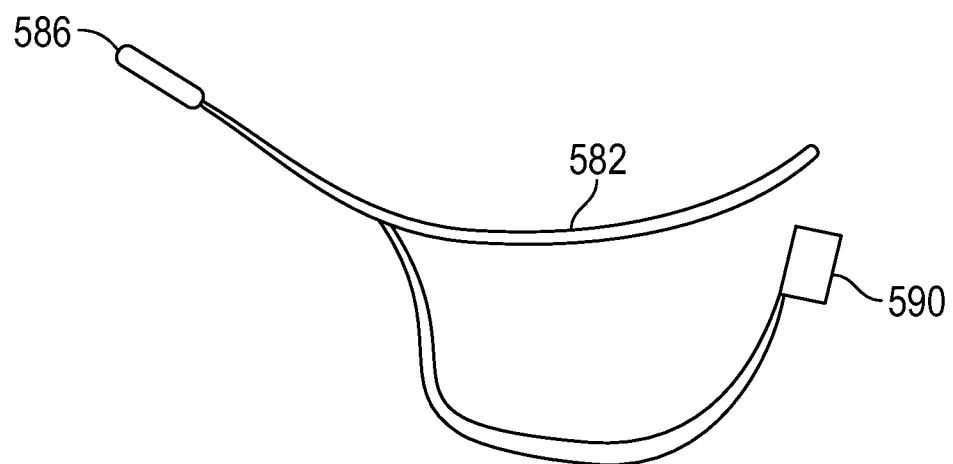
FIG. 17B schematically illustrates a lateral view of an embodiment of the coaptation assistance device.

Turning now to FIGS. 17A-17B, an embodiment of the coaptation assistance device 580 is shown. The coaptation assistance device 580 can be substantially similar to the coaptation assistance device 80, 180, 280, 380, 480 described herein. The coaptation assistance device 580 can include frame 582 configured to provide structural support to the coaptation assistance device 580. In some embodiments, the frame 582 is collapsible to fit within a delivery catheter, such as implant delivery catheter 114. In some embodiments, the frame 582 defines a superior edge 584. The frame 582 can include anchor eyelets 586 configured to accept an anchor, such as anchor 146. In some embodiments, such as shown in FIG. 17, the eyelets 586 are configured to accept a trigonal anchor such as anchor 146. In some embodiments, the eyelets 586 correspond to the region of the coaptation assistance device 580 that may be secured to the anterior and posterior fibrous trigones 56, 60. In some embodiments, the coaptation assistance device 580 comprises a ventricular anchor hub 590. In some embodiments, the hub 590 provides an attachment structure for a ventricular anchor 594.

The coaptation assistance device 580 comprises a body 592. The body 592 comprises a first surface 596 disposed toward a mal-coapting native leaflet, in the instance of a mitral valve 20, the posterior leaflet 32 and a second surface 598 which may be disposed toward the anterior leaflet 30. The first and second surfaces 596, 598 can be considered cooptation surface. The coaptation assistance device 580 can have a geometry which permits it to traverse the mitral valve 20 between attachment sites in the left atrium 10 and left ventricle 14, to provide a coaptation surfaces 598 for the anterior leaflet 30 to coapt against, and attach to the atrium 10 or annulus 36 such that it effectively seals off the posterior leaflet 32. In the instance that the posterior leaflet 32 is or has been removed, the coaptation assistance device 580 replaces the posterior leaflet 32.

In some embodiments, the coaptation surface 598 of the coaptation enhancement element passes superiorly and radially inwardly from the superior edge, before passing distally, in a longitudinal direction perpendicular to the valve plane, or radially inwardly or outwardly with respect to the valve plane.

In some embodiments, the anterior surface 598 and posterior surface 596 of the coaptation assist device 580 further comprise a covering comprised of ePTFE, polyurethane foam, polycarbonate foam, biologic tissue such as porcine pericardium, or silicone.

One possible frame 582 is shown, with frame connecting the eyelets 586. Other frame elements may be incorporated into the coaptation assistance device 580. The frame 582 may be shaped in any number of ways to assist in maintaining the desired shape and curvature of the coaptation assistance device 580. The frame can be made of Nitinol, stainless steel, polymer or other appropriate materials, can substantially assist in maintain the geometry of the coaptation assistance device 580, permitting choice of any of a wide variety of covering materials best suited for long term implantation in the heart and for coaptation against the anterior leaflet 30.

The coaptation assistance device 580 may include one or a plurality of anchors to stabilize the coaptation assistance device 580, with the anchors optionally providing redundant fixation. The anchors may include a plurality of barbs for acute fixation to the surrounding tissue. In other embodiments, the anchors may comprise a plurality of helixes, clips, harpoon or barb-shaped anchors, or the like, appropriate for screwing or engaging into the annulus of the mitral valve 20, tissues of the left ventricle 14, and/or other tissues of the left atrium 10. The anchors may attach to the tissue by welding using RF or other energy delivered via the elongate anchor coupling body.

Figure 18A:
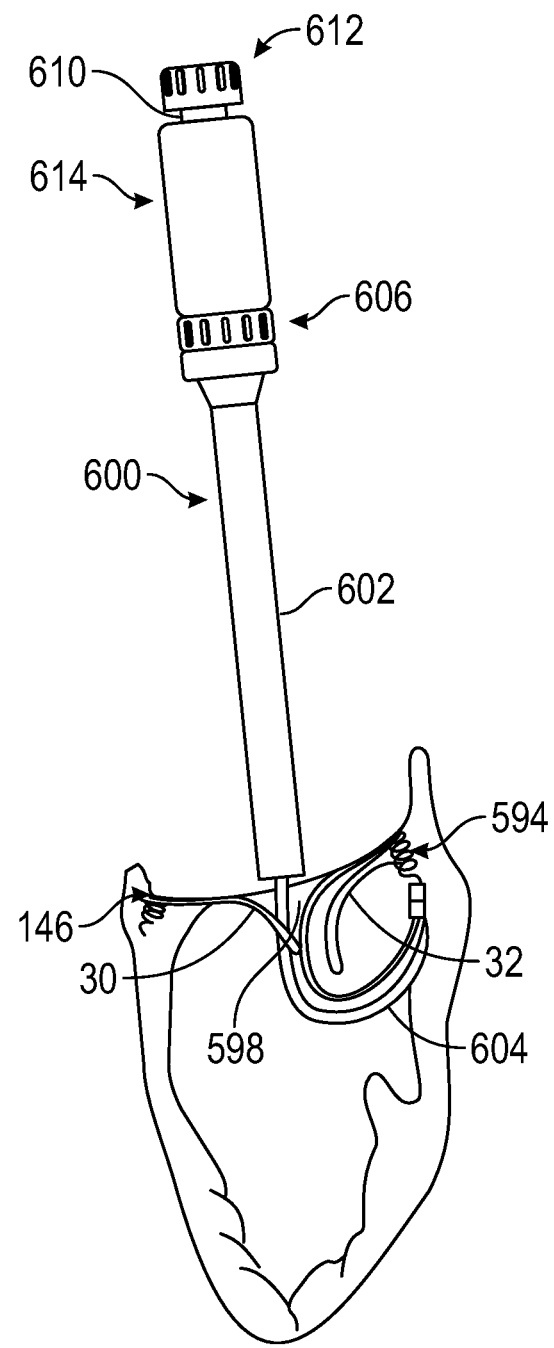
FIG. 18A schematically illustrates an embodiment of the delivery catheter.
Figure 18B:
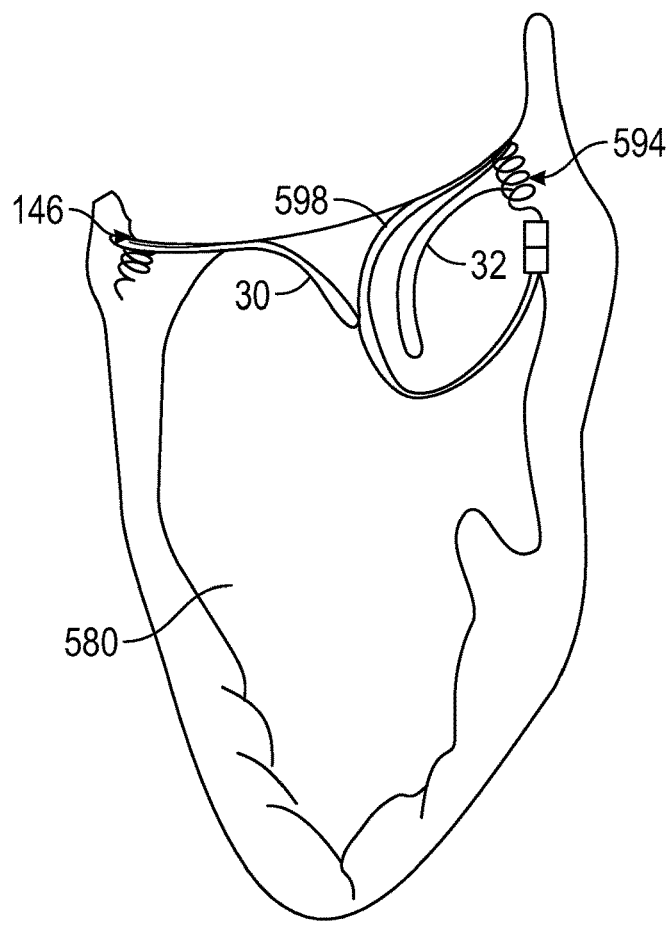
FIG. 18B schematically illustrates the coaptation assistance device of FIG. 17A deployed across the mitral valve.
Figure 18C:
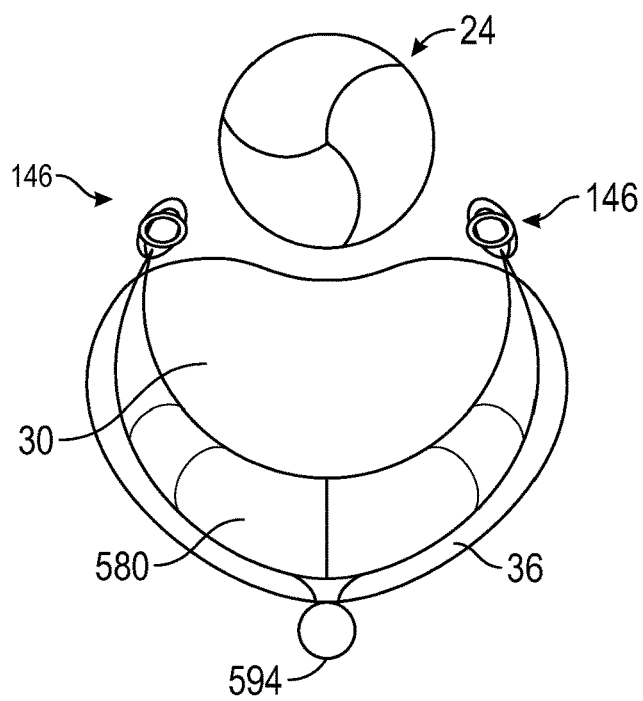
FIG. 18C schematically illustrates the top view of the coaptation assistance device deployed across the mitral valve.

Referring now to FIGS. 18A-18C, the implantation steps of one embodiment of the method is shown. As shown in FIGS. 18A, a delivery catheter 600 is advanced into the left atrium 10. The delivery catheter 600 can be substantially similar to implant delivery catheter 114. In some embodiments, the delivery catheter 600 may be advanced through the outer transseptal sheath 110 and into the left atrium 10. FIG. 18A shows an embodiment of the delivery catheter 600. The delivery catheter 600 may include a shaft 602 made of a polymer for example. In some embodiments, the shaft 602 is a braid or coil reinforced polymer shaft. In some embodiments, the shaft 602 has multiple durometers. In other embodiments, the delivery catheter 600 comprises an actively deflectable tip 604 to facilitate navigation of one or more anchors 594 to the anchoring sites. For instance, the deflectable tip 604 can access the site under the posterior leaflet. The delivery catheter 600 may include a deflection knob 606 to control the deflectable tip 604.

The delivery catheter may include a drive shaft 610. The drive shaft 610 has a feature at the tip to engage with and allow transmission of torque to the anchor 594. In some embodiments, the drive shaft 610 is flexible. In some embodiments, the drive shaft 610 is capable of being advanced or retracted. The delivery catheter 600 may include a knob 612 that is connected to the drive shaft 610. The knob 612 is internally connected to the drive shaft 610 thereby allowing transmission of torque to the anchor 594 when the knob 612 is rotated. This enables simple manipulation of the anchor position and torque.

The coaptation assistance device 580 can be delivered by the delivery catheter 600 and may be capable of expanding from a smaller profile to a larger profile to dimensions appropriate for placement in between the valve's native leaflets 30, 32. The coaptation assistance device 580 is expanded as it is exposed from the tip of the delivery catheter 600. In some embodiments, the delivery catheter 600 is pulled back to expose the coaptation assistance device 580. The delivery catheter 600 may further include a control handle 614 to manipulate the coaptation assistance device 580 and/or, to manipulate the docking and undocking of the coaptation assistance device 580 with the delivery catheter 600 and/or to facilitate placement of the coaptation assistance device 580.

Referring now to FIG. 18A, the distal end of the delivery catheter 600 moves within the left atrium 10 by manipulating the control handle 614 and by articulating the actuator of deflection knob 612 so as to selectively bend the deflectable tip 604 and/or the distal end of the delivery catheter 600. The deflectable tip 604 and/or the distal end of the delivery catheter 600 can be brought into alignment and/or engagement with candidate locations for deployment of the anchor 594. The deflectable tip 604 and/or distal end of the delivery catheter 600 can be deflected to access the site under the posterior leaflet 32. In some embodiments, the distal end of the delivery catheter 600 is brought into alignment with the wall of the left ventricle 14 to facilitate placement of the ventricle hub 590 and/or ventricle anchor 594.

As shown in FIG. 18A, the trigonal anchors 146 are delivered and engaged as described herein. The coaptation assistance device 580 is extended through the mitral valve 20 into the left ventricle 14. In some embodiments, the coaptation assistance device 580 may have a ventricular hub 590 and/or ventricular anchor 594. The ventricular anchor 594 as shown is a helical anchor, but other anchor designs are contemplated. In some embodiments, the ventricular anchor 594 extends from the left ventricle 14 to the left atrium 10 as shown.

As shown in FIGS. 18B-18C, the coaptation assistance device 580 is anchored and the delivery catheter 600 is removed. The coaptation surface 598 is placed between the anterior leaflet 30 and the posterior leaflet 32. The ventricular anchor 594 and the trigonal anchors 146 are secured. In some embodiments, there is an anteriolateral trigonal anchor 146 and a posteriomedial trigonal anchor 146 as shown in FIG. 18C.

The aforementioned method can be performed by a physician. In one embodiment, the manufacturer can provide one, some or all of the following: coaptation assistance device 580, delivery catheter 600, trigonal anchor 146, and ventricular anchor 594. In some embodiments, the manufacturer provides a kit containing some or all of the devices previously described.

In some embodiments, the manufacturer provides instructions for use of the system including one or more of the following steps, or any step previously described or inherent in the drawings. The steps may include: positioning the delivery catheter 600 within the left atrium 10; bringing the deflectable tip 604 and/or the distal end of the delivery catheter 600 into alignment and/or engagement with candidate locations for deployment of an anchor; and determining if the candidate site is suitable. The steps may include: delivering and/or engaging the first trigonal anchor 146; delivering and/or engaging the second trigonal anchor 146; facilitating placement of the coaptation assistance device 580; and positioning the coaptation assistance device 580 over the posterior leaflet. The steps may include: extending the coaptation assistance device 580 through the mitral valve 20 into the left ventricle 14; locking the coaptation assistance device 580 on the trigonal anchors 146 by one or more clips 192 and/or pledgets 194; and removing the catheter delivery system. These instructions can be written, oral, or implied.

It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "inserting a coaptation assist body proximate the mitral valve" includes "instructing the inserting of a coaptation assist body proximate the mitral valve." The ranges disclosed herein also encompass any and all overlap, subranges, and combinations thereof. Language such as "up to," "at least," "greater than," "less than," "between," and the like includes the number recited. Numbers preceded by a term such as "approximately", "about", and "substantially" as used herein include the recited numbers, and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. An implant for treating mal-coaptation of a heart valve, the heart valve having an annulus and posterior and anterior leaflets with an open configuration and a closed configuration, the implant comprising:
    a coaptation assist body comprising a superior edge, an inferior edge, and lateral edges that bound a first surface and a second surface, the first surface configured to be disposed toward the posterior leaflet, the second surface configured to be disposed toward the anterior leaflet to allow the anterior leaflet to coapt with the coaptation assist body,
    the coaptation assist body comprising a central orifice spaced inward from the superior edge, the inferior edge, and the lateral edges, the coaptation assist body comprising lateral orifices spaced laterally from the central orifice, the coaptation assist body surrounding the central orifice and lateral orifices,
    a plurality of ribbons, the plurality of ribbons comprising at least one curve, the plurality of ribbons movable from a first compressed configuration to a second expanded configuration;
    an atrial anchor comprising a helical body configured to extend through the central orifice and wherein the atrial anchor is configured to rotate into the annulus; and
    lateral anchors, each lateral anchor comprising a helical body configured to extend through a lateral orifice of the lateral orifices,
    wherein the lateral anchors are configured to rotate into the annulus, wherein the atrial anchor and the lateral anchors provide the only fixation to the annulus.

2. The implant of claim 1, wherein at least one ribbon of the plurality of ribbons comprise two discrete curves.

3. The implant of claim 1, wherein the plurality of ribbons are configured to rest against the tissue of a heart.

4. The implant of claim 1, wherein the plurality of ribbons resist movement of the coaptation assist body without penetrating a myocardium.

5. The implant of claim 1, wherein the plurality of ribbons comprise a nickel and titanium alloy.

6. The implant of claim 1, wherein the atrial anchor comprises an outer diameter between 1 mm and 6 mm.

7. The implant of claim 1, wherein the atrial anchor comprises a pitch of 0.4 mm to 1.5 mm.

8. The implant of claim 1, wherein the atrial anchor comprises a wire.

9. The implant of claim 8, wherein the wire comprises a diameter of 0.25 mm to 0.75 mm.

10. The implant of claim 1, wherein the atrial anchor comprises a drive continuation extending proximally from the helical body.

11. An implant for treating mal-coaptation of a heart valve, comprising:

an implant body configured to improve function of the heart valve, the implant body comprising a superior edge, an inferior edge, and lateral edges that bound a first surface and a second surface, the first surface configured to be disposed toward a posterior leaflet and the second surface configured to be disposed toward an anterior leaflet, the implant body comprising a discrete central opening spaced inward from the superior edge, the inferior edge, and the lateral edges, the implant body comprising discrete lateral openings spaced apart from the discrete central opening;

a plurality of ribbons, the plurality of ribbons comprising a shape memory material comprising at least one curve, the plurality of ribbons movable from a first compressed configuration to a second expanded configuration;

an atrial anchor comprising a helical body, wherein the atrial anchor is configured to be rotated relative to the discrete opening to be driven into tissue of an annulus; and lateral anchors, each lateral anchor comprising a helical body, wherein each lateral anchor is configured to be rotated relative to a discrete lateral opening of the lateral openings to be driven into tissue of the annulus, wherein the implant does not attach to an anterior aspect of the annulus and only attaches to a posterior aspect of the annulus with the atrial anchor and the lateral anchors.

12. The implant of claim 11, wherein the implant body is configured to traverse a mitral valve.

13. The implant of claim 11, wherein the implant body is configured to attach to a site in a left ventricle.

14. The implant of claim 11, wherein the second surface comprises a coaptation surface for the anterior leaflet to coapt against.

15. The implant of claim 11, wherein the implant body effectively seals off or replaces the posterior leaflet.

* * * * *